(12) United States Patent
Kinney et al.

(10) Patent No.: US 7,256,014 B2
(45) Date of Patent: Aug. 14, 2007

(54) METHOD TO INCREASE HYDROPHOBIC COMPOUND TITER IN A RECOMBINANT MICROORGANISM

(75) Inventors: Anthony J. Kinney, Wilmington, DE (US); Hao Ni, Newark, DE (US); Pierre E. Rouviere, Wilmington, DE (US); Wonchul Suh, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 46 days.

(21) Appl. No.: 11/190,386

(22) Filed: Jul. 27, 2005

(65) Prior Publication Data
US 2007/0026484 A1  Feb. 1, 2007

(51) Int. Cl.
*C12P 1/00* (2006.01)
*C12N 1/00* (2006.01)

(52) U.S. Cl. ............... 435/41; 435/252.3; 435/254.11; 435/257.2; 435/320.1

(58) Field of Classification Search .................... None
See application file for complete search history.

(56) References Cited

U.S. PATENT DOCUMENTS

| | | | | |
|---|---|---|---|---|
| 5,948,682 | A * | 9/1999 | Moloney | 435/483 |
| 6,753,167 | B2 * | 6/2004 | Moloney et al. | 435/69.8 |
| 6,924,363 | B1 * | 8/2005 | Moloney et al. | 530/412 |
| 2004/0219629 | A1 | 11/2004 | Cheng et al. | |

FOREIGN PATENT DOCUMENTS

WO    WO 01/29236 A1    4/2001

OTHER PUBLICATIONS

Ignacio Arechaga et. al., Characterisation of New Intracellular Membranes in *Escherichia coli* Accompanying Large Scale Over-Production of the B Subunit of F1F0 ATP Synthase, Febs Lett., 2000, pp. 215-219, vol. 482.
B. Buchanan et. al., Symposium: Redox Regulation, American Society of Plant Physiologists, 2000, pp. 17-18.
Sikkema et. al., Mechanisms of Membrane Toxicity of Hydrocarbons, Microbiol. Rev., 1995, pp. 201-222, vol. 59.
Lee et. al., Biosynthesis of Structurally Novel Carotenoids in *Escherichia coli*, Chemistry & Biology, 2003, pp. 453-462, vol. 10.
Shibata et. al., Molecular Characteristics of Astaxanthin and B-Carotene in the Phospholipid Monolayer and Their Distributions in the Phospholipid Bilayer, Chem. Phys. Lipids, 2001, pp. 11-22, vol. 113.
C. Schmidt-Dannert et. al., Metabolic Engineering Towards Biotechnological Production of Carotenoids in Microorganisms, Appl. Microbiol. Biotechnol., 2002, pp. 1-11, vol. 60.
Albrecht et. al., Metabolic Engineering of the Terpenoid Biosynthetic Pathway of *Escherichia coli* for Production of the Carotenoids B-Carotene and Zeaxanthin, Biotechnol. Lett., 1999, pp. 791-795, vol. 21.

* cited by examiner

Primary Examiner—Nashaat T. Nashed

(57) ABSTRACT

Expression of at least one plant oleosin gene in a microbial cell engineered to produce hydrophobic/lipophilic compounds significantly increases the overall titer of the compound. The hydrophobic nature of the oleosin core is believed to increase the microbial host cell's internal storage capacity for any hydrophobic/lipophilic compound. The method is exemplified using a bacterial host cell engineered to produce significant amount of various carotenoids.

14 Claims, 8 Drawing Sheets

Isoprenoid Pathway in E. coli

Figure 2A:
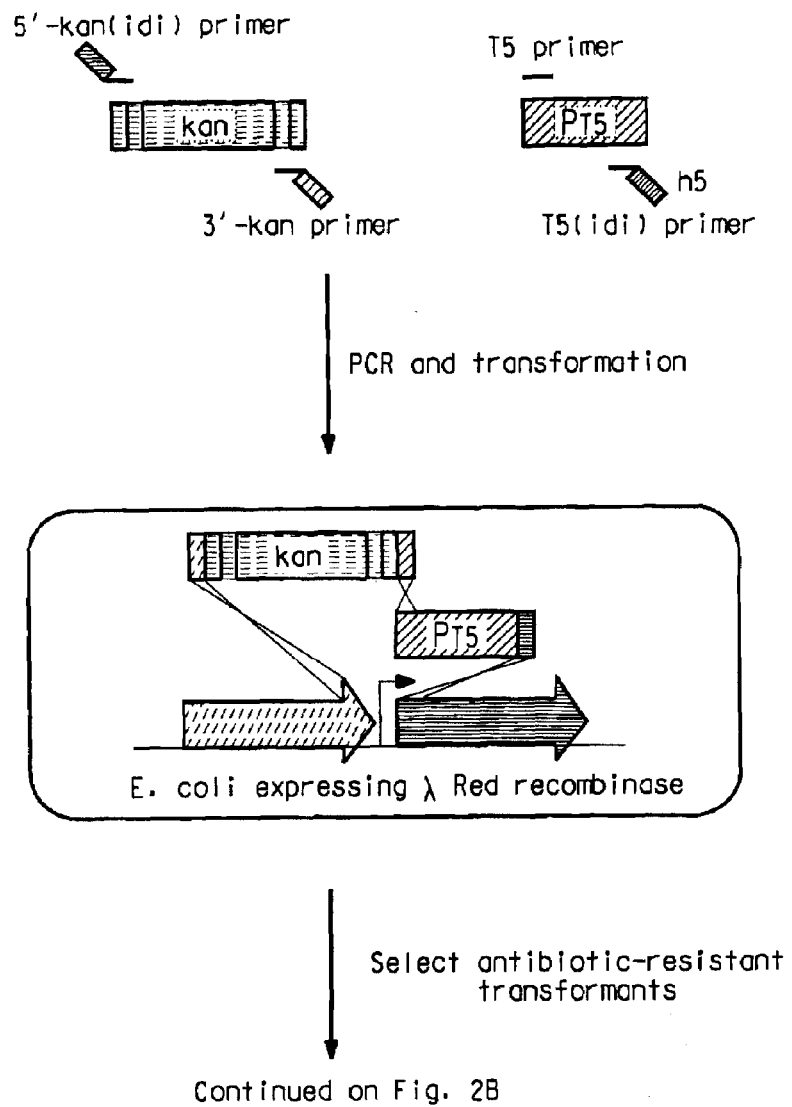

Continued from Fig. 2A

Eliminate antibiotic resistant marker using a FLP expression plasmid

E. coli expressing FLP

```
CORN-OLEOSIN-P21641        -----MADRDRSGIYGGAHATYGQQQQQ-GGGGRPM--GEQVKKGMLHDK
BARLEY-OLEOSIN-S57778      --------MAERGSYVQVQHGGQYGAGQQ-QHGRGQM--GEQMKG-MLQEK
OLEA-OLEOSIN-AAL92479      --------MAERDRPQPHQVQVHTQSR------YDQ--GGGMKS-VLPKK
THEOBROMA-OLEOSIN-AAM46777 --------MADRDRPHQIQVHQHHR-------FDQ--GGKNYQ-SA--S
CARROT-OLEOSIN-JQ0986      ---------MAERGTYAHQVQVHPQQT------ANQ--PGGVKS-LLPKN
PERILLA-OLEOSIN-AAG24455   -------MADRDRDRDRLHPHQIQVHPQ-HPGQHRY--EGGAKS-LLPQK
ARACHIS-OLEOSIN-AAK13450   ---MATATDRAPHQVQVHTPTTQRVDVQ-RRGYDVS--GGGVKT-FLPDR
ARABIDOPSIS-OLEOSIN-NP198858 -MADTHRVDRTDRHFQFQSPYEGGRGQGQYEGDRGY--GGGGYKSMMPES
HELIANTHUS-OLEOSIN-S60482  ---MATTYDRHHVTTTQPQYRHD------QHT--GDRLTHPQRHEQ
GLYCINE-OLEOSIN-P29530     -MTTQVPPHSVQVHTTTHRYEAGVVPPGARFETSYEAGVKAASIYHSER
PRUNUS-OLEOSIN-S51940      ----------------------------------MADQHFQQPLHFQGSYGQQ
CORYLUS-OLEOSIN-AAO65960   -----------------------------------MAEHPRQLQDPAH
SESAMUM-OLEOSIN-AAD42942   --------------------------MAEHYGQQQTRAPHLQL
BRASSICA-OLEOSIN-P29110    MTDTARTHHDITSRDQYPRDRDQYSMIGRDRDQYSMMGRDRDQYNMYGRD
```

FIG. 3A

```
CORN-OLEOSIN-P21641              GPTASQALTVATLFPLGGLLLVLSGLALTASVVGLAVATPVFLIFSPVLV
BARLEY-OLEOSIN-S57778            APSASQALTVATLFPLGGLLLVLSGVALAGTVVGLAVATPVFLLFSPVLV
OLEA-OLEOSIN-AAL92479            GPSTSQVLAVVTLLPVGGTLLALAGLTLVESLIGLAVTTPLFIIFSPVLV
THEOBROMA-OLEOSIN-AAM46777       GPSATQVLAVLTLLPVGGILLALAGLTLTGTVIGLCVATPLFIIFSPVLV
CARROT-OLEOSIN-JQ0986            SPSTSQVLAVVTLLPVGGTLLFLAGITLVGTLIGLAVATPLFLLFSPVLV
PERILLA-OLEOSIN-AAG24455         GPSTGQILAITLLPIGGTLLCLAGITLAGSLIGLAFATPLFVIFSPVLV
ARACHIS-OLEOSIN-AAK13450         GPSTSQIIAVLVGVPTGGTLLLLSGLSLLGTIIGLAIATPVFTFFSPVIV
ARABIDOPSIS-OLEOSIN-NP198858     GPSSTQVLSLLIGVPVVGSLLALAGLLLAGSVIGLMVALPLFLLFSPVIV
HELIANTHUS-OLEOSIN-S60482        GPSTGKIMVIMALLPITGILFGLAGITLVGTVIGLPLATPLFVIFSPVIV
GLYCINE-OLEOSIN-P29530           GPTTSQVLAVLAGLPVGGILLLLAGLTLAGTLTGLAVATPLFVLFSPVLV
PRUNUS-OLEOSIN-S51940            QPRSYQVAKAATAVTAGGSLLVLSGLVLAGTVIALTIATPLFVIFSPVLV
CORYLUS-OLEOSIN-AAO65960         QPRSHQVVKAATAATAGGSLLVPSGLILAGTVIALTLATPLFVIFSPVLV
SESAMUM-OLEOSIN-AAD42942         QPRAQRVVKAATAVTAGGSLLVLSGLTLAGTVIALTIATPLLVIFSPVLV
BRASSICA-OLEOSIN-P29110          YSKSRQIAKAVTAVTAGGSLLVLSSLTLVGTVIALTVATPLLVIFSPILV
                                                 G  L        L      L      P      FSP
```

FIG. 3B

```
CORN-OLEOSIN-P21641            PAALLIGTAVMGFLTSGALGLGLSSLTCLANTARQAFQRTP-DYVEEAR
BARLEY-OLEOSIN-S57778          PAALTIGMAVTGFLASGALGLGLSSLTVLANTARQAFQRTP-DYVEEAR
OLEA-OLEOSIN-AAL92479          PATILVGLAVTAFLTSGAFGLTGLSSLSWVVNFLRQVSGS----MLDLAK
THEOBROMA-OLEOSIN-AAM46777     PAAIAVGLAVAGFLSSGAFGLTGLSSLAYVFNRLRRATGTEQ-LDMDQAK
CARROT-OLEOSIN-JQ0986          PAALTIGLAVTGFLGSGAFGLTGLSSLSWVLSYFRQASQRVP-DQIELAK
PERILLA-OLEOSIN-AAG24455       PAAFLLALAVTAFLTSGAFGLTGLSSLSWVFNSFRQAT--GQ-EPLDYAK
ARACHIS-OLEOSIN-AAK13450       PAVVTIGLAVIGILTAGACGLTGLMSLSWMINFIRQVHGTTVPDQLDSAK
ARABIDOPSIS-OLEOSIN-NP198858   PAALTIGLAMTGFLASGMFGLTGLSSISWVMNYLRGTRRTVP-EQLEYAK
HELIANTHUS-OLEOSIN-S60482      PAMIAIGLAVTGFLTSGTFGLTGFLTGLSSLSYLFNMVRRSTMSVP-DQMDYVK
GLYCINE-OLEOSIN-P29530         PATVAIGLAVAGFLTSGAFGLTALSSFSWILNYIRETQPASE-NLAAAAK
PRUNUS-OLEOSIN-S51940          PALITVALITMGFLTSGGFGVAAVTVLSWIYKYVTGKQPPGA-DQLDQAR
CORYLUS-OLEOSIN-AAO65960       PAVITVSLIIMGFLASGGFGVAAVTVLSWIYRYVTGRHPPGA-DQLDHAR
SESAMUM-OLEOSIN-AAD42942       PAVITIFLLGAGFLASGGFGVAALSVLSWIYRYLTGKHPPGA-DQLESAK
BRASSICA-OLEOSIN-P29110        PALITVAMLITGFLSSGGFGIAAITVFSWIYKYATGEHPQGS-DKLDSAR
                               PA          L    G   G
```

FIG. 3C

| | |
|---|---|
| CORN-OLEOSIN-P21641 | RRMAEAAAQAGHKTAQAGQAIQGRAQEAGTGGGAGAGAGGGRASS------ |
| BARLEY-OLEOSIN-S57778 | QRMADAAAAAGHKTQQAGHAIQSRAEETRAGHTAGAGAGAGTRASS------ |
| OLEA-OLEOSIN-AAL92479 | SRMGDAAIQVGQKTKETGQTIQQKAPEGKESTGGRT-------------- |
| THEOBROMA-OLEOSIN-AAM46777 | RRMQDMAGYVGQKTKEVGQKIEGKANEGTVRT----------------- |
| CARROT-OLEOSIN-JQ0986 | KRAQEMAAYAGQKTKEVGDTIQSKAAQADTTATTGRDTRSTARDTSRT- |
| PERILLA-OLEOSIN-AAG24455 | RRMQEGTMYVGEKTKQVGETIKSKAQEGGHDDRTTVLG-GRT------- |
| ARACHIS-OLEOSIN-AAK13450 | RRMADMADYVGQKTKDAGQEIQTKAQDVKRSSS---------------- |
| ARABIDOPSIS-OLEOSIN-NP198858 | RRMADAVGYAGQKGKEMGQHVQNKAQDVKQYDISKPHDTTTKGHETQGRT |
| HELIANTHUS-OLEOSIN-S60482 | GKLQDVGEYTGQKTKDLGQKIQHTAHEMGDQGQGQGGGKEGRKEGGK- |
| GLYCINE-OLEOSIN-P29530 | HHLAEAAEYVGQKTKEVGQKTKEVGQDIQSKAQDTREAAARDAREAAARD |
| PRUNUS-OLEOSIN-S51940 | HKLAGKARDIKDRAEQFGQQHVPSGQQQGSS----------------- |
| CORYLUS-OLEOSIN-AAO65960 | MKLASKAREMKDRAEQFGQQHVTGSQGS-------------------- |
| SESAMUM-OLEOSIN-AAD42942 | TKLASKAREMKDRAEQFSQQPVAGSQTS-------------------- |
| BRASSICA-OLEOSIN-P29110 | MKLGSKAQDLKDRAQYYGQQHTGGEHDRDRTRGTQHTT---- |

FIG. 3D

```
CORN-OLEOSIN-P21641                   -------------------------
BARLEY-OLEOSIN-S57778                 -------------------------
OLEA-OLEOSIN-AAL92479                 -------------------------
THEOBROMA-OLEOSIN-AAM46777            -------------------------
CARROT-OLEOSIN-JQ0986                 -------------------------
PERILLA-OLEOSIN-AAG24455              -------------------------
ARACHIS-OLEOSIN-AAK13450              -------------------------
ARABIDOPSIS-OLEOSIN-NP198858          TAA----------------------
HELIANTHUS-OLEOSIN-S60482             -------------------------
GLYCINE-OLEOSIN-P29530                AREAAARDAKVEARDVKRTTVTATTATA
PRUNUS-OLEOSIN-S51940                 -------------------------
CORYLUS-OLEOSIN-AAO65960              -------------------------
SESAMUM-OLEOSIN-AAD42942              -------------------------
BRASSICA-OLEOSIN-P29110               -------------------------
```

FIG. 3E

SEQUENCE LISTING

<160> NUMBER OF SEQ ID NOS: 72

<210> SEQ ID NO 1
<211> LENGTH: 912
<212> TYPE: DNA
<213> ORGANISM: Pantoea stewartii

<400> SEQUENCE: 1

```
ttgacggtct gcgcaaaaaa acacgttcac cttactggca tttcggctga gcagttgctg      60
gctgatatcg atagccgcct tgatcagtta ctgccggttc agggtgagcg ggattgtgtg     120
ggtgccgcga tgcgtgaagg cacgctggca ccgggcaaac gtattcgtcc gatgctgctg     180
ttattaacag cgcgcgatct tggctgtgcg atcagtcacg ggggattact ggatttagcc     240
tgcgcggttg aaatggtgca tgctgcctcg ctgattctgg atgatatgcc ctgcatggac     300
gatgcgcaga tgcgtcgggg gcgtcccacc attcacacgc agtacggtga acatgtggcg     360
attctggcgg cggtcgcttt actcagcaaa gcgtttgggg tgattgccga ggctgaaggt     420
```

```
                                                -continued
ctgacgccga tagccaaaac tcgcgcggtg tcggagctgt ccactgcgat tggcatgcag    480
ggtctggttc agggccagtt taaggacctc tcggaaggcg ataaacccg cagcgccgat     540 gccatactgc taaccaatca gtttaaaacc agcacgctgt tttgcgcgtc aacgcaaatg    600
gcgtccattg cggccaacgc gtcctgcgaa gcgcgtgaga acctgcatcg tttctcgctc    660
gatctcggcc aggcctttca gttgcttgac gatcttaccg atggcatgac cgataccggc    720
aaagacatca atcaggatgc aggtaaatca acgctggtca atttattagg ctcaggcgcg    780
gtcgaagaac gcctgcgaca gcatttgcgc ctggccagtg aacacctttc gcggcatgc     840 caaaacggcc attccaccac ccaactttttt attcaggcct ggtttgacaa aaaactcgct   900
gccgtcagtt aa                                                        912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
1               5                   10                  15

Glu Gln Leu Leu Ala Asp Ile Asp Ser Arg Leu Asp Gln Leu Leu Pro
            20                  25                  30

Val Gln Gly Glu Arg Asp Cys Val Gly Ala Ala Met Arg Glu Gly Thr
        35                  40                  45

Leu Ala Pro Gly Lys Arg Ile Arg Pro Met Leu Leu Leu Thr Ala
    50                  55                  60

Arg Asp Leu Gly Cys Ala Ile Ser His Gly Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
            100                 105                 110

Thr Gln Tyr Gly Glu His Val Ala Ile Leu Ala Ala Val Ala Leu Leu
        115                 120                 125

Ser Lys Ala Phe Gly Val Ile Ala Glu Ala Glu Gly Leu Thr Pro Ile
    130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
                165                 170                 175

Arg Ser Ala Asp Ala Ile Leu Leu Thr Asn Gln Phe Lys Thr Ser Thr
            180                 185                 190

Leu Phe Cys Ala Ser Thr Gln Met Ala Ser Ile Ala Ala Asn Ala Ser
        195                 200                 205

Cys Glu Ala Arg Glu Asn Leu His Arg Phe Ser Leu Asp Leu Gly Gln
    210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
                245                 250                 255

Gly Ser Gly Ala Val Glu Glu Arg Leu Arg Gln His Leu Arg Leu Ala
            260                 265                 270

Ser Glu His Leu Ser Ala Ala Cys Gln Asn Gly His Ser Thr Thr Gln
        275                 280                 285
```

```
Leu Phe Ile Gln Ala Trp Phe Asp Lys Lys Leu Ala Ala Val Ser
    290                 295                 300
```

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3

```
atg agc cat ttt gcg gtg atc gca ccg ccc ttt ttc agc cat gtt cgc        48
Met Ser His Phe Ala Val Ile Ala Pro Pro Phe Phe Ser His Val Arg
1               5                   10                  15 gct ctg caa aac ctt gct cag gaa tta gtg gcc cgc ggt cat cgt gtt        96
Ala Leu Gln Asn Leu Ala Gln Glu Leu Val Ala Arg Gly His Arg Val
                20                  25                  30 acg ttt ttt cag caa cat gac tgc aaa gcg ctg gta acg ggc agc gat       144
Thr Phe Phe Gln Gln His Asp Cys Lys Ala Leu Val Thr Gly Ser Asp
            35                  40                  45 atc gga ttc cag acc gtc gga ctg caa acg cat cct ccc ggt tcc tta       192
Ile Gly Phe Gln Thr Val Gly Leu Gln Thr His Pro Pro Gly Ser Leu
        50                  55                  60 tcg cac ctg ctg cac ctg gcc gcg cac cca ctc gga ccc tcg atg tta       240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa       288
Arg Leu Ile Asn Glu Met Ala Arg Thr Ser Asp Met Leu Cys Arg Glu
                85                  90                  95 ctg ccc gcc gct ttt cat gcg ttg cag ata gag ggc gtg atc gtt gat       336
Leu Pro Ala Ala Phe His Ala Leu Gln Ile Glu Gly Val Ile Val Asp
                100                 105                 110 caa atg gag ccg gca ggt gca gta gtc gca gaa gcg tca ggt ctg ccg       384
Gln Met Glu Pro Ala Gly Ala Val Val Ala Glu Ala Ser Gly Leu Pro
            115                 120                 125 ttt gtt tcg gtg gcc tgc gcg ctg ccg ctc aac cgc gaa ccg ggt ttg       432
Phe Val Ser Val Ala Cys Ala Leu Pro Leu Asn Arg Glu Pro Gly Leu
        130                 135                 140 cct ctg gcg gtg atg cct ttc gag tac ggc acc agc gat gcg gct cgg       480
Pro Leu Ala Val Met Pro Phe Glu Tyr Gly Thr Ser Asp Ala Ala Arg
145                 150                 155                 160 gaa cgc tat acc acc agc gaa aaa att tat gac tgg ctg atg cga cgt       528
Glu Arg Tyr Thr Thr Ser Glu Lys Ile Tyr Asp Trp Leu Met Arg Arg
                165                 170                 175 cac gat cgt gtg atc gcg cat cat gca tgc aga atg ggt tta gcc ccg       576
His Asp Arg Val Ile Ala His His Ala Cys Arg Met Gly Leu Ala Pro
                180                 185                 190 cgt gaa aaa ctg cat cat tgt ttt tct cca ctg gca caa atc agc cag       624
Arg Glu Lys Leu His His Cys Phe Ser Pro Leu Ala Gln Ile Ser Gln
            195                 200                 205 ttg atc ccc gaa ctg gat ttt ccc cgc aaa gcg ctg cca gac tgc ttt       672
Leu Ile Pro Glu Leu Asp Phe Pro Arg Lys Ala Leu Pro Asp Cys Phe
        210                 215                 220 cat gcg gtt gga ccg tta cgg caa ccc cag ggg acg ccg ggg tca tca       720
His Ala Val Gly Pro Leu Arg Gln Pro Gln Gly Thr Pro Gly Ser Ser
225                 230                 235                 240 act tct tat ttt ccg tcc ccg gac aaa ccc cgt att ttt gcc tcg ctg       768
Thr Ser Tyr Phe Pro Ser Pro Asp Lys Pro Arg Ile Phe Ala Ser Leu
                245                 250                 255
```

```
ggc acc ctg cag gga cat cgt tat ggc ctg ttc agg acc atc gcc aaa      816
Gly Thr Leu Gln Gly His Arg Tyr Gly Leu Phe Arg Thr Ile Ala Lys
        260                 265                 270 gcc tgc gaa gag gtg gat gcg cag tta ctg ttg gca cac tgt ggc ggc      864
Ala Cys Glu Glu Val Asp Ala Gln Leu Leu Leu Ala His Cys Gly Gly
    275                 280                 285 ctc tca gcc acg cag gca ggt gaa ctg gcc cgg ggc ggg gac att cag      912
Leu Ser Ala Thr Gln Ala Gly Glu Leu Ala Arg Gly Gly Asp Ile Gln
290                 295                 300 gtt gtg gat ttt gcc gat caa tcc gca gca ctt tca cag gca cag ttg      960
Val Val Asp Phe Ala Asp Gln Ser Ala Ala Leu Ser Gln Ala Gln Leu
305                 310                 315                 320 aca atc aca cat ggt ggg atg aat acg gta ctg gac gct att gct tcc     1008
Thr Ile Thr His Gly Gly Met Asn Thr Val Leu Asp Ala Ile Ala Ser
            325                 330                 335 cgc aca ccg cta ctg gcg ctg ccg ctg gca ttt gat caa cct ggc gtg     1056
Arg Thr Pro Leu Leu Ala Leu Pro Leu Ala Phe Asp Gln Pro Gly Val
        340                 345                 350 gca tca cga att gtt tat cat ggc atc ggc aag cgt gcg tct cgg ttt     1104
Ala Ser Arg Ile Val Tyr His Gly Ile Gly Lys Arg Ala Ser Arg Phe
    355                 360                 365 act acc agc cat gcg ctg gcg cgg cag att cga tcg ctg ctg act aac     1152
Thr Thr Ser His Ala Leu Ala Arg Gln Ile Arg Ser Leu Leu Thr Asn
370                 375                 380 acc gat tac ccg cag cgt atg aca aaa att cag gcc gca ttg cgt ctg     1200
Thr Asp Tyr Pro Gln Arg Met Thr Lys Ile Gln Ala Ala Leu Arg Leu
385                 390                 395                 400 gca ggc ggc aca cca gcc gcc gcc gat att gtt gaa cag gcg atg cgg     1248
Ala Gly Gly Thr Pro Ala Ala Ala Asp Ile Val Glu Gln Ala Met Arg
            405                 410                 415 acc tgt cag cca gta ctc agt ggg cag gat tat gca acc gca cta tga     1296
Thr Cys Gln Pro Val Leu Ser Gly Gln Asp Tyr Ala Thr Ala Leu
        420                 425                 430

<210> SEQ ID NO 4
<211> LENGTH: 431
<212> TYPE: PRT
<213> ORGANISM: Pantoea stewartii

<400> SEQUENCE: 4

Met Ser His Phe Ala Val Ile Ala Pro Pro Phe Phe Ser His Val Arg
1               5                   10                  15

Ala Leu Gln Asn Leu Ala Gln Glu Leu Val Ala Arg Gly His Arg Val
            20                  25                  30

Thr Phe Phe Gln Gln His Asp Cys Lys Ala Leu Val Thr Gly Ser Asp
        35                  40                  45

Ile Gly Phe Gln Thr Val Gly Leu Gln Thr His Pro Pro Gly Ser Leu
    50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Val Ala Glu Ala Ser Gly Leu Pro
        115                 120                 125

Phe Val Ser Val Ala Cys Ala Leu Pro Leu Asn Arg Glu Pro Gly Leu
    130                 135                 140
```

```
Pro Leu Ala Val Met Pro Phe Glu Tyr Gly Thr Ser Asp Ala Ala Arg
145                 150                 155                 160

Glu Arg Tyr Thr Thr Ser Glu Lys Ile Tyr Asp Trp Leu Met Arg Arg
                165                 170                 175

His Asp Arg Val Ile Ala His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
    210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
                245                 250                 255

Gly Thr Leu Gln Gly His Arg Tyr Gly Leu Phe Arg Thr Ile Ala Lys
            260                 265                 270

Ala Cys Glu Glu Val Asp Ala Gln Leu Leu Ala His Cys Gly Gly
        275                 280                 285

Leu Ser Ala Thr Gln Ala Gly Glu Leu Ala Arg Gly Gly Asp Ile Gln
290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
                325                 330                 335

Arg Thr Pro Leu Leu Ala Leu Pro Leu Ala Phe Asp Gln Pro Gly Val
            340                 345                 350

Ala Ser Arg Ile Val Tyr His Gly Ile Gly Lys Arg Ala Ser Arg Phe
        355                 360                 365

Thr Thr Ser His Ala Leu Ala Arg Gln Ile Arg Ser Leu Leu Thr Asn
    370                 375                 380

Thr Asp Tyr Pro Gln Arg Met Thr Lys Ile Gln Ala Ala Leu Arg Leu
385                 390                 395                 400

Ala Gly Gly Thr Pro Ala Ala Asp Ile Val Glu Gln Ala Met Arg
                405                 410                 415

Thr Cys Gln Pro Val Leu Ser Gly Gln Asp Tyr Ala Thr Ala Leu
            420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat        48
Met Gln Pro His Tyr Asp Leu Ile Leu Val Gly Ala Gly Leu Ala Asn
1               5                   10                  15 ggc ctt atc gcg ctc cgg ctt cag caa cag cat ccg gat atg cgg atc        96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc       144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg       192
Phe His Glu Glu Asp Leu Thr Leu Asn Gln His Arg Trp Ile Ala Pro
```

```
             50                    55                    60
ctt gtg gtc cat cac tgg ccc gac tac cag gtt cgt ttc ccc caa cgc      240
Leu Val Val His His Trp Pro Asp Tyr Gln Val Arg Phe Pro Gln Arg
 65              70                     75                   80 cgt cgc cat gtg aac agt ggc tac tac tgc gtg acc tcc cgg cat ttc      288
Arg Arg His Val Asn Ser Gly Tyr Tyr Cys Val Thr Ser Arg His Phe
                 85                      90                    95 gcc ggg ata ctc cgg caa cag ttt gga caa cat tta tgg ctg cat acc      336
Ala Gly Ile Leu Arg Gln Gln Phe Gly Gln His Leu Trp Leu His Thr
               100                    105                  110 gcg gtt tca gcc gtt cat gct gaa tcg gtc cag tta gcg gat ggc cgg      384
Ala Val Ser Ala Val His Ala Glu Ser Val Gln Leu Ala Asp Gly Arg
            115                    120                  125 att att cat gcc agt aca gtg atc gac gga cgg gtt tac acg cct gat      432
Ile Ile His Ala Ser Thr Val Ile Asp Gly Arg Val Tyr Thr Pro Asp
130                 135                    140 tct gca cta cgc gta gga ttc cag gca ttt atc ggt cag gag tgg caa      480
Ser Ala Leu Arg Val Gly Phe Gln Ala Phe Ile Gly Gln Glu Trp Gln
145                 150                    155                  160 ctg agc gcg ccg cat ggt tta tcg tca ccg att atc atg gat gcg acg      528
Leu Ser Ala Pro His Gly Leu Ser Ser Pro Ile Ile Met Asp Ala Thr
                165                    170                  175 gtc gat cag caa aat ggc tac cgc ttt gtt tat acc ctg ccg ctt tcc      576
Val Asp Gln Gln Asn Gly Tyr Arg Phe Val Tyr Thr Leu Pro Leu Ser
             180                    185                  190 gca acc gca ctg ctg atc gaa gac aca cac tac att gac aag gct aat      624
Ala Thr Ala Leu Leu Ile Glu Asp Thr His Tyr Ile Asp Lys Ala Asn
          195                    200                  205 ctt cag gcc gaa cgg gcg cgt cag aac att cgc gat tat gct gcg cga      672
Leu Gln Ala Glu Arg Ala Arg Gln Asn Ile Arg Asp Tyr Ala Ala Arg
        210                    215                  220 cag ggt tgg ccg tta cag acg ttg ctg cgg gaa gaa cag ggt gca ttg      720
Gln Gly Trp Pro Leu Gln Thr Leu Leu Arg Glu Glu Gln Gly Ala Leu
225                 230                    235                  240 ccc att acg tta acg ggc gat aat cgt cag ttt tgg caa cag caa ccg      768
Pro Ile Thr Leu Thr Gly Asp Asn Arg Gln Phe Trp Gln Gln Gln Pro
                245                    250                  255 caa gcc tgt agc gga tta cgc gcc ggg ctg ttt cat ccg aca acc ggc      816
Gln Ala Cys Ser Gly Leu Arg Ala Gly Leu Phe His Pro Thr Thr Gly
             260                    265                  270 tac tcc cta ccg ctc gcg gtg gcg ctg gcc gat cgt ctc agc gcg ctg      864
Tyr Ser Leu Pro Leu Ala Val Ala Leu Ala Asp Arg Leu Ser Ala Leu
          275                    280                  285 gat gtg ttt acc tct tcc tct gtt cac cag acg att gct cac ttt gcc      912
Asp Val Phe Thr Ser Ser Ser Val His Gln Thr Ile Ala His Phe Ala
        290                    295                  300 cag caa cgt tgg cag caa cag ggg ttt ttc cgc atg ctg aat cgc atg      960
Gln Gln Arg Trp Gln Gln Gln Gly Phe Phe Arg Met Leu Asn Arg Met
305                 310                    315                  320 ttg ttt tta gcc gga ccg gcc gag tca cgc tgg cgt gtg atg cag cgt     1008
Leu Phe Leu Ala Gly Pro Ala Glu Ser Arg Trp Arg Val Met Gln Arg
                325                    330                  335 ttc tat ggc tta ccc gag gat ttg att gcc cgc ttt atg gcg gga aaa     1056
Phe Tyr Gly Leu Pro Glu Asp Leu Ile Ala Arg Phe Tyr Ala Gly Lys
             340                    345                  350 ctc acc gtg acc gat cgg cta cgc att ctg agc ggc aag ccg ccc gtt     1104
Leu Thr Val Thr Asp Arg Leu Arg Ile Leu Ser Gly Lys Pro Pro Val
          355                    360                  365 ccc gtt ttc gcg gca ttg cag gca att atg acg act cat cgt tga         1149
Pro Val Phe Ala Ala Leu Gln Ala Ile Met Thr Thr His Arg
```

```
Pro Val Phe Ala Ala Leu Gln Ala Ile Met Thr Thr His Arg
    370                 375                 380
```

<210> SEQ ID NO 6
<211> LENGTH: 382
<212> TYPE: PRT
<213> ORGANISM: Pantoea stewartii

<400> SEQUENCE: 6

```
Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile
            20                  25                  30

Leu Leu Ile Glu Ala Gly Pro Glu Ala Gly Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
65                  70                  75                  80

Arg Arg His Val Asn Ser Gly Tyr Tyr Cys Val Thr Ser Arg His Phe
                85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
        115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190

Ala Thr Ala Leu Leu Ile Glu Asp Thr His Tyr Ile Asp Lys Ala Asn
        195                 200                 205

Leu Gln Ala Glu Arg Ala Arg Gln Asn Ile Arg Asp Tyr Ala Ala Arg
    210                 215                 220

Gln Gly Trp Pro Leu Gln Thr Leu Leu Arg Glu Glu Gln Gly Ala Leu
225                 230                 235                 240

Pro Ile Thr Leu Thr Gly Asp Asn Arg Gln Phe Trp Gln Gln Pro
                245                 250                 255

Gln Ala Cys Ser Gly Leu Arg Ala Gly Leu Phe His Pro Thr Thr Gly
            260                 265                 270

Tyr Ser Leu Pro Leu Ala Val Ala Leu Ala Asp Arg Leu Ser Ala Leu
        275                 280                 285

Asp Val Phe Thr Ser Ser Val His Gln Thr Ile Ala His Phe Ala
    290                 295                 300

Gln Gln Arg Trp Gln Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Val Thr Asp Arg Leu Arg Ile Leu Ser Gly Lys Pro Pro Val
        355                 360                 365
```

```
Pro Val Phe Ala Ala Leu Gln Ala Ile Met Thr Thr His Arg
    370                 375                 380

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7 atg aaa cca act acg gta att ggt gcg ggc ttt ggt ggc ctg gca ctg        48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag        96
Ala Ile Arg Leu Gln Ala Ala Gly Ile Pro Val Leu Leu Leu Glu Gln
                20                  25                  30 cgc gac aag ccg ggt ggc cgg gct tat gtt tat cag gag cag ggc ttt       144
Arg Asp Lys Pro Gly Gly Arg Ala Tyr Val Tyr Gln Glu Gln Gly Phe
            35                  40                  45 act ttt gat gca ggc cct acc gtt atc acc gat ccc agc gcg att gaa       192
Thr Phe Asp Ala Gly Pro Thr Val Ile Thr Asp Pro Ser Ala Ile Glu
        50                  55                  60 gaa ctg ttt gct ctg gcc ggt aaa cag ctt aag gat tac gtc gag ctg       240
Glu Leu Phe Ala Leu Ala Gly Lys Gln Leu Lys Asp Tyr Val Glu Leu
65                  70                  75                  80 ttg ccg gtc acg ccg ttt tat cgc ctg tgc tgg gag tcc ggc aag gtc       288
Leu Pro Val Thr Pro Phe Tyr Arg Leu Cys Trp Glu Ser Gly Lys Val
                85                  90                  95 ttc aat tac gat aac gac cag gcc cag tta gaa gcg cag ata cag cag       336
Phe Asn Tyr Asp Asn Asp Gln Ala Gln Leu Glu Ala Gln Ile Gln Gln
            100                 105                 110 ttt aat ccg cgc gat gtt gcg ggt tat cga gcg ttc ctt gac tat tcg       384
Phe Asn Pro Arg Asp Val Ala Gly Tyr Arg Ala Phe Leu Asp Tyr Ser
        115                 120                 125 cgt gcc gta ttc aat gag ggc tat ctg aag ctc ggc act gtg cct ttt       432
Arg Ala Val Phe Asn Glu Gly Tyr Leu Lys Leu Gly Thr Val Pro Phe
    130                 135                 140 tta tcg ttc aaa gac atg ctt cgg gcc gcg ccc cag ttg gca aag ctg       480
Leu Ser Phe Lys Asp Met Leu Arg Ala Ala Pro Gln Leu Ala Lys Leu
145                 150                 155                 160 cag gca tgg cgc agc gtt tac agt aaa gtt gcc ggc tac att gag gat       528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg       576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa       624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc       672
Arg Glu Trp Gly Val Trp Phe Pro Arg Gly Gly Thr Gly Ala Leu Val
    210                 215                 220 aat ggc atg atc aag ctg ttt cag gat ctg ggc ggc gaa gtc gtg ctt       720
Asn Gly Met Ile Lys Leu Phe Gln Asp Leu Gly Gly Glu Val Val Leu
225                 230                 235                 240 aac gcc cgg gtc agt cat atg gaa acc gtt ggg gac aag att cag gcc       768
Asn Ala Arg Val Ser His Met Glu Thr Val Gly Asp Lys Ile Gln Ala
                245                 250                 255
```

| | | |
|---|---|---|
| gtg cag ttg gaa gac ggc aga cgg ttt gaa acc tgc gcg gtg gcg tcg<br>Val Gln Leu Glu Asp Gly Arg Arg Phe Glu Thr Cys Ala Val Ala Ser<br>260 265 270 | | 816 |
| aac gct gat gtt gta cat acc tat cgc gat ctg ctg tct cag cat ccc<br>Asn Ala Asp Val Val His Thr Tyr Arg Asp Leu Leu Ser Gln His Pro<br>275 280 285 | | 864 |
| gca gcc gct aag cag gcg aaa aaa ctg caa tcc aag cgt atg agt aac<br>Ala Ala Ala Lys Gln Ala Lys Lys Leu Gln Ser Lys Arg Met Ser Asn<br>290 295 300 | | 912 |
| tca ctg ttt gta ctc tat ttt ggt ctc aac cat cat cac gat caa ctc<br>Ser Leu Phe Val Leu Tyr Phe Gly Leu Asn His His His Asp Gln Leu<br>305 310 315 320 | | 960 |
| gcc cat cat acc gtc tgt ttt ggg cca cgc tac cgt gaa ctg att cac<br>Ala His His Thr Val Cys Phe Gly Pro Arg Tyr Arg Glu Leu Ile His<br>325 330 335 | | 1008 |
| gaa att ttt aac cat gat ggt ctg gct gag gat ttt tcg ctt tat tta<br>Glu Ile Phe Asn His Asp Gly Leu Ala Glu Asp Phe Ser Leu Tyr Leu<br>340 345 350 | | 1056 |
| cac gca cct tgt gtc acg gat ccg tca ctg gca ccg gaa ggg tgc ggc<br>His Ala Pro Cys Val Thr Asp Pro Ser Leu Ala Pro Glu Gly Cys Gly<br>355 360 365 | | 1104 |
| agc tat tat gtg ctg gcg cct gtt cca cac tta ggc acg gcg aac ctc<br>Ser Tyr Tyr Val Leu Ala Pro Val Pro His Leu Gly Thr Ala Asn Leu<br>370 375 380 | | 1152 |
| gac tgg gcg gta gaa gga ccc cga ctg cgc gat cgt att ttt gac tac<br>Asp Trp Ala Val Glu Gly Pro Arg Leu Arg Asp Arg Ile Phe Asp Tyr<br>385 390 395 400 | | 1200 |
| ctt gag caa cat tac atg cct ggc ttg cga agc cag ttg gtg acg cac<br>Leu Glu Gln His Tyr Met Pro Gly Leu Arg Ser Gln Leu Val Thr His<br>405 410 415 | | 1248 |
| cgt atg ttt acg ccg ttc gat ttc cgc gac gag ctc aat gcc tgg caa<br>Arg Met Phe Thr Pro Phe Asp Phe Arg Asp Glu Leu Asn Ala Trp Gln<br>420 425 430 | | 1296 |
| ggt tcg gcc ttc tcg gtt gaa cct att ctg acc cag agc gcc tgg ttc<br>Gly Ser Ala Phe Ser Val Glu Pro Ile Leu Thr Gln Ser Ala Trp Phe<br>435 440 445 | | 1344 |
| cga cca cat aac cgc gat aag cac att gat aat ctt tat ctg gtt ggc<br>Arg Pro His Asn Arg Asp Lys His Ile Asp Asn Leu Tyr Leu Val Gly<br>450 455 460 | | 1392 |
| gca ggc acc cat cct ggc gcg ggc att ccc ggc gta atc ggc tcg gcg<br>Ala Gly Thr His Pro Gly Ala Gly Ile Pro Gly Val Ile Gly Ser Ala<br>465 470 475 480 | | 1440 |
| aag gcg acg gca ggc tta atg ctg gag gac ctg att tga<br>Lys Ala Thr Ala Gly Leu Met Leu Glu Asp Leu Ile<br>485 490 | | 1479 |

<210> SEQ ID NO 8
<211> LENGTH: 492
<212> TYPE: PRT
<213> ORGANISM: Pantoea stewartii

<400> SEQUENCE: 8

Met Lys Pro Thr Thr Val Ile Gly Ala Gly Phe Gly Gly Leu Ala Leu
1               5                  10                 15

Ala Ile Arg Leu Gln Ala Ala Gly Ile Pro Val Leu Leu Glu Gln
    20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

```
Glu Leu Phe Ala Leu Ala Gly Lys Gln Leu Lys Asp Tyr Val Glu Leu
 65                  70                  75                  80

Leu Pro Val Thr Pro Phe Tyr Arg Leu Cys Trp Ser Gly Lys Val
                 85                  90                  95

Phe Asn Tyr Asp Asn Asp Gln Ala Gln Leu Glu Ala Gln Ile Gln Gln
                100                 105                 110

Phe Asn Pro Arg Asp Val Ala Gly Tyr Arg Ala Phe Leu Asp Tyr Ser
                115                 120                 125

Arg Ala Val Phe Asn Glu Gly Tyr Leu Lys Leu Gly Thr Val Pro Phe
            130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
                180                 185                 190

Asn Pro Phe Ala Thr Ser Ser Ile Tyr Thr Leu Ile His Ala Leu Glu
            195                 200                 205

Arg Glu Trp Gly Val Trp Phe Pro Arg Gly Gly Thr Gly Ala Leu Val
            210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
            260                 265                 270

Asn Ala Asp Val Val His Thr Tyr Arg Asp Leu Leu Ser Gln His Pro
            275                 280                 285

Ala Ala Ala Lys Gln Ala Lys Lys Leu Gln Ser Lys Arg Met Ser Asn
            290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile His
                325                 330                 335

Glu Ile Phe Asn His Asp Gly Leu Ala Glu Asp Phe Ser Leu Tyr Leu
                340                 345                 350

His Ala Pro Cys Val Thr Asp Pro Ser Leu Ala Pro Glu Gly Cys Gly
            355                 360                 365

Ser Tyr Tyr Val Leu Ala Pro Val Pro His Leu Gly Thr Ala Asn Leu
    370                 375                 380

Asp Trp Ala Val Glu Gly Pro Arg Leu Arg Asp Arg Ile Phe Asp Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Glu Leu Asn Ala Trp Gln
                420                 425                 430

Gly Ser Ala Phe Ser Val Glu Pro Ile Leu Thr Gln Ser Ala Trp Phe
            435                 440                 445

Arg Pro His Asn Arg Asp Lys His Ile Asp Asn Leu Tyr Leu Val Gly
            450                 455                 460

Ala Gly Thr His Pro Gly Ala Gly Ile Pro Gly Val Ile Gly Ser Ala
465                 470                 475                 480
```

```
                Lys Ala Thr Ala Gly Leu Met Leu Glu Asp Leu Ile
                                485                 490
```

<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9

```
atg gcg gtt ggc tcg aaa agc ttt gcg act gca tcg acg ctt ttc gac      48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac      96
Ala Lys Thr Arg Arg Ser Val Leu Met Leu Tyr Ala Trp Cys Arg His
                20                  25                  30 tgc gac gac gtc att gac gat caa aca ctg ggc ttt cat gcc gac cag     144
Cys Asp Asp Val Ile Asp Asp Gln Thr Leu Gly Phe His Ala Asp Gln
            35                  40                  45 ccc tct tcg cag atg cct gag cag cgc ctg cag cag ctt gaa atg aaa     192
Pro Ser Ser Gln Met Pro Glu Gln Arg Leu Gln Gln Leu Glu Met Lys
        50                  55                  60 acg cgt cag gcc tac gcc ggt tcg caa atg cac gag ccc gct ttt gcc     240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg     288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac     336
Phe Asp His Leu Glu Gly Phe Ala Met Asp Val Arg Glu Thr Arg Tyr
                100                 105                 110 ctg aca ctg gac gat acg ctg cgt tat tgc tat cac gtc gcc ggt gtt     384
Leu Thr Leu Asp Asp Thr Leu Arg Tyr Cys Tyr His Val Ala Gly Val
            115                 120                 125 gtg ggc ctg atg atg gcg caa att atg ggc gtt cgc gat aac gcc acg     432
Val Gly Leu Met Met Ala Gln Ile Met Gly Val Arg Asp Asn Ala Thr
        130                 135                 140 ctc gat cgc gcc tgc gat ctc ggg ctg gct ttc cag ttg acc aac att     480
Leu Asp Arg Ala Cys Asp Leu Gly Leu Ala Phe Gln Leu Thr Asn Ile
145                 150                 155                 160 gcg cgt gat att gtc gac gat gct cag gtg ggc cgc tgt tat ctg cct     528
Ala Arg Asp Ile Val Asp Asp Ala Gln Val Gly Arg Cys Tyr Leu Pro
                165                 170                 175 gaa agc tgg ctg gaa gag gaa gga ctg acg aaa gcg aat tat gct gcg     576
Glu Ser Trp Leu Glu Glu Glu Gly Leu Thr Lys Ala Asn Tyr Ala Ala
                180                 185                 190 cca gaa aac cgg cag gcc tta agc cgt atc gcc ggg cga ctg gta cgg     624
Pro Glu Asn Arg Gln Ala Leu Ser Arg Ile Ala Gly Arg Leu Val Arg
            195                 200                 205 gaa gcg gaa ccc tat tac gta tca tca atg gcc ggt ctg gca caa tta     672
Glu Ala Glu Pro Tyr Tyr Val Ser Ser Met Ala Gly Leu Ala Gln Leu
        210                 215                 220 ccc tta cgc tcg gcc tgg gcc atc gcg aca gcg aag cag gtg tac cgt     720
Pro Leu Arg Ser Ala Trp Ala Ile Ala Thr Ala Lys Gln Val Tyr Arg
225                 230                 235                 240 aaa att ggc gtg aaa gtt gaa cag gcc ggt aag cag gcc tgg gat cat     768
Lys Ile Gly Val Lys Val Glu Gln Ala Gly Lys Gln Ala Trp Asp His
                245                 250                 255 cgc cag tcc acg tcc acc gcc gaa aaa tta acg ctt ttg ctg acg gca     816
Arg Gln Ser Thr Ser Thr Ala Glu Lys Leu Thr Leu Leu Leu Thr Ala
```

```
Arg Gln Ser Thr Ser Thr Ala Glu Lys Leu Thr Leu Leu Thr Ala
            260                 265                 270 tcc ggt cag gca gtt act tcc cgg atg aag acg tat cca ccc cgt cct      864
Ser Gly Gln Ala Val Thr Ser Arg Met Lys Thr Tyr Pro Pro Arg Pro
            275                 280                 285 gct cat ctc tgg cag cgc ccg atc tag                                  891
Ala His Leu Trp Gln Arg Pro Ile
            290                 295

<210> SEQ ID NO 10
<211> LENGTH: 296
<212> TYPE: PRT
<213> ORGANISM: Pantoea stewartii

<400> SEQUENCE: 10

Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
            20                  25                  30

Cys Asp Val Ile Asp Asp Gln Thr Leu Gly Phe His Ala Asp Gln
        35                  40                  45

Pro Ser Ser Gln Met Pro Glu Gln Arg Leu Gln Gln Leu Glu Met Lys
    50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Thr Arg Tyr
            100                 105                 110

Leu Thr Leu Asp Asp Thr Leu Arg Tyr Cys Tyr His Val Ala Gly Val
        115                 120                 125

Val Gly Leu Met Met Ala Gln Ile Met Gly Val Arg Asp Asn Ala Thr
    130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala Gln Val Gly Arg Cys Tyr Leu Pro
                165                 170                 175

Glu Ser Trp Leu Glu Glu Gly Leu Thr Lys Ala Asn Tyr Ala Ala
            180                 185                 190

Pro Glu Asn Arg Gln Ala Leu Ser Arg Ile Ala Gly Arg Leu Val Arg
        195                 200                 205

Glu Ala Glu Pro Tyr Tyr Val Ser Ser Met Ala Gly Leu Ala Gln Leu
    210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Lys Gln Ala Trp Asp His
                245                 250                 255

Arg Gln Ser Thr Ser Thr Ala Glu Lys Leu Thr Leu Leu Thr Ala
            260                 265                 270

Ser Gly Gln Ala Val Thr Ser Arg Met Lys Thr Tyr Pro Pro Arg Pro
        275                 280                 285

Ala His Leu Trp Gln Arg Pro Ile
    290                 295

<210> SEQ ID NO 11
<211> LENGTH: 528
```

<212> TYPE: DNA
<213> ORGANISM: Pantoea stewartii
<220> FEATURE:
<221> NAME/KEY: CDS
<222> LOCATION: (1)..(528)

<400> SEQUENCE: 11

| | | | | | | | | | | | | | | | | |
|---|---|---|---|---|---|---|---|---|---|---|---|---|---|---|---|---|
| atg | ttg | tgg | att | tgg | aat | gcc | ctg | atc | gtg | ttt | gtc | acc | gtg | gtc | ggc | 48 |
| Met | Leu | Trp | Ile | Trp | Asn | Ala | Leu | Ile | Val | Phe | Val | Thr | Val | Val | Gly | |
| 1 | | | | 5 | | | | | 10 | | | | | 15 | | |

| atg | gaa | gtg | gtt | gct | gca | ctg | gca | cat | aaa | tac | atc | atg | cac | ggc | tgg | 96 |
|---|---|---|---|---|---|---|---|---|---|---|---|---|---|---|---|---|
| Met | Glu | Val | Val | Ala | Ala | Leu | Ala | His | Lys | Tyr | Ile | Met | His | Gly | Trp | |
| | | | 20 | | | | | 25 | | | | | 30 | | | |

| ggt | tgg | ggc | tgg | cat | ctt | tca | cat | cat | gaa | ccg | cgt | aaa | ggc | gca | ttt | 144 |
|---|---|---|---|---|---|---|---|---|---|---|---|---|---|---|---|---|
| Gly | Trp | Gly | Trp | His | Leu | Ser | His | His | Glu | Pro | Arg | Lys | Gly | Ala | Phe | |
| | | 35 | | | | | 40 | | | | | 45 | | | | |

| gaa | gtt | aac | gat | ctc | tat | gcc | gtg | gta | ttc | gcc | att | gtg | tcg | att | gcc | 192 |
|---|---|---|---|---|---|---|---|---|---|---|---|---|---|---|---|---|
| Glu | Val | Asn | Asp | Leu | Tyr | Ala | Val | Val | Phe | Ala | Ile | Val | Ser | Ile | Ala | |
| 50 | | | | | 55 | | | | | 60 | | | | | | |

| ctg | att | tac | ttc | ggc | agt | aca | gga | atc | tgg | ccg | ctc | cag | tgg | att | ggt | 240 |
|---|---|---|---|---|---|---|---|---|---|---|---|---|---|---|---|---|
| Leu | Ile | Tyr | Phe | Gly | Ser | Thr | Gly | Ile | Trp | Pro | Leu | Gln | Trp | Ile | Gly | |
| 65 | | | | | 70 | | | | | 75 | | | | | 80 | |

| gca | ggc | atg | acc | gct | tat | ggt | tta | ctg | tat | ttt | atg | gtc | cac | gac | gga | 288 |
|---|---|---|---|---|---|---|---|---|---|---|---|---|---|---|---|---|
| Ala | Gly | Met | Thr | Ala | Tyr | Gly | Leu | Leu | Tyr | Phe | Met | Val | His | Asp | Gly | |
| | | | | 85 | | | | | 90 | | | | | 95 | | |

| ctg | gta | cac | cag | cgc | tgg | ccg | ttc | cgc | tac | ata | ccg | cgc | aaa | ggc | tac | 336 |
|---|---|---|---|---|---|---|---|---|---|---|---|---|---|---|---|---|
| Leu | Val | His | Gln | Arg | Trp | Pro | Phe | Arg | Tyr | Ile | Pro | Arg | Lys | Gly | Tyr | |
| | | | 100 | | | | | 105 | | | | | 110 | | | |

| ctg | aaa | cgg | tta | tac | atg | gcc | cac | cgt | atg | cat | cat | gct | gta | agg | gga | 384 |
|---|---|---|---|---|---|---|---|---|---|---|---|---|---|---|---|---|
| Leu | Lys | Arg | Leu | Tyr | Met | Ala | His | Arg | Met | His | His | Ala | Val | Arg | Gly | |
| | | 115 | | | | | 120 | | | | | 125 | | | | |

| aaa | gag | ggc | tgc | gtg | tcc | ttt | ggt | ttt | ctg | tac | gcg | cca | ccg | tta | tct | 432 |
|---|---|---|---|---|---|---|---|---|---|---|---|---|---|---|---|---|
| Lys | Glu | Gly | Cys | Val | Ser | Phe | Gly | Phe | Leu | Tyr | Ala | Pro | Pro | Leu | Ser | |
| | 130 | | | | | 135 | | | | | 140 | | | | | |

| aaa | ctt | cag | gcg | acg | ctg | aga | gaa | agg | cat | gcg | gct | aga | tcg | ggc | gct | 480 |
|---|---|---|---|---|---|---|---|---|---|---|---|---|---|---|---|---|
| Lys | Leu | Gln | Ala | Thr | Leu | Arg | Glu | Arg | His | Ala | Ala | Arg | Ser | Gly | Ala | |
| 145 | | | | | 150 | | | | | 155 | | | | | 160 | |

| gcc | aga | gat | gag | cag | gac | ggg | gtg | gat | acg | tct | tca | tcc | ggg | aag | taa | 528 |
|---|---|---|---|---|---|---|---|---|---|---|---|---|---|---|---|---|
| Ala | Arg | Asp | Glu | Gln | Asp | Gly | Val | Asp | Thr | Ser | Ser | Ser | Gly | Lys | | |
| | | | | 165 | | | | | 170 | | | | | 175 | | |

<210> SEQ ID NO 12
<211> LENGTH: 175
<212> TYPE: PRT
<213> ORGANISM: Pantoea stewartii

<400> SEQUENCE: 12

| | | | | | | | | | | | | | | | |
|---|---|---|---|---|---|---|---|---|---|---|---|---|---|---|---|
| Met | Leu | Trp | Ile | Trp | Asn | Ala | Leu | Ile | Val | Phe | Val | Thr | Val | Val | Gly |
| 1 | | | | 5 | | | | | 10 | | | | | 15 | |

| Met | Glu | Val | Val | Ala | Ala | Leu | Ala | His | Lys | Tyr | Ile | Met | His | Gly | Trp |
|---|---|---|---|---|---|---|---|---|---|---|---|---|---|---|---|
| | | | 20 | | | | | 25 | | | | | 30 | | |

| Gly | Trp | Gly | Trp | His | Leu | Ser | His | His | Glu | Pro | Arg | Lys | Gly | Ala | Phe |
|---|---|---|---|---|---|---|---|---|---|---|---|---|---|---|---|
| | | 35 | | | | | 40 | | | | | 45 | | | |

| Glu | Val | Asn | Asp | Leu | Tyr | Ala | Val | Val | Phe | Ala | Ile | Val | Ser | Ile | Ala |
|---|---|---|---|---|---|---|---|---|---|---|---|---|---|---|---|
| 50 | | | | | 55 | | | | | 60 | | | | | |

| Leu | Ile | Tyr | Phe | Gly | Ser | Thr | Gly | Ile | Trp | Pro | Leu | Gln | Trp | Ile | Gly |
|---|---|---|---|---|---|---|---|---|---|---|---|---|---|---|---|
| 65 | | | | | 70 | | | | | 75 | | | | | 80 |

| Ala | Gly | Met | Thr | Ala | Tyr | Gly | Leu | Leu | Tyr | Phe | Met | Val | His | Asp | Gly |
|---|---|---|---|---|---|---|---|---|---|---|---|---|---|---|---|
| | | | | 85 | | | | | 90 | | | | | 95 | |

Leu Val His Gln Arg Trp Pro Phe Arg Tyr Ile Pro Arg Lys Gly Tyr

```
                  100                 105                 110
Leu Lys Arg Leu Tyr Met Ala His Arg Met His Ala Val Arg Gly
        115                 120                 125
Lys Glu Gly Cys Val Ser Phe Gly Phe Leu Tyr Ala Pro Pro Leu Ser
130                 135                 140
Lys Leu Gln Ala Thr Leu Arg Glu Arg His Ala Ala Arg Ser Gly Ala
145                 150                 155                 160
Ala Arg Asp Glu Gln Asp Gly Val Asp Thr Ser Ser Ser Gly Lys
                165                 170                 175
```

```
<210> SEQ ID NO 13
<211> LENGTH: 25
<212> TYPE: DNA
<213> ORGANISM: Artificial sequence
<220> FEATURE:
<223> OTHER INFORMATION: Primer

<400> SEQUENCE: 13
atgacggtct gcgcaaaaaa acacg                                         25

<210> SEQ ID NO 14
<211> LENGTH: 28
<212> TYPE: DNA
<213> ORGANISM: Artificial sequence
<220> FEATURE:
<223> OTHER INFORMATION: Primer

<400> SEQUENCE: 14
gagaaattat gttgtggatt tggaatgc                                      28

<210> SEQ ID NO 15
<211> LENGTH: 156
<212> TYPE: DNA
<213> ORGANISM: Artificial sequence
<220> FEATURE:
<223> OTHER INFORMATION: PT5 promoter

<400> SEQUENCE: 15
ctataaaaat aggcgtatca cgaggccctt tcgtcttcac ctcgagaaat cataaaaaat   60
ttatttgctt tgtgagcgga taacaattat aatagattca attgtgagcg ataacaatt  120 tcacacagaa ttcattaaag aggagaaatt aactca                            156

<210> SEQ ID NO 16
<211> LENGTH: 61
<212> TYPE: DNA
<213> ORGANISM: Artificial sequence
<220> FEATURE:
<223> OTHER INFORMATION: Primer

<400> SEQUENCE: 16
tggaagcgct agcggactac atcatccagc gtaataaata acgtcttgag cgattgtgta   60
g                                                                   61

<210> SEQ ID NO 17
<211> LENGTH: 65
<212> TYPE: DNA
<213> ORGANISM: Artificial sequence
<220> FEATURE:
<223> OTHER INFORMATION: Primer

<400> SEQUENCE: 17
tctgatgcgc aagctgaaga aaaatgagca tggagaataa tatgacgtct tgagcgattg   60
```

<210> SEQ ID NO 18
<211> LENGTH: 65
<212> TYPE: DNA
<213> ORGANISM: Artificial sequence
<220> FEATURE:
<223> OTHER INFORMATION: Primer

<400> SEQUENCE: 18
gacgcgtcga agcgcgcaca gtctgcgggg caaaacaatc gataacgtct tgagcgattg    60
tgtag                                                                65

<210> SEQ ID NO 19
<211> LENGTH: 64
<212> TYPE: DNA
<213> ORGANISM: Artificial sequence
<220> FEATURE:
<223> OTHER INFORMATION: Primer

<400> SEQUENCE: 19
gaagacgaaa gggcctcgtg atacgcctat ttttataggt tatatgaata tcctccttag    60
ttcc                                                                 64

<210> SEQ ID NO 20
<211> LENGTH: 50
<212> TYPE: DNA
<213> ORGANISM: Artificial sequence
<220> FEATURE:
<223> OTHER INFORMATION: Primer

<400> SEQUENCE: 20
ctaaggagga tattcatata acctataaaa ataggcgtat cacgaggccc                50

<210> SEQ ID NO 21
<211> LENGTH: 70
<212> TYPE: DNA
<213> ORGANISM: Artificial sequence
<220> FEATURE:
<223> OTHER INFORMATION: Primer

<400> SEQUENCE: 21
ggagtcgacc agtgccaggg tcgggtattt ggcaatatca aaactcatag ttaatttctc    60
ctctttaatg                                                           70

<210> SEQ ID NO 22
<211> LENGTH: 68
<212> TYPE: DNA
<213> ORGANISM: Artificial sequence
<220> FEATURE:
<223> OTHER INFORMATION: Primer

<400> SEQUENCE: 22
tgggaactcc ctgtgcattc aataaaatga cgtgttccgt ttgcatagtt aatttctcct    60
ctttaatg                                                             68

<210> SEQ ID NO 23
<211> LENGTH: 68
<212> TYPE: DNA
<213> ORGANISM: Artificial sequence
<220> FEATURE:
<223> OTHER INFORMATION: Primer

<400> SEQUENCE: 23

```
cggccgccgg aaccacggcg caaacatcca aatgagtggt tgccatagtt aatttctcct      60
ctttaatg                                                               68
```

<210> SEQ ID NO 24
<211> LENGTH: 6329
<212> TYPE: DNA
<213> ORGANISM: Artificial sequence
<220> FEATURE:
<223> OTHER INFORMATION: Plasmid pKD46

<400> SEQUENCE: 24

```
catcgattta ttatgacaac ttgacggcta catcattcac ttttcttca caaccggcac       60
ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat cgcccgcagt aacaattgct     420
caagcagatt tatcgccagc agctccgaat agcgcccttc ccttgcccg gcgttaatga     480
tttgcccaaa caggtcgctg aaatgcggc ggtgcgcttc atccgggcga agaaccccg      540
tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcggaa cagcaaaata tcacccggtc ggcaaacaaa ttctcgtccc tgattttca     720
ccaccccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa aagtgtctat aatcacggca    1080
gaaaagtcca cattgattat ttgcacggcg tcacactttg ctatgccata gcatttttat    1140
ccataagatt agcggatcct acctgacgct tttatcgca actctctact gtttctccat    1200
acccgttttt ttgggaattc gagctctaag gaggttataa aaatggata ttaatactga    1260
aactgagatc aagcaaaagc attcactaac cccctttcct gttttcctaa tcagcccggc    1320
atttcgcggg cgatatttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
```

-continued

```
tttcctgata agcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacgggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgaca cttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc    2520
acaaattacg gctcggcgtc atcaccgctt cagaagttca aacgtgata gcaaaacccc    2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaaatggac gaggcactgg ctgaaattgg ttttgtattt ggggagcaat    3120
ggcgatgacg catcctcacg ataatatccg ggtaggcgca atcactttcg tctactccgt    3180
tacaaagcga ggctgggtat tcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540
ttgttttttgc gtgagccatg agaacgaacc attgagatca tacttacttt gcatgtcact    3600
caaaaatttt gcctcaaaac tggtgagctg aattttgtca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tactattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttcttttaat aaccactcat aaatcctcat    4020
agagtatttg ttttcaaaag acttaacatg ttccagatta tattttatga atttttttaa    4080
ctggaaaaga taaggcaata tctcttcact aaaaactaat tctaattttt cgcttgagaa    4140
cttggcatag tttgtccact ggaaaatctc aaagccttta accaaggat tcctgatttc    4200
cacagttctc gtcatcagct ctctggttgc tttagctaat acaccataag cattttccct    4260
```

```
actgatgttc atcatctgag cgtattggtt ataagtgaac gataccgtcc gttctttcct   4320
tgtagggttt tcaatcgtgg ggttgagtag tgccacacag cataaaatta gcttggtttc   4380
atgctccgtt aagtcatagc gactaatcgc tagttcattt gctttgaaaa caactaattc   4440
agacatacat ctcaattggt ctaggtgatt ttaatcacta taccaattga gatgggctag   4500
tcaatgataa ttactagtcc ttttcctttg agttgtgggt atctgtaaat tctgctagac   4560
cttttgctgga aaacttgtaa attctgctag accctctgta aattccgcta gacctttgtg   4620
tgttttttt gtttatattc aagtggttat aatttataga ataagaaag aataaaaaa   4680
gataaaaga atagatccca gccctgtgta taactcacta ctttagtcag ttccgcagta   4740
ttacaaaagg atgtcgcaaa cgctgtttgc tcctctacaa aacagacctt aaaaccctaa   4800
aggcttaagt agcaccctcg caagctcggt tgcggccgca atcgggcaaa tcgctgaata   4860
ttccttttgt ctccgaccat caggcacctg agtcgctgtc tttttcgtga cattcagttc   4920
gctgcgctca cggctctggc agtgaatggg ggtaaatggc actacaggcg ccttttatgg   4980
attcatgcaa ggaaactacc cataatacaa gaaaagcccg tcacgggctt ctcagggcgt   5040
tttatggcgg gtctgctatg tggtgctatc tgactttttg ctgttcagca gttcctgccc   5100
tctgattttc cagtctgacc acttcggatt atcccgtgac aggtcattca gactggctaa   5160
tgcacccagt aaggcagcgg tatcatcaac ggggtctgac gctcagtgga acgaaaactc   5220
acgttaaggg attttggtca tgagattatc aaaaaggatc ttcacctaga tccttttaaa   5280
ttaaaaatga agttttaaat caatctaaag tatatatgag taaacttggt ctgacagtta   5340
ccaatgctta atcagtgagg cacctatctc agcgatctgt ctatttcgtt catccatagt   5400
tgcctgactc cccgtcgtgt agataactac gatacgggag gcttaccat ctggccccag   5460
tgctgcaatg ataccgcgag acccacgctc accggctcca gatttatcag caataaacca   5520
gccagccgga agggccgagc gcagaagtgg tcctgcaact ttatccgcct ccatccagtc   5580
tattaattgt tgccgggaag ctagagtaag tagttcgcca gttaatagtt tgcgcaacgt   5640
tgttgccatt gctacaggca tcgtggtgtc acgctcgtcg tttggtatgg cttcattcag   5700
ctccggttcc caacgatcaa ggcgagttac atgatccccc atgttgtgca aaaaagcggt   5760
tagctccttc ggtcctccga tcgttgtcag aagtaagttg gccgcagtgt tatcactcat   5820
ggttatggca gcactgcata attctcttac tgtcatgcca tccgtaagat gcttttctgt   5880
gactggtgag tactcaacca agtcattctg agaatagtgt atgcggcgac cgagttgctc   5940
ttgcccggcg tcaatacggg ataataccgc gccacatagc agaactttaa aagtgctcat   6000
cattggaaaa cgttcttcgg ggcgaaaact ctcaaggatc ttaccgctgt tgagatccag   6060
ttcgatgtaa cccactcgtg cacccaactg atcttcagca tcttttactt tcaccagcgt   6120
ttctgggtga gcaaaaacag gaaggcaaaa tgccgcaaaa aagggaataa gggcgacacg   6180
gaaatgttga atactcatac tcttcctttt tcaatattat tgaagcattt atcagggtta   6240
ttgtctcatg agcggataca tatttgaatg tatttagaaa aataaacaaa tagggttcc   6300
gcgcacattt ccccgaaaag tgccacctg                                    6329
```

<210> SEQ ID NO 25
<211> LENGTH: 8609
<212> TYPE: DNA
<213> ORGANISM: Artificial sequence
<220> FEATURE:
<223> OTHER INFORMATION: Plasmid pPCB15

<400> SEQUENCE: 25

```
cgtatggcaa tgaaagacgg tgagctggtg atatgggata gtgttcaccc ttgttacacc        60
gttttccatg agcaaactga aacgttttca tcgctctgga gtgaatacca cgacgatttc       120
cggcagtttc tacacatata ttcgcaagat gtggcgtgtt acggtgaaaa cctggcctat       180
ttccctaaag ggtttattga gaatatgttt ttcgtctcag ccaatccctg ggtgagtttc       240
accagttttg atttaaacgt ggccaatatg gacaacttct tcgcccccgt tttcaccatg       300
ggcaaatatt atacgcaagg cgacaaggtg ctgatgccgc tggcgattca ggttcatcat       360
gccgtctgtg atggcttcca tgtcggcaga atgcttaatg aattacaaca gtactgcgat       420
gagtggcagg gcggggcgta atttttttaa ggcagttatt ggtgcctaga aatattttat       480
ctgattaata agatgatctt cttgagatcg ttttggtctg cgcgtaatct cttgctctga       540
aaacgaaaaa accgccttgc agggcggttt ttcgaaggtt ctctgagcta ccaactcttt       600
gaaccgaggt aactgcttg gaggagcgca gtcaccaaaa cttgtccttt cagtttagcc        660
ttaaccggcg catgacttca agactaactc ctctaaatca attaccagtg ctgctgcca        720
gtggtgcttt tgcatgtctt tccgggttgg actcaagacg atagttaccg gataaggcgc       780
agcggtcgga ctgaacgggg ggttcgtgca tacagtccag cttggagcga actgcctacc       840
cggaactgag tgtcaggcgt ggaatgagac aaacgcggcc ataacagcgg aatgacaccg       900
gtaaaccgaa aggcaggaac aggagagcgc acgagggagc cgccagggga aacgcctggt       960
atctttatag tcctgtcggg tttcgccacc actgatttga gcgtcagatt tcgtgatgct      1020
tgtcaggggg gcggagccta tggaaaaacg gctttgccgc ggccctctca cttccctgtt      1080
aagtatcttc ctggcatctt ccaggaaatc tccgccccgt tcgtaagcca tttccgctcg      1140
ccgcagtcga acgaccgagc gtagcgagtc agtgagcgag gaagcggaat atatcctgta      1200
tcacatattc tgctgacgca ccggtgcagc ctttttttctc ctgccacatg aagcacttca     1260
ctgacaccct catcagtgcc aacatagtaa gccagtatat acactccgct agcgcccaat      1320
acgcaaaccg cctctccccg cgcgttggcc gattcattaa tgcagctggc acgacaggtt      1380
tcccgactgg aaagcgggca gtgagcgcaa cgcaattaat gtgagttagc tcactcatta      1440
ggcaccccag gctttacact ttatgcttcc ggctcgtatg ttgtgtggaa ttgtgagcgg      1500
ataacaattt cacacaggaa acagctatga ccatgattac gaattcgagc tcggtaccca      1560
aacgaattcg ccccttttgac ggtctgcgca aaaaaacacg ttcaccttac tggcatttcg     1620
gctgagcagt tgctggctga tatcgatagc cgccttgatc agttactgcc ggttcagggt      1680
gagcgggatt gtgtgggtgc cgcgatgcgt gaaggcacgc tggcaccggg caaacgtatt      1740
cgtccgatgc tgctgttatt aacagcgcgc gatcttggct gtgcgatcag tcacggggga      1800
ttactggatt tagcctgcgc ggttgaaatg gtgcatgctg cctcgctgat tctggatgat      1860
atgccctgca tggacgatgc gcagatgcgt cgggggcgtc ccaccattca cacgcagtac      1920
ggtgaacatg tggcgattct ggcggcggtc gctttactca gcaaagcgtt tggggtgatt      1980
gccgaggctg aaggtctgac gccgatagcc aaaactcgcg cggtgtcgga gctgtccact      2040
gcgattggca tgcagggtct ggttcagggc cagtttaagg acctctcgga aggcgataaa      2100
ccccgcagcg ccgatgccat actgctaacc aatcagtttta aaaccagcac gctgttttgc      2160
gcgtcaacgc aaatggcgtc cattgcggcc aacgcgtcct gcgaagcgcg tgagaacctg      2220
catcgtttct cgctcgatct cggccaggcc tttcagttgc ttgacgatct taccgatggc      2280
atgaccgata ccggcaaaga catcaatcag gatgcaggta aatcaacgct ggtcaattta      2340
```

-continued

```
ttaggctcag gcgcggtcga agaacgcctg cgacagcatt tgcgcctggc cagtgaacac    2400
ctttccgcgg catgccaaaa cggccattcc accacccaac tttttattca ggcctggttt    2460
gacaaaaaac tcgctgccgt cagttaagga tgctgcatga gccatttgc ggtgatcgca    2520 ccgcccttttt tcagccatgt tcgcgctctg caaaaccttg ctcaggaatt agtggcccgc    2580
ggtcatcgtg ttacgttttt tcagcaacat gactgcaaag cgctggtaac gggcagcgat    2640
atcggattcc agaccgtcgg actgcaaacg catcctcccg gttccttatc gcacctgctg    2700
cacctggccg cgcacccact cggaccctcg atgttacgac tgatcaatga atggcacgt    2760 accagcgata tgctttgccg ggaactgccc gccgcttttc atgcgttgca gatagagggc    2820
gtgatcgttg atcaaatgga gccggcaggt gcagtagtcg cagaagcgtc aggtctgccg    2880
tttgtttcgg tggcctgcgc gctgccgctc aaccgcgaac cgggtttgcc tctggcggtg    2940
atgcctttcg agtacggcac cagcgatgcg gctcgggaac gctataccac cagcgaaaaa    3000
atttatgact ggctgatgcg acgtcacgat cgtgtgatcg cgcatcatgc atgcagaatg    3060
ggtttagccc cgcgtgaaaa actgcatcat tgttttctc cactggcaca aatcagccag    3120
ttgatccccg aactggattt tccccgcaaa gcgctgccag actgctttca tgcggttgga    3180
ccgttacggc aaccccaggg gacgccgggg tcatcaactt cttattttcc gtccccggac    3240
aaaccccgta ttttttgcctc gctgggcacc ctgcaggac atcgttatgg cctgttcagg    3300
accatcgcca aagcctgcga agaggtggat gcgcagttac tgttggcaca ctgtggcggc    3360
ctctcagcca cgcaggcagg tgaactgcc cggggcgggg acattcaggt tgtggatttt    3420
gccgatcaat ccgcagcact ttcacaggca cagttgacaa tcacacatgg tgggatgaat    3480
acggtactgg acgctattgc ttcccgcaca ccgctactgg cgctgccgct ggcatttgat    3540
caacctggcg tggcatcacg aattgtttat catggcatcg gcaagcgtgc gtctcggttt    3600
actaccagcc atgcgctggc gcggcagatt cgatcgctgc tgactaacac cgattacccg    3660
cagcgtatga caaaaattca ggccgcattg cgtctggcag gcggcacacc agccgccgcc    3720
gatattgttg aacaggcgat gcggacctgt cagccagtac tcagtgggca ggattatgca    3780
accgcactat gatctcattc tggtcggtgc cggtctggct aatggcctta tcgcgctccg    3840
gcttcagcaa cagcatccgg atatgcggat cttgcttatt gaggcgggtc ctgaggcggg    3900
agggaaccat acctggtcct ttcacgaaga ggatttaacg ctgaatcagc atcgctggat    3960
agcgccgctt gtggtccatc actggcccga ctaccaggtt cgtttccccc aacgccgtcg    4020
ccatgtgaac agtggctact actgcgtgac ctcccggcat ttcgccggga tactccggca    4080
acagtttgga caacatttat ggctgcatac cgcggtttca gccgttcatg ctgaatcggt    4140
ccagttagcg gatggccgga ttattcatgc cagtacagtg atcgacggac ggggttacac    4200
gcctgattct gcactacgcg taggattcca ggcatttatc ggtcaggagt ggcaactgag    4260
cgcgccgcat ggtttatcgt caccgattat catggatgcg acggtcgatc agcaaaatgg    4320
ctaccgcttt gtttataccc tgccgctttc cgcaaccgca ctgctgatcg aagcacacac    4380
ctacattgac aaggctaatc ttcaggccga acgggcgcgt cagaacattc gcgattatgc    4440
tgcgcgacag ggttggccgt tacagacgtt gctgcgggaa gaacagggtg cattgcccat    4500
tacgttaacg ggcgataatc gtcagttttg gcaacagcaa ccgcaagcct gtagcggatt    4560
acgcgccggg ctgtttcatc cgacaaccgg ctactcccta ccgctcgcgg tggcgctggc    4620
cgatcgtctc agcgcgctgg atgtgtttac ctcttcctct gttcaccaga cgattgctca    4680
```

-continued

```
ctttgcccag caacgttggc agcaacaggg gttttttccgc atgctgaatc gcatgttgtt    4740
tttagccgga ccggccgagt cacgctggcg tgtgatgcag cgtttctatg gcttacccga    4800
ggatttgatt gcccgctttt atgcgggaaa actcaccgtg accgatcggc tacgcattct    4860
gagcggcaag ccgcccgttc ccgttttcgc ggcattgcag gcaattatga cgactcatcg    4920
ttgaagagcg actacatgaa accaactacg gtaattggtg cgggctttgg tggcctggca    4980
ctggcaattc gtttacaggc cgcaggtatt cctgttttgc tgcttgagca gcgcgacaag    5040
ccgggtggcc gggcttatgt ttatcaggag cagggcttta cttttgatgc aggccctacc    5100
gttatcaccg atcccagcgc gattgaagaa ctgtttgctc tggccggtaa acagcttaag    5160
gattacgtcg agctgttgcc ggtcacgccg ttttatcgcc tgtgctggga gtccggcaag    5220
gtcttcaatt acgataacga ccaggcccag ttagaagcgc agatacagca gtttaatccg    5280
cgcgatgttg cgggttatcg agcgttcctt gactattcgc gtgccgtatt caatgagggc    5340
tatctgaagc tcggcactgt gcctttttta tcgttcaaag acatgcttcg ggccgcgccc    5400
cagttggcaa agctgcaggc atggcgcagc gtttacagta agttgccgg ctacattgag    5460 gatgagcatc ttcggcaggc gttttctttt cactcgctct tagtgggggg gaatccgttt    5520
gcaacctcgt ccatttatac gctgattcac gcgttagaac gggaatgggg cgtctggttt    5580
ccacgcggtg gaaccggtgc gctggtcaat ggcatgatca agctgtttca ggatctgggc    5640
ggcgaagtcg tgcttaacgc ccgggtcagt catatggaaa ccgttgggga caagattcag    5700
gccgtgcagt tggaagacgg cagacggttt gaaacctgcg cggtggcgtc gaacgctgat    5760
gttgtacata cctatcgcga tctgctgtct cagcatcccg cagccgctaa gcaggcgaaa    5820
aaactgcaat ccaagcgtat gagtaactca ctgtttgtac tctattttgg tctcaaccat    5880
catcacgatc aactcgccca tcataccgtc tgttttgggc cacgctaccg tgaactgatt    5940
cacgaaattt ttaaccatga tggtctggct gaggattttt cgctttattt acacgcacct    6000
tgtgtcacgg atccgtcact ggcaccggaa gggtgcggca gctattatgt gctggcgcct    6060
gttccacact taggcacggc gaacctcgac tgggcggtag aaggacccg actgcgcgat    6120 cgtattttg actaccttga gcaacattac atgcctggct tgcgaagcca gttggtgacg    6180
caccgtatgt ttacgccgtt cgatttccgc gacgagctca atgcctggca aggttcggcc    6240
ttctcggttg aacctattct gacccagagc gcctggttcc gaccacataa ccgcgataag    6300
cacattgata tctttatct ggttggcgca ggcaccccatc ctggcgcggg cattcccggc    6360
gtaatcggct cggcgaaggc gacggcaggc ttaatgctgg aggacctgat tgacgaata    6420 cgtcattact gaatcatgcc gtcgaaacca tggcggttgg ctcgaaaagc tttgcgactg    6480
catcgacgct tttcgacgcc aaaacccgtc gcagcgtgct gatgctttac gcatggtgcc    6540
gccactgcga cgacgtcatt gacgatcaaa cactgggctt tcatgccgac cagccctctt    6600
cgcagatgcc tgagcagcgc ctgcagcagc ttgaaatgaa aacgcgtcag gcctacgccg    6660
gttcgcaaat gcacgagccc gcttttgccg cgtttcagga ggtcgcgatg gcgcatgata    6720
tcgctcccgc ctacgcgttc gaccatctgg aaggttttgc catggatgtg cgcgaaacgc    6780
gctacctgac actggacgat acgctgcgtt attgctatca cgtcgccggt gttgtgggcc    6840
tgatgatggc gcaaattatg ggcgttcgcg ataacgccac gctcgatcgc gcctgcgatc    6900
tcgggctggc tttccagttg accaacattg cgcgtgatat tgtcgacgat gctcaggtgg    6960
gccgctgtta tctgcctgaa agctggctgg aagaggaagg actgacgaaa gcgaattatg    7020
ctgcgccaga aaaccggcag gccttaagcc gtatcgccgg gcgactggta cgggaagcgg    7080
```

-continued

```
aaccctatta cgtatcatca atggccggtc tggcacaatt acccttacgc tcggcctggg    7140
ccatcgcgac agcgaagcag gtgtaccgta aaattggcgt gaaagttgaa caggccggta    7200
agcaggcctg ggatcatcgc cagtccacgt ccaccgccga aaaattaacg cttttgctga    7260
cggcatccgg tcaggcagtt acttcccgga tgaagacgta tccacccccgt cctgctcatc    7320 tctggcagcg cccgatctag ccgcatgcct ttctctcagc gtcgcctgaa gtttagataa    7380
cggtggcgcg tacagaaaac caaggacac gcagccctct tttcccctta cagcatgatg    7440
catacggtgg gccatgtata accgtttcag gtagcctttg cgcggtatgt agcggaacgg    7500
ccagcgctgg tgtaccagtc cgtcgtggac cataaaatac agtaaaccat aagcggtcat    7560
gcctgcacca atccactgga gcggccagat tcctgtactg ccgaagtaaa tcagggcaat    7620
cgacacaatg gcgaatacca cggcatagag atcgttaact tcaaatgcgc ctttacgcgg    7680
ttcatgatgt gaaagatgcc agccccaacc ccagccgtgc atgatgtatt tatgtgccag    7740
tgcagcaacc acttccatgc cgaccacggt gacaaacacg atcagggcat tccaaatcca    7800
caacataatt tctcaagggc gaattcgcgg ggatcctcta gagtcgacct gcaggcatgc    7860
aagcttggca ctggccgtcg ttttacaacg tcgtgactgg gaaaaccctg gcgttaccca    7920
acttaatcgc cttgcagcac atccccctttc gccagctgg cgtaatagcg aagaggcccg    7980
caccgatcgc ccttcccaac agttgcgcag cctgaatggc gaatggcgct gatgtccggc    8040
ggtgcttttg ccgttacgca ccaccccgtc agtagctgaa caggagggac agctgataga    8100
aacagaagcc actggagcac ctcaaaaaca ccatcataca ctaaatcagt aagttggcag    8160
catcacccga cgcactttgc gccgaataaa tacctgtgac ggaagatcac ttcgcagaat    8220
aaataaatcc tggtgtccct gttgataccg ggaagccctg ggccaacttt tggcgaaaat    8280
gagacgttga tcggcacgta agaggttcca actttcacca taatgaaata agatcactac    8340
cgggcgtatt ttttgagtta tcgagatttt caggagctaa ggaagctaaa atggagaaaa    8400
aaatcactgg atataccacc gttgatatat cccaatggca tcgtaaagaa cattttgagg    8460
catttcagtc agttgctcaa tgtacctata accagaccgt tcagctggat attacggcct    8520
ttttaaagac cgtaaagaaa aataagcaca gttttatcc ggcctttatt cacattcttg    8580
cccgcctgat gaatgctcat ccggaattt                                      8609
```

<210> SEQ ID NO 26
<211> LENGTH: 25
<212> TYPE: DNA
<213> ORGANISM: Artificial sequence
<220> FEATURE:
<223> OTHER INFORMATION: Primer

<400> SEQUENCE: 26
accggatatc accacttatc tgctc                                          25

<210> SEQ ID NO 27
<211> LENGTH: 26
<212> TYPE: DNA
<213> ORGANISM: Artificial sequence
<220> FEATURE:
<223> OTHER INFORMATION: Primer

<400> SEQUENCE: 27
tggcaacagt cgtagctcct gggtgg                                         26

<210> SEQ ID NO 28

<210> SEQ ID NO 28
<211> LENGTH: 32
<212> TYPE: DNA
<213> ORGANISM: Artificial sequence
<220> FEATURE:
<223> OTHER INFORMATION: Primer

<400> SEQUENCE: 28
taacctataa aataggcgt atcacgaggc cc                               32

<210> SEQ ID NO 29
<211> LENGTH: 25
<212> TYPE: DNA
<213> ORGANISM: Artificial sequence
<220> FEATURE:
<223> OTHER INFORMATION: Primer

<400> SEQUENCE: 29
tcatgctgac ctggtgaagg aatcc                                      25

<210> SEQ ID NO 30
<211> LENGTH: 25
<212> TYPE: DNA
<213> ORGANISM: Artificial sequence
<220> FEATURE:
<223> OTHER INFORMATION: Primer

<400> SEQUENCE: 30
ccagcagcgc atgcaccgag tgttc                                      25

<210> SEQ ID NO 31
<211> LENGTH: 729
<212> TYPE: DNA
<213> ORGANISM: Agrobacterium aurantiacum

<400> SEQUENCE: 31
atgagcgcac atgccctgcc caaggcagat ctgaccgcca ccagcctgat cgtctcgggc     60
ggcatcatcg ccgcttggct ggccctgcat gtgcatgcgc tgtggtttct ggacgcagcg    120
gcgcatccca tcctggcgat cgcaaatttc ctggggctga cctggctgtc ggtcggattg    180
ttcatcatcg cgcatgacgc gatgcacggg tcggtggtgc cggggcgtcc gcgcgccaat    240
gcggcgatgg ccagcttgt cctgtggctg tatgccggat tttcgtggcg caagatgatc    300
gtcaagcaca tggcccatca ccgccatgcc ggaaccgacg acgaccccga tttcgaccat    360
ggcggcccgg tccgctggta cgcccgcttc atcggcacct atttcggctg gcgcgagggg    420
ctgctgctgc ccgtcatcgt gacggtctat gcgctgatcc ttggggatcg ctggatgtac    480
gtggtcttct ggccgctgcc gtcgatcctg gcgtcgatcc agctgttcgt gttcggcacc    540
tggctgccgc accgccccgg ccacgacgcg ttcccggacc gccacaatgc gcggtcgtcg    600
cggatcagcg accccgtgtc gctgctgacc tgctttcact tggcggtta tcatcacgaa    660
caccacctgc acccgacggt gccgtggtgg cgcctgccca gcacccgcac caaggggac    720
accgcatga                                                           729

<210> SEQ ID NO 32
<211> LENGTH: 756
<212> TYPE: DNA
<213> ORGANISM: Artificial sequence
<220> FEATURE:
<223> OTHER INFORMATION: Codon Optimized Version of Agrobacterium
      aurantiacum crtW

<400> SEQUENCE: 32

-continued

```
caattgaagg aggaataaac catgagcgcc catgccctgc cgaaagccga cctgaccgcg      60
accagcctga tcgtcagcgg tggcatcatc gcggcctggc tggcgctgca tgtccatgcc     120
ctgtggttcc tggacgccgc cgcccatccg atcctggcca tcgccaactt cctgggcctg     180
acctggctga gcgtcggcct gttcatcatc gcgcatgacg ccatgcatgg cagcgtggtc     240
ccgggtcgtc cgcgtgccaa cgccgccatg ggccaactgg tcctgtggtt gtatgccggc     300
ttcagctggc gcaagatgat cgtcaaacat atggcccatc atcgccacgc gggcaccgac     360
gacgatccgg acttcgacca tggtggcccg gtccgctggt atgcgcgctt catcggcacc     420
tatttcggct ggcgtgaagg cctgttgctg ccggtcatcg tcaccgtcta tgcgctgatc     480
ctgggcgacc gctggatgta tgtcgtcttc tggccgctgc cgagcatcct ggcgagcatc     540
caactgttcg tcttcggtac ctggctgccg catcgcccgg ccatgacgc ctttccggac      600
cgccataacg cccgcagcag ccgcatcagc gacccggtca gcctgctgac ctgcttccat     660
ttcggcggct atcatcatga acatcatctg catccgaccg tcccgtggtg cgcctgccg      720
agcacccgca ccaaaggcga caccgcgtga caattg                               756
```

<210> SEQ ID NO 33
<211> LENGTH: 242
<212> TYPE: PRT
<213> ORGANISM: Agrobacterium aurantiacum

<400> SEQUENCE: 33

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Ile Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240
```

Thr Ala

<210> SEQ ID NO 34
<211> LENGTH: 3611
<212> TYPE: DNA
<213> ORGANISM: Pantoea stewartii

<400> SEQUENCE: 34

| | | | | | |
|---|---|---|---|---|---|
| aaaactcgct | gccgtcagtt | aacaattgag | tgggcaggat | tatgcaaccg | cactatgatc | 60 |
| tcattctggt | cggtgccggt | ctggctaatg | gccttatcgc | gctccggctt | cagcaacagc | 120 |
| atccggatat | gcgatcttg | cttattgagg | cgggtcctga | ggcgggaggg | aaccatacct | 180 |
| ggtcctttca | cgaagaggat | ttaacgctga | atcagcatcg | ctggatagcg | ccgcttgtgg | 240 |
| tccatcactg | gcccgactac | caggttcgtt | tcccccaacg | ccgtcgccat | gtgaacagtg | 300 |
| gctactactg | cgtgacctcc | cggcatttcg | ccgggatact | ccggcaacag | tttggacaac | 360 |
| atttatggct | gcataccgcg | gtttcagccg | ttcatgctga | atcggtccag | ttagcggatg | 420 |
| gccggattat | tcatgccagt | acagtgatcg | acggacgggg | ttacacgcct | gattctgcac | 480 |
| tacgcgtagg | attccaggca | tttatcggtc | aggagtggca | actgagcgcg | ccgcatggtt | 540 |
| tatcgtcacc | gattatcatg | gatgcgacgg | tcgatcagca | aaatggctac | cgctttgttt | 600 |
| ataccctgcc | gctttccgca | accgcactgc | tgatcgaaga | cacacactac | attgacaagg | 660 |
| ctaatcttca | ggccgaacgg | gcgcgtcaga | acattcgcga | ttatgctgcg | cgacagggtt | 720 |
| ggccgttaca | gacgttgctg | cgggaagaac | agggtgcatt | gcccattacg | ttaacgggcg | 780 |
| ataatcgtca | gttttggcaa | cagcaaccgc | aagcctgtag | cggattacgc | gccgggctgt | 840 |
| tcatccgac | aaccggctac | tccctaccgc | tcgcggtggc | gctggccgat | cgtctcagcg | 900 |
| cgctggatgt | gtttacctct | tcctctgttc | accagacgat | tgctcacttt | gcccagcaac | 960 |
| gttggcagca | acaggggttt | ttccgcatgc | tgaatcgcat | gttgtttta | gccggaccgg | 1020 |
| ccgagtcacg | ctggcgtgtg | atgcagcgtt | tctatggctt | acccgaggat | ttgattgccc | 1080 |
| gcttttatgc | gggaaaactc | accgtgaccg | atcggctacg | cattctgagc | ggcaagccgc | 1140 |
| ccgttcccgt | tttcgcggca | ttgcaggcaa | ttatgacgac | tcatcgttga | agagcgacta | 1200 |
| catgaaacca | actacggtaa | ttggtgcggg | ctttggtggc | ctggcactgg | caattcgttt | 1260 |
| acaggccgca | ggtattcctg | ttttgctgct | tgagcagcgc | gacaagccgg | gtggccgggc | 1320 |
| ttatgtttat | caggagcagg | gctttacttt | tgatgcaggc | cctaccgtta | tcaccgatcc | 1380 |
| cagcgcgatt | gaagaactgt | ttgctctggc | cggtaaacag | cttaaggatt | acgtcgagct | 1440 |
| gttgccggtc | acgccgtttt | atcgcctgtg | ctgggagtcc | ggcaaggtct | tcaattacga | 1500 |
| taacgaccag | gcccagttag | aagcgcagat | acagcagttt | aatccgcgcg | atgttgcggg | 1560 |
| ttatcgagcg | ttccttgact | attcgcgtgc | cgtattcaat | gagggctatc | tgaagctcgg | 1620 |
| cactgtgcct | tttttatcgt | tcaaagacat | gcttcgggcc | gcgccccagt | ggcaaagct | 1680 |
| gcaggcatgg | cgcagcgttt | acagtaaagt | tgccggctac | attgaggatg | agcatcttcg | 1740 |
| gcaggcgttt | tcttttcact | cgctcttagt | gggggggaat | ccgtttgcaa | cctcgtccat | 1800 |
| ttatacgctg | attcacgcgt | tagaacggga | atgggcgtc | tggtttccac | gcggtggaac | 1860 |
| cggtgcgctg | gtcaatggca | tgatcaagct | gtttcaggat | ctgggcggcg | aagtcgtgct | 1920 |
| taacgcccgg | gtcagtcata | tggaaaccgt | tggggacaag | attcaggccg | tgcagttgga | 1980 |
| agacggcaga | cggtttgaaa | cctgcgcggt | ggcgtcgaac | gctgatgttg | tacataccta | 2040 |
| tcgcgatctg | ctgtctcagc | atcccgcagc | cgctaagcag | gcgaaaaaac | tgcaatccaa | 2100 |

```
gcgtatgagt aactcactgt ttgtactcta ttttggtctc aaccatcatc acgatcaact    2160
cgcccatcat accgtctgtt ttgggccacg ctaccgtgaa ctgattcacg aaatttttaa    2220
ccatgatggt ctggctgagg atttttcgct ttatttacac gcaccttgtg tcacggatcc    2280
gtcactggca ccggaagggt gcggcagcta ttatgtgctg gcgcctgttc cacacttagg    2340
cacggcgaac ctcgactggg cggtagaagg accccgactg cgcgatcgta tttttgacta    2400
ccttgagcaa cattacatgc ctggcttgcg aagccagttg gtgacgcacc gtatgtttac    2460
gccgttcgat ttccgcgacg agctcaatgc ctggcaaggt tcggccttct cggttgaacc    2520
tattctgacc cagagcgcct ggttccgacc acataaccgc gataagcaca ttgataatct    2580
ttatctggtt ggcgcaggca cccatcctgg cgcgggcatt cccggcgtaa tcggctcggc    2640
gaaggcgacg gcaggcttaa tgctggagga cctgatttga cgaatacgtc attactgaat    2700
catgccgtcg aaaccatggc ggttggctcg aaaagctttg cgactgcatc gacgcttttc    2760
gacgccaaaa cccgtcgcag cgtgctgatg ctttacgcat ggtgccgcca ctgcgacgac    2820
gtcattgacg atcaaacact ggctttcat gccgaccagc cctcttcgca gatgcctgag    2880
cagcgcctgc agcagcttga aatgaaaacg cgtcaggcct acgccggttc gcaaatgcac    2940
gagcccgctt ttgccgcgtt tcaggaggtc gcgatggcgc atgatatcgc tcccgcctac    3000
gcgttcgacc atctggaagg ttttgccatg gatgtgcgcg aaacgcgcta cctgacactg    3060
gacgatacgc tgcgttattg ctatcacgtc gccggtgttg tgggcctgat gatgcgcaa    3120 attatgggcg ttcgcgataa cgccacgctc gatcgcgcct gcgatctcgg gctggctttc    3180
cagttgacca acattgcgcg tgatattgtc gacgatgctc aggtgggccg ctgttatctg    3240
cctgaaagct ggctggaaga ggaaggactg acgaaagcga attatgctgc gccagaaaac    3300
cggcaggcct taagccgtat cgccgggcga ctggtacggg aagcggaacc ctattacgta    3360
tcatcaatgg ccgtctggc acaattaccc ttacgctcgg cctgggccat cgcgacagcg    3420
aagcaggtgt accgtaaaat tggcgtgaaa gttgaacagg ccggtaagca ggcctgggat    3480
catcgccagt ccacgtccac cgccgaaaaa ttaacgcttt tgctgacggc atccggtcag    3540
gcagttactt cccggatgaa gacgtatcca ccccgtcctg ctcatctctg gcagcgcccg    3600
atctaggtac c                                                        3611
```

<210> SEQ ID NO 35
<211> LENGTH: 20
<212> TYPE: DNA
<213> ORGANISM: artificial sequence
<220> FEATURE:
<223> OTHER INFORMATION: Primer

<400> SEQUENCE: 35
gaattcgccc ttgacggtct                                                20

<210> SEQ ID NO 36
<211> LENGTH: 50
<212> TYPE: DNA
<213> ORGANISM: artificial sequence
<220> FEATURE:
<223> OTHER INFORMATION: Primer

<400> SEQUENCE: 36
cggttgcata atcctgccca ctcaattgtt aactgacggc agcgagtttt                50

<210> SEQ ID NO 37

```
-continued

<211> LENGTH: 50
<212> TYPE: DNA
<213> ORGANISM: artificial sequence
<220> FEATURE:
<223> OTHER INFORMATION: Primer

<400> SEQUENCE: 37
aaaactcgct gccgtcagtt aacaattgag tgggcaggat tatgcaaccg          50

<210> SEQ ID NO 38
<211> LENGTH: 25
<212> TYPE: DNA
<213> ORGANISM: artificial sequence
<220> FEATURE:
<223> OTHER INFORMATION: Primer

<400> SEQUENCE: 38
ggtacctaga tcgggcgctg ccaga                                     25

<210> SEQ ID NO 39
<211> LENGTH: 492
<212> TYPE: DNA
<213> ORGANISM: Cyamopsis tetragonoloba
<220> FEATURE:
<221> NAME/KEY: CDS
<222> LOCATION: (1)..(492)

<400> SEQUENCE: 39 atg gct tct atg act tct gat caa cca aga aca gga tcc tac tct tat    48
Met Ala Ser Met Thr Ser Asp Gln Pro Arg Thr Gly Ser Tyr Ser Tyr
1               5                   10                  15 ggt tcc tat gac aac tcc aac ttt ggc aac acc aca acc tca atc ttc    96
Gly Ser Tyr Asp Asn Ser Asn Phe Gly Asn Thr Thr Thr Ser Ile Phe
            20                  25                  30 act ccc tca cgc caa act gtc aag ttc ata aca gct gct aca att ggt   144
Thr Pro Ser Arg Gln Thr Val Lys Phe Ile Thr Ala Ala Thr Ile Gly
        35                  40                  45 gta aca ctt ttg ctg tta tct ggt ttg att ctc act ggt act gtc att   192
Val Thr Leu Leu Leu Leu Ser Gly Leu Ile Leu Thr Gly Thr Val Ile
    50                  55                  60 ggc ttg atc att gca act cct ctt ctt gtt ctc ttc agc ccc atc ttg   240
Gly Leu Ile Ile Ala Thr Pro Leu Leu Val Leu Phe Ser Pro Ile Leu
65                  70                  75                  80 gtt cct gct gct ttt gtt ctc ttc ctt gct gct tcc ggc ttt ctc ttt   288
Val Pro Ala Ala Phe Val Leu Phe Leu Ala Ala Ser Gly Phe Leu Phe
                85                  90                  95 tcc ggt ggc tgc ggt gtt gca gct att gcc gca ttg tca tgg ata tac   336
Ser Gly Gly Cys Gly Val Ala Ala Ile Ala Ala Leu Ser Trp Ile Tyr
            100                 105                 110 aat tat gtc gca ggg agg cat ccg acg ggt gct gac acg ctt gat tac   384
Asn Tyr Val Ala Gly Arg His Pro Thr Gly Ala Asp Thr Leu Asp Tyr
        115                 120                 125 gct aaa aac atg att gct gat aag gct aga gat gtt aag gaa agg gct   432
Ala Lys Asn Met Ile Ala Asp Lys Ala Arg Asp Val Lys Glu Arg Ala
    130                 135                 140 aag gat tat gga aat tat gct cag agt aaa gta caa gag gcc act caa   480
Lys Asp Tyr Gly Asn Tyr Ala Gln Ser Lys Val Gln Glu Ala Thr Gln
145                 150                 155                 160 gga tct tac taa                                                   492
Gly Ser Tyr

<210> SEQ ID NO 40
<211> LENGTH: 163
```

```
<212> TYPE: PRT
<213> ORGANISM: Cyamopsis tetragonoloba

<400> SEQUENCE: 40

Met Ala Ser Met Thr Ser Asp Gln Pro Arg Thr Gly Ser Tyr Ser Tyr
1               5                   10                  15

Gly Ser Tyr Asp Asn Ser Asn Phe Gly Asn Thr Thr Thr Ser Ile Phe
            20                  25                  30

Thr Pro Ser Arg Gln Thr Val Lys Phe Ile Thr Ala Ala Thr Ile Gly
        35                  40                  45

Val Thr Leu Leu Leu Ser Gly Leu Ile Leu Thr Gly Thr Val Ile
    50                  55                  60

Gly Leu Ile Ile Ala Thr Pro Leu Leu Val Leu Phe Ser Pro Ile Leu
65                  70                  75                  80

Val Pro Ala Ala Phe Val Leu Phe Leu Ala Ala Ser Gly Phe Leu Phe
                85                  90                  95

Ser Gly Gly Cys Gly Val Ala Ala Ile Ala Ala Leu Ser Trp Ile Tyr
            100                 105                 110

Asn Tyr Val Ala Gly Arg His Pro Thr Gly Ala Asp Thr Leu Asp Tyr
            115                 120                 125

Ala Lys Asn Met Ile Ala Asp Lys Ala Arg Asp Val Lys Glu Arg Ala
    130                 135                 140

Lys Asp Tyr Gly Asn Tyr Ala Gln Ser Lys Val Gln Glu Ala Thr Gln
145                 150                 155                 160

Gly Ser Tyr

<210> SEQ ID NO 41
<211> LENGTH: 561
<212> TYPE: DNA
<213> ORGANISM: Zea mays
<220> FEATURE:
<221> NAME/KEY: CDS
<222> LOCATION: (1)..(561)

<400> SEQUENCE: 41 atg gcg gac cgt gac cgc agc ggc atc tac ggc ggc gcc cac gcc acc      48
Met Ala Asp Arg Asp Arg Ser Gly Ile Tyr Gly Gly Ala His Ala Thr
1               5                   10                  15 tac ggg cag cag cag cag cag gga gga ggc ggg cgc ccg atg ggt gag      96
Tyr Gly Gln Gln Gln Gln Gln Gly Gly Gly Gly Arg Pro Met Gly Glu
            20                  25                  30 cag gtg aag ggc atg ctc cac gac aag ggg ccg acg gcg tcg cag gcg     144
Gln Val Lys Gly Met Leu His Asp Lys Gly Pro Thr Ala Ser Gln Ala
        35                  40                  45 ctg acg gtg gcg acg ctg ttc ccg ctg ggc ggg ctg ctg gtg ctg         192
Leu Thr Val Ala Thr Leu Phe Pro Leu Gly Gly Leu Leu Val Leu
    50                  55                  60 tcg ggg ctg gcg ctg acg gcc tcc gtg gtg ggg ctg gcc gtg gcc acg     240
Ser Gly Leu Ala Leu Thr Ala Ser Val Val Gly Leu Ala Val Ala Thr
65                  70                  75                  80 ccg gtg ttc ctg atc ttc agc ccc gtg ctg gtc ccc gcc gcg ctg ctc     288
Pro Val Phe Leu Ile Phe Ser Pro Val Leu Val Pro Ala Ala Leu Leu
                85                  90                  95 atc ggg acg gcc gtc atg ggg ttc ctc acg tcg ggc gcg ctg ggg ctc     336
Ile Gly Thr Ala Val Met Gly Phe Leu Thr Ser Gly Ala Leu Gly Leu
            100                 105                 110 ggg ggc ctg tcc tcg ctc acg tgc ctc gcc aac acg gcg cgg cag gcg     384
Gly Gly Leu Ser Ser Leu Thr Cys Leu Ala Asn Thr Ala Arg Gln Ala
        115                 120                 125
```

```
ttc cag cgc acc ccg gac tac gtg gag gag gcg cac cgc agg atg gcg      432
Phe Gln Arg Thr Pro Asp Tyr Val Glu Glu Ala His Arg Arg Met Ala
    130                 135                 140 gag gcc gcg gcg cac gcg ggc cac aag acc gcg cag gca ggc cag gcc      480
Glu Ala Ala Ala His Ala Gly His Lys Thr Ala Gln Ala Gly Gln Ala
145                 150                 155                 160 atc cag ggc agg gcg cag gag gcc ggc gcc ggg gga ggt gca ggt gcc      528
Ile Gln Gly Arg Ala Gln Glu Ala Gly Ala Gly Gly Ala Gly Ala
                165                 170                 175 ggc gct ggc ggc ggc ggc agg gct tcc tcg tag                          561
Gly Ala Gly Gly Gly Gly Arg Ala Ser Ser
        180                 185

<210> SEQ ID NO 42
<211> LENGTH: 186
<212> TYPE: PRT
<213> ORGANISM: Zea mays

<400> SEQUENCE: 42

Met Ala Asp Arg Asp Arg Ser Gly Ile Tyr Gly Gly Ala His Ala Thr
1               5                   10                  15

Tyr Gly Gln Gln Gln Gln Gly Gly Gly Arg Pro Met Gly Glu
            20                  25                  30

Gln Val Lys Gly Met Leu His Asp Lys Gly Pro Thr Ala Ser Gln Ala
        35                  40                  45

Leu Thr Val Ala Thr Leu Phe Pro Leu Gly Gly Leu Leu Leu Val Leu
    50                  55                  60

Ser Gly Leu Ala Leu Thr Ala Ser Val Val Gly Leu Ala Val Ala Thr
65                  70                  75                  80

Pro Val Phe Leu Ile Phe Ser Pro Val Leu Val Pro Ala Ala Leu Leu
                85                  90                  95

Ile Gly Thr Ala Val Met Gly Phe Leu Thr Ser Gly Ala Leu Gly Leu
            100                 105                 110

Gly Gly Leu Ser Ser Leu Thr Cys Leu Ala Asn Thr Ala Arg Gln Ala
        115                 120                 125

Phe Gln Arg Thr Pro Asp Tyr Val Glu Glu Ala His Arg Arg Met Ala
    130                 135                 140

Glu Ala Ala Ala His Ala Gly His Lys Thr Ala Gln Ala Gly Gln Ala
145                 150                 155                 160

Ile Gln Gly Arg Ala Gln Glu Ala Gly Ala Gly Gly Ala Gly Ala
                165                 170                 175

Gly Ala Gly Gly Gly Gly Arg Ala Ser Ser
        180                 185

<210> SEQ ID NO 43
<211> LENGTH: 447
<212> TYPE: DNA
<213> ORGANISM: Ricinus communis
<220> FEATURE:
<221> NAME/KEY: CDS
<222> LOCATION: (1)..(447)

<400> SEQUENCE: 43 atg tct gat caa cca aga tct ctg cac cag atg acc cct ggt aca gca      48
Met Ser Asp Gln Pro Arg Ser Leu His Gln Met Thr Pro Gly Thr Ala
1               5                   10                  15 gca ccc tct cat ctt gtg gtc aag ttc cta acc gca gcc acg gta ggt      96
Ala Pro Ser His Leu Val Val Lys Phe Leu Thr Ala Ala Thr Val Gly
            20                  25                  30
```

```
gtt gct tgc ttg ttt cta tcc ggt ttg atc tta acc ggg aca gtg atc      144
Val Ala Cys Leu Phe Leu Ser Gly Leu Ile Leu Thr Gly Thr Val Ile
         35                  40                  45 acc ttg gtt atg gcc act cct ctg ttg gtt ctt tct ggt ccc att atg      192
Thr Leu Val Met Ala Thr Pro Leu Leu Val Leu Ser Gly Pro Ile Met
 50                  55                  60 gtc cct gct gca ata gtt gta ttc ttg gtt tgc tcg ggg ttc ttt ttc      240
Val Pro Ala Ala Ile Val Val Phe Leu Val Cys Ser Gly Phe Phe Phe
 65                  70                  75                  80 tct ggc ggg tgt ggg ttg gcg gcg ata atg tct tta act tgg atg tac      288
Ser Gly Gly Cys Gly Leu Ala Ala Ile Met Ser Leu Thr Trp Met Tyr
                 85                  90                  95 aag tac ttg aca ggg aag cat ccg cca ggt gct gat aag ttg gac tat      336
Lys Tyr Leu Thr Gly Lys His Pro Pro Gly Ala Asp Lys Leu Asp Tyr
            100                 105                 110 gca aga gga cag ata gct aga aag gct cat gat atg aag gag aga gct      384
Ala Arg Gly Gln Ile Ala Arg Lys Ala His Asp Met Lys Glu Arg Ala
        115                 120                 125 aaa gaa tat gga cag tat gtt cag caa aaa gca caa gaa gct act caa      432
Lys Glu Tyr Gly Gln Tyr Val Gln Gln Lys Ala Gln Glu Ala Thr Gln
    130                 135                 140 act cga gca tct taa                                                  447
Thr Arg Ala Ser
145

<210> SEQ ID NO 44
<211> LENGTH: 148
<212> TYPE: PRT
<213> ORGANISM: Ricinus communis

<400> SEQUENCE: 44

Met Ser Asp Gln Pro Arg Ser Leu His Gln Met Thr Pro Gly Thr Ala
 1               5                  10                  15

Ala Pro Ser His Leu Val Val Lys Phe Leu Thr Ala Ala Thr Val Gly
             20                  25                  30

Val Ala Cys Leu Phe Leu Ser Gly Leu Ile Leu Thr Gly Thr Val Ile
         35                  40                  45

Thr Leu Val Met Ala Thr Pro Leu Leu Val Leu Ser Gly Pro Ile Met
 50                  55                  60

Val Pro Ala Ala Ile Val Val Phe Leu Val Cys Ser Gly Phe Phe Phe
 65                  70                  75                  80

Ser Gly Gly Cys Gly Leu Ala Ala Ile Met Ser Leu Thr Trp Met Tyr
                 85                  90                  95

Lys Tyr Leu Thr Gly Lys His Pro Pro Gly Ala Asp Lys Leu Asp Tyr
            100                 105                 110

Ala Arg Gly Gln Ile Ala Arg Lys Ala His Asp Met Lys Glu Arg Ala
        115                 120                 125

Lys Glu Tyr Gly Gln Tyr Val Gln Gln Lys Ala Gln Glu Ala Thr Gln
    130                 135                 140

Thr Arg Ala Ser
145

<210> SEQ ID NO 45
<211> LENGTH: 462
<212> TYPE: DNA
<213> ORGANISM: Ricinus communis
<220> FEATURE:
<221> NAME/KEY: CDS
<222> LOCATION: (1)..(462)
```

```
<400> SEQUENCE: 45 atg gct gat cgt ccg cag ccg cac cag gtg caa gtg cac cgc tat gat      48
Met Ala Asp Arg Pro Gln Pro His Gln Val Gln Val His Arg Tyr Asp
1               5                   10                  15 cca act act ggc tac aag ggc caa cag aag ggt cca tca gcc tcc aaa      96
Pro Thr Thr Gly Tyr Lys Gly Gln Gln Lys Gly Pro Ser Ala Ser Lys
            20                  25                  30 gtg tta gct gtg tta acc ttt ctg ccg gtt ggt ggt ggt ctt cta tct     144
Val Leu Ala Val Leu Thr Phe Leu Pro Val Gly Gly Gly Leu Leu Ser
        35                  40                  45 ctc tct ggc ata acc tta acg aat acg ctc atc ggg atg gcc att gcc     192
Leu Ser Gly Ile Thr Leu Thr Asn Thr Leu Ile Gly Met Ala Ile Ala
    50                  55                  60 acc cca ctt ttt att ctc ttc ggc cct ata att ctt cct gct gcc gtt     240
Thr Pro Leu Phe Ile Leu Phe Gly Pro Ile Ile Leu Pro Ala Ala Val
65                  70                  75                  80 gtt att ggc ctt gct atg atg gca ttt atg gtt gct gga gct ctc ggg     288
Val Ile Gly Leu Ala Met Met Ala Phe Met Val Ala Gly Ala Leu Gly
                85                  90                  95 ctg agc ggg ctg acg tcg cag tcg tgg gcg ttg aag tat ttc agg gaa     336
Leu Ser Gly Leu Thr Ser Gln Ser Trp Ala Leu Lys Tyr Phe Arg Glu
            100                 105                 110 ggt act gcc atg cca gaa tca ctg gac cag gcg aag aag cgc atg cag     384
Gly Thr Ala Met Pro Glu Ser Leu Asp Gln Ala Lys Lys Arg Met Gln
        115                 120                 125 gac atg gcc ggt tat gtt ggg atg aag acc aag gaa gtg gga caa gac     432
Asp Met Ala Gly Tyr Val Gly Met Lys Thr Lys Glu Val Gly Gln Asp
    130                 135                 140 atc cag agg aag gca caa gaa ggg aaa tga                             462
Ile Gln Arg Lys Ala Gln Glu Gly Lys
145                 150

<210> SEQ ID NO 46
<211> LENGTH: 153
<212> TYPE: PRT
<213> ORGANISM: Ricinus communis

<400> SEQUENCE: 46

Met Ala Asp Arg Pro Gln Pro His Gln Val Gln Val His Arg Tyr Asp
1               5                   10                  15

Pro Thr Thr Gly Tyr Lys Gly Gln Gln Lys Gly Pro Ser Ala Ser Lys
            20                  25                  30

Val Leu Ala Val Leu Thr Phe Leu Pro Val Gly Gly Gly Leu Leu Ser
        35                  40                  45

Leu Ser Gly Ile Thr Leu Thr Asn Thr Leu Ile Gly Met Ala Ile Ala
    50                  55                  60

Thr Pro Leu Phe Ile Leu Phe Gly Pro Ile Ile Leu Pro Ala Ala Val
65                  70                  75                  80

Val Ile Gly Leu Ala Met Met Ala Phe Met Val Ala Gly Ala Leu Gly
                85                  90                  95

Leu Ser Gly Leu Thr Ser Gln Ser Trp Ala Leu Lys Tyr Phe Arg Glu
            100                 105                 110

Gly Thr Ala Met Pro Glu Ser Leu Asp Gln Ala Lys Lys Arg Met Gln
        115                 120                 125

Asp Met Ala Gly Tyr Val Gly Met Lys Thr Lys Glu Val Gly Gln Asp
    130                 135                 140

Ile Gln Arg Lys Ala Gln Glu Gly Lys
145                 150
```

```
                   145                 150

<210> SEQ ID NO 47
<211> LENGTH: 402
<212> TYPE: DNA
<213> ORGANISM: Vitis sp.
<220> FEATURE:
<221> NAME/KEY: CDS
<222> LOCATION: (1)..(402)

<400> SEQUENCE: 47 atg gct cat caa gac cag cct cag aaa acc cag ctt tct tat cag ctc       48
Met Ala His Gln Asp Gln Pro Gln Lys Thr Gln Leu Ser Tyr Gln Leu
1               5                   10                  15 atc aag acc tca acc gca gcc acc atc ggc ggc tcc tgc atg gtt ctc       96
Ile Lys Thr Ser Thr Ala Ala Thr Ile Gly Gly Ser Cys Met Val Leu
                20                  25                  30 tcc ggc ctc acc ctc gcc ggg acc gtg atc gcc ctg gtg gtg gcc acg      144
Ser Gly Leu Thr Leu Ala Gly Thr Val Ile Ala Leu Val Val Ala Thr
            35                  40                  45 ccg ctg ctg gtg ata ttc agc cct gtg ctg gtg ccg gcg gcc ata acg      192
Pro Leu Leu Val Ile Phe Ser Pro Val Leu Val Pro Ala Ala Ile Thr
        50                  55                  60 gtg ttc tta gcg gca agt ggg ctg gtg gcg tcg gga gga ttt gga gtg      240
Val Phe Leu Ala Ala Ser Gly Leu Val Ala Ser Gly Gly Phe Gly Val
65                  70                  75                  80 agc gca gtg tcg gtg ttt tta tgg ctg tac aaa tac gta agg gga cag      288
Ser Ala Val Ser Val Phe Leu Trp Leu Tyr Lys Tyr Val Arg Gly Gln
                85                  90                  95 cac cca gtt ggt gca gac agg ctg gat cgc gca cga gac aag ctg acg      336
His Pro Val Gly Ala Asp Arg Leu Asp Arg Ala Arg Asp Lys Leu Thr
            100                 105                 110 ggc aag gcc atg gag gtg aag gag cgg gcg gca gag cag att ggc act      384
Gly Lys Ala Met Glu Val Lys Glu Arg Ala Ala Glu Gln Ile Gly Thr
        115                 120                 125 aga gga acg cag ggt tga                                              402
Arg Gly Thr Gln Gly
    130

<210> SEQ ID NO 48
<211> LENGTH: 133
<212> TYPE: PRT
<213> ORGANISM: Vitis sp.

<400> SEQUENCE: 48

Met Ala His Gln Asp Gln Pro Gln Lys Thr Gln Leu Ser Tyr Gln Leu
1               5                   10                  15

Ile Lys Thr Ser Thr Ala Ala Thr Ile Gly Gly Ser Cys Met Val Leu
                20                  25                  30

Ser Gly Leu Thr Leu Ala Gly Thr Val Ile Ala Leu Val Val Ala Thr
            35                  40                  45

Pro Leu Leu Val Ile Phe Ser Pro Val Leu Val Pro Ala Ala Ile Thr
        50                  55                  60

Val Phe Leu Ala Ala Ser Gly Leu Val Ala Ser Gly Gly Phe Gly Val
65                  70                  75                  80

Ser Ala Val Ser Val Phe Leu Trp Leu Tyr Lys Tyr Val Arg Gly Gln
                85                  90                  95

His Pro Val Gly Ala Asp Arg Leu Asp Arg Ala Arg Asp Lys Leu Thr
            100                 105                 110

Gly Lys Ala Met Glu Val Lys Glu Arg Ala Ala Glu Gln Ile Gly Thr
```

115                    120                     125
Arg Gly Thr Gln Gly
    130

<210> SEQ ID NO 49
<211> LENGTH: 423
<212> TYPE: DNA
<213> ORGANISM: Amaranthus sp.
<220> FEATURE:
<221> NAME/KEY: CDS
<222> LOCATION: (1)..(423)

<400> SEQUENCE: 49 atg tac gga acg act tac tca ggg cag cat caa cag cag tcg cag tct      48
Met Tyr Gly Thr Thr Tyr Ser Gly Gln His Gln Gln Gln Ser Gln Ser
1               5                   10                  15 tac cag atg gtt aag gcg gca act gcc ata acc gct ggt ggg tcc ctt      96
Tyr Gln Met Val Lys Ala Ala Thr Ala Ile Thr Ala Gly Gly Ser Leu
            20                  25                  30 tta atc cta tct gca tta act cta tca gga acc gtg atc gcc ctc aca     144
Leu Ile Leu Ser Ala Leu Thr Leu Ser Gly Thr Val Ile Ala Leu Thr
        35                  40                  45 gta gcg aca cca ttg ctg gtg ata ttt agc ccg gtt ctg gtg ccg gca     192
Val Ala Thr Pro Leu Leu Val Ile Phe Ser Pro Val Leu Val Pro Ala
 50                  55                  60 gca att act gtg gtg atg ttg atc aca gga ttt tta gct tca ggc ggg     240
Ala Ile Thr Val Val Met Leu Ile Thr Gly Phe Leu Ala Ser Gly Gly
65                  70                  75                  80 ttt gga gtg gca gct gtg ttg gtt atg gct tgg ctt tac cga tac atg     288
Phe Gly Val Ala Ala Val Leu Val Met Ala Trp Leu Tyr Arg Tyr Met
                85                  90                  95 acg ggc cga cat cca gtt gga gcg gac tct ttg gag caa gca agg atg     336
Thr Gly Arg His Pro Val Gly Ala Asp Ser Leu Glu Gln Ala Arg Met
            100                 105                 110 aag ctg gct gga aaa gct agg gaa gct agg gag aaa gga gag cat tat     384
Lys Leu Ala Gly Lys Ala Arg Glu Ala Arg Glu Lys Gly Glu His Tyr
        115                 120                 125 gtg cag cag gct act gga ggt act cac cag act tct taa                 423
Val Gln Gln Ala Thr Gly Gly Thr His Gln Thr Ser
    130                 135                 140

<210> SEQ ID NO 50
<211> LENGTH: 140
<212> TYPE: PRT
<213> ORGANISM: Amaranthus sp.

<400> SEQUENCE: 50

Met Tyr Gly Thr Thr Tyr Ser Gly Gln His Gln Gln Gln Ser Gln Ser
1               5                   10                  15

Tyr Gln Met Val Lys Ala Ala Thr Ala Ile Thr Ala Gly Gly Ser Leu
            20                  25                  30

Leu Ile Leu Ser Ala Leu Thr Leu Ser Gly Thr Val Ile Ala Leu Thr
        35                  40                  45

Val Ala Thr Pro Leu Leu Val Ile Phe Ser Pro Val Leu Val Pro Ala
 50                  55                  60

Ala Ile Thr Val Val Met Leu Ile Thr Gly Phe Leu Ala Ser Gly Gly
65                  70                  75                  80

Phe Gly Val Ala Ala Val Leu Val Met Ala Trp Leu Tyr Arg Tyr Met
                85                  90                  95

Thr Gly Arg His Pro Val Gly Ala Asp Ser Leu Glu Gln Ala Arg Met

```
                    100                 105                 110
Lys Leu Ala Gly Lys Ala Arg Glu Ala Arg Glu Lys Gly Glu His Tyr
            115                 120                 125

Val Gln Gln Ala Thr Gly Gly Thr His Gln Thr Ser
        130                 135                 140

<210> SEQ ID NO 51
<211> LENGTH: 426
<212> TYPE: DNA
<213> ORGANISM: Catalpa sp.
<220> FEATURE:
<221> NAME/KEY: CDS
<222> LOCATION: (1)..(426)

<400> SEQUENCE: 51 atg gcg gag caa tac cgc gag cat cag caa agc acc acc gaa aag ggt      48
Met Ala Glu Gln Tyr Arg Glu His Gln Gln Ser Thr Thr Glu Lys Gly
1               5                   10                  15 ccc tcc acc tcc caa gtc ctt gcc atc gtc acc ctc ttc ccc gtc ggc      96
Pro Ser Thr Ser Gln Val Leu Ala Ile Val Thr Leu Phe Pro Val Gly
            20                  25                  30 agc ttc ctc ctc att cta gcg ggt ctc act ctc gcc gca act ctc atc     144
Ser Phe Leu Leu Ile Leu Ala Gly Leu Thr Leu Ala Ala Thr Leu Ile
        35                  40                  45 ggc ctc acc gtc gcc atc cct ctc ttt gtc atc ttc agc ccc atc tta     192
Gly Leu Thr Val Ala Ile Pro Leu Phe Val Ile Phe Ser Pro Ile Leu
    50                  55                  60 gtc ccc gcc gtc ctc acc atc gcc tta gcc gtt gcc gga ttc ttg acc     240
Val Pro Ala Val Leu Thr Ile Ala Leu Ala Val Ala Gly Phe Leu Thr
65                  70                  75                  80 tcc ggc gct ttt ggc atc act gcg cta tct tca gtt tcg tgg ttg ctc     288
Ser Gly Ala Phe Gly Ile Thr Ala Leu Ser Ser Val Ser Trp Leu Leu
                85                  90                  95 aac tac ttg agg aaa atg cgg ggg agc ttg ccg gag caa ttc gag cat     336
Asn Tyr Leu Arg Lys Met Arg Gly Ser Leu Pro Glu Gln Phe Glu His
            100                 105                 110 gca agg cgg cgc gtg aaa ggc acg gca agt cat atg ggc cag aag acg     384
Ala Arg Arg Arg Val Lys Gly Thr Ala Ser His Met Gly Gln Lys Thr
        115                 120                 125 agg gaa gca ggc cag aaa gcc caa gat gta atg aga cct tga             426
Arg Glu Ala Gly Gln Lys Ala Gln Asp Val Met Arg Pro
    130                 135                 140

<210> SEQ ID NO 52
<211> LENGTH: 141
<212> TYPE: PRT
<213> ORGANISM: Catalpa sp.

<400> SEQUENCE: 52

Met Ala Glu Gln Tyr Arg Glu His Gln Gln Ser Thr Thr Glu Lys Gly
1               5                   10                  15

Pro Ser Thr Ser Gln Val Leu Ala Ile Val Thr Leu Phe Pro Val Gly
            20                  25                  30

Ser Phe Leu Leu Ile Leu Ala Gly Leu Thr Leu Ala Ala Thr Leu Ile
        35                  40                  45

Gly Leu Thr Val Ala Ile Pro Leu Phe Val Ile Phe Ser Pro Ile Leu
    50                  55                  60

Val Pro Ala Val Leu Thr Ile Ala Leu Ala Val Ala Gly Phe Leu Thr
65                  70                  75                  80

Ser Gly Ala Phe Gly Ile Thr Ala Leu Ser Ser Val Ser Trp Leu Leu
```

```
                        85                  90                  95
Asn Tyr Leu Arg Lys Met Arg Gly Ser Leu Pro Glu Gln Phe Glu His
            100                 105                 110

Ala Arg Arg Val Lys Gly Thr Ala Ser His Met Gly Gln Lys Thr
        115                 120                 125

Arg Glu Ala Gly Gln Lys Ala Gln Asp Val Met Arg Pro
130                 135                 140

<210> SEQ ID NO 53
<211> LENGTH: 609
<212> TYPE: DNA
<213> ORGANISM: Vernonia sp.
<220> FEATURE:
<221> NAME/KEY: CDS
<222> LOCATION: (1)..(609)

<400> SEQUENCE: 53 atg gct acc act ttc gat cgg caa caa cac tac acc acc acc caa caa      48
Met Ala Thr Thr Phe Asp Arg Gln Gln His Tyr Thr Thr Thr Gln Gln
1               5                   10                  15 ccg cac cac cgt gac cgc tat gat tat cgc acc gcc ggc gat aaa ctc      96
Pro His His Arg Asp Arg Tyr Asp Tyr Arg Thr Ala Gly Asp Lys Leu
            20                  25                  30 cac tac cct caa tca ggt tca ggc cca tcc aca acc aaa gtc atg gcc     144
His Tyr Pro Gln Ser Gly Ser Gly Pro Ser Thr Thr Lys Val Met Ala
        35                  40                  45 atc gtc gcc tta ctt ccg gtc ggc gga atc tta ctt ggt cta gct ggt     192
Ile Val Ala Leu Leu Pro Val Gly Gly Ile Leu Leu Gly Leu Ala Gly
50                  55                  60 atc acc ctc gtc gga aca atg atc gga cta gct gta gcc act cca gtc     240
Ile Thr Leu Val Gly Thr Met Ile Gly Leu Ala Val Ala Thr Pro Val
65                  70                  75                  80 ttc gtc att ttc agt ccg gtt atc gtt ccg gca att ctg acg att ggg     288
Phe Val Ile Phe Ser Pro Val Ile Val Pro Ala Ile Leu Thr Ile Gly
                85                  90                  95 ctg gcg gtg aca ggg ttt tta acg tcg gga acg ttt gga tta acg ggg     336
Leu Ala Val Thr Gly Phe Leu Thr Ser Gly Thr Phe Gly Leu Thr Gly
            100                 105                 110 ttg agc tcg tta tcg tac ttg gta aat gtg ttg agg cag acg gca ggg     384
Leu Ser Ser Leu Ser Tyr Leu Val Asn Val Leu Arg Gln Thr Ala Gly
        115                 120                 125 tcg gtg ccg gaa cag ata gat tat gcg aag gga atg gtg cag gat ttg     432
Ser Val Pro Glu Gln Ile Asp Tyr Ala Lys Gly Met Val Gln Asp Leu
    130                 135                 140 ggg gtg tat gca ggg cag aaa aca aag gag atg ggt cag atg att cag     480
Gly Val Tyr Ala Gly Gln Lys Thr Lys Glu Met Gly Gln Met Ile Gln
145                 150                 155                 160 cac aag ggt cat gaa atg gga acc cag ggt cag ggt cag ggt caa ggt     528
His Lys Gly His Glu Met Gly Thr Gln Gly Gln Gly Gln Gly Gln Gly
                165                 170                 175 gta gta agt gta ggt gtg ggt cag ggt caa ggt caa ggt gct cat gtg     576
Val Val Ser Val Gly Val Gly Gln Gly Gln Gly Gln Gly Ala His Val
            180                 185                 190 caa gct ggt ggg gaa aga agg tgg gaa aag tga                         609
Gln Ala Gly Gly Glu Arg Arg Trp Glu Lys
        195                 200

<210> SEQ ID NO 54
<211> LENGTH: 202
<212> TYPE: PRT
<213> ORGANISM: Vernonia sp.
```

<400> SEQUENCE: 54

| Met | Ala | Thr | Thr | Phe | Asp | Arg | Gln | Gln | His | Tyr | Thr | Thr | Thr | Gln | Gln |
| 1 | | | | 5 | | | | | 10 | | | | | 15 | |

| Pro | His | His | Arg | Asp | Arg | Tyr | Asp | Tyr | Arg | Thr | Ala | Gly | Asp | Lys | Leu |
| | | | 20 | | | | | 25 | | | | | 30 | | |

| His | Tyr | Pro | Gln | Ser | Gly | Ser | Gly | Pro | Ser | Thr | Thr | Lys | Val | Met | Ala |
| | | | 35 | | | | | 40 | | | | | 45 | | |

| Ile | Val | Ala | Leu | Leu | Pro | Val | Gly | Gly | Ile | Leu | Leu | Gly | Leu | Ala | Gly |
| | | 50 | | | | | 55 | | | | | 60 | | | |

| Ile | Thr | Leu | Val | Gly | Thr | Met | Ile | Gly | Leu | Ala | Val | Ala | Thr | Pro | Val |
| 65 | | | | | 70 | | | | | 75 | | | | | 80 |

| Phe | Val | Ile | Phe | Ser | Pro | Val | Ile | Val | Pro | Ala | Ile | Leu | Thr | Ile | Gly |
| | | | | 85 | | | | | 90 | | | | | 95 | |

| Leu | Ala | Val | Thr | Gly | Phe | Leu | Thr | Ser | Gly | Thr | Phe | Gly | Leu | Thr | Gly |
| | | | 100 | | | | | 105 | | | | | 110 | | |

| Leu | Ser | Ser | Leu | Ser | Tyr | Leu | Val | Asn | Val | Leu | Arg | Gln | Thr | Ala | Gly |
| | | | 115 | | | | | 120 | | | | | 125 | | |

| Ser | Val | Pro | Glu | Gln | Ile | Asp | Tyr | Ala | Lys | Gly | Met | Val | Gln | Asp | Leu |
| | | 130 | | | | | 135 | | | | | 140 | | | |

| Gly | Val | Tyr | Ala | Gly | Gln | Lys | Thr | Lys | Glu | Met | Gly | Gln | Met | Ile | Gln |
| 145 | | | | | 150 | | | | | 155 | | | | | 160 |

| His | Lys | Gly | His | Glu | Met | Gly | Thr | Gln | Gly | Gln | Gly | Gln | Gly | Gln | Gly |
| | | | | 165 | | | | | 170 | | | | | 175 | |

| Val | Val | Ser | Val | Gly | Val | Gly | Gln | Gly | Gln | Gly | Gln | Gly | Ala | His | Val |
| | | | 180 | | | | | 185 | | | | | 190 | | |

| Gln | Ala | Gly | Gly | Glu | Arg | Arg | Trp | Glu | Lys |
| | | 195 | | | | | 200 | | |

<210> SEQ ID NO 55
<211> LENGTH: 465
<212> TYPE: DNA
<213> ORGANISM: Gossypium hirsutum
<220> FEATURE:
<221> NAME/KEY: CDS
<222> LOCATION: (1)..(465)

<400> SEQUENCE: 55

| atg | gcc | gac | cgt | gac | cgc | tct | tac | cgg | acg | ttt | gac | cag | gtt | gtt | cgt | 48 |
| Met | Ala | Asp | Arg | Asp | Arg | Ser | Tyr | Arg | Thr | Phe | Asp | Gln | Val | Val | Arg | |
| 1 | | | | 5 | | | | | 10 | | | | | 15 | | |

| ggt | gat | aga | acg | aac | tat | caa | agc | gga | cca | tca | aca | acc | caa | gtt | cta | 96 |
| Gly | Asp | Arg | Thr | Asn | Tyr | Gln | Ser | Gly | Pro | Ser | Thr | Thr | Gln | Val | Leu | |
| | | | 20 | | | | | 25 | | | | | 30 | | | |

| act | gtc | ctc | acc | ctc | ctt | ccc | ata | ggc | ggc | act | ctc | ctt | gca | tta | gcc | 144 |
| Thr | Val | Leu | Thr | Leu | Leu | Pro | Ile | Gly | Gly | Thr | Leu | Leu | Ala | Leu | Ala | |
| | | | 35 | | | | | 40 | | | | | 45 | | | |

| ggg | cta | acc | ctc | acc | ggc | acc | gtc | atc | ggc | cta | tgc | atg | gca | acg | cca | 192 |
| Gly | Leu | Thr | Leu | Thr | Gly | Thr | Val | Ile | Gly | Leu | Cys | Met | Ala | Thr | Pro | |
| | | 50 | | | | | 55 | | | | | 60 | | | | |

| ctc | ttc | gtc | atc | ttc | agc | ccg | gtt | ctg | gtc | cca | gct | gcc | atc | gcg | gtc | 240 |
| Leu | Phe | Val | Ile | Phe | Ser | Pro | Val | Leu | Val | Pro | Ala | Ala | Ile | Ala | Val | |
| 65 | | | | | 70 | | | | | 75 | | | | | 80 | |

| ttc | atg | gct | gtg | gcc | ggt | ttc | ttg | tcg | tcc | ggg | gca | ttc | ggg | ttg | acg | 288 |
| Phe | Met | Ala | Val | Ala | Gly | Phe | Leu | Ser | Ser | Gly | Ala | Phe | Gly | Leu | Thr | |
| | | | | 85 | | | | | 90 | | | | | 95 | | |

| ggg | ctg | tcc | tcg | ctc | tcc | tac | gta | ttt | aac | cgc | ttc | aga | cag | gcg | act | 336 |
| Gly | Leu | Ser | Ser | Leu | Ser | Tyr | Val | Phe | Asn | Arg | Phe | Arg | Gln | Ala | Thr | |

```
ggc acc gag cag ctc gac gcg gac cgg gcc aag agg ggc atg caa gat      384
Gly Thr Glu Gln Leu Asp Ala Asp Arg Ala Lys Arg Gly Met Gln Asp
        115                 120                 125 atg gtg ggg tat gtg gga caa aag act aag gaa act ggg cag act atc      432
Met Val Gly Tyr Val Gly Gln Lys Thr Lys Glu Thr Gly Gln Thr Ile
130                 135                 140 gaa aac aag gct cat gag ggt ggt agg aca tga                          465
Glu Asn Lys Ala His Glu Gly Gly Arg Thr
145                 150

<210> SEQ ID NO 56
<211> LENGTH: 154
<212> TYPE: PRT
<213> ORGANISM: Gossypium hirsutum

<400> SEQUENCE: 56

Met Ala Asp Arg Asp Arg Ser Tyr Arg Thr Phe Asp Gln Val Val Arg
1               5                   10                  15

Gly Asp Arg Thr Asn Tyr Gln Ser Gly Pro Ser Thr Thr Gln Val Leu
            20                  25                  30

Thr Val Leu Thr Leu Leu Pro Ile Gly Gly Thr Leu Leu Ala Leu Ala
        35                  40                  45

Gly Leu Thr Leu Thr Gly Thr Val Ile Gly Leu Cys Met Ala Thr Pro
    50                  55                  60

Leu Phe Val Ile Phe Ser Pro Val Leu Val Pro Ala Ala Ile Ala Val
65                  70                  75                  80

Phe Met Ala Val Ala Gly Phe Leu Ser Ser Gly Ala Phe Gly Leu Thr
                85                  90                  95

Gly Leu Ser Ser Leu Ser Tyr Val Phe Asn Arg Phe Arg Gln Ala Thr
            100                 105                 110

Gly Thr Glu Gln Leu Asp Ala Asp Arg Ala Lys Arg Gly Met Gln Asp
        115                 120                 125

Met Val Gly Tyr Val Gly Gln Lys Thr Lys Glu Thr Gly Gln Thr Ile
    130                 135                 140

Glu Asn Lys Ala His Glu Gly Gly Arg Thr
145                 150

<210> SEQ ID NO 57
<211> LENGTH: 650
<212> TYPE: DNA
<213> ORGANISM: Tagetes sp.

<400> SEQUENCE: 57
gtggatcccc cgggctgcag gaattcggca ccagctacaa catacgcata tggagaccgt       60
caacaccaca ccgccggatt aactcacacc ggcggagttg gcggtgggta ccggtacgat      120
cactccgaca ggttccgcta ccctcaacag aatcaaggtg catcaaccag caagataatg      180
gccaccatgg ccttacttcc tctgggtgga atcttgctgg ggttagcagg tctcaccttc      240
gtcggaaccc tgatcggact cgctgttgca actccggtgt tgtaattttt cagcccggtg      300
attgttccgg cgttactgac gattgggctc gccgtcactg gttttttgac ttcggggact      360
ttcgggttga ccggactgag ctcgttgtcg tatttggtga cgatgttgag gcagtcagca      420
ccatcggtgc cggatcagat ggattacgtt aaggggaagt gcaagatgt cggcgactat       480 gccgggcara agacgaagga tgtcggtcag gggattcaga ataaggctca tgatatcggg      540
aatatagatt tgggtggcgg tcaggctggc gctggtggtg gtgtgcatgt tcaagttggt      600
```

-continued ggtggtggta agaaggtgg gaaagaagga cgaaaaggcg gtgataggac        650

<210> SEQ ID NO 58
<211> LENGTH: 216
<212> TYPE: PRT
<213> ORGANISM: Tagetes sp.

<400> SEQUENCE: 58

Val Asp Pro Pro Gly Cys Arg Asn Ser Ala Pro Ala Thr Thr Tyr Ala
1               5                   10                  15

Tyr Gly Asp Arg Gln His His Thr Ala Gly Leu Thr His Thr Gly Gly
            20                  25                  30

Val Gly Gly Gly Tyr Arg Tyr Asp His Ser Asp Arg Phe Arg Tyr Pro
        35                  40                  45

Gln Gln Asn Gln Gly Ala Ser Thr Ser Lys Ile Met Ala Thr Met Ala
    50                  55                  60

Leu Leu Pro Leu Gly Ile Leu Leu Gly Leu Ala Gly Leu Thr Phe
65                  70                  75                  80

Val Gly Thr Leu Ile Gly Leu Ala Val Ala Thr Pro Val Phe Val Ile
                85                  90                  95

Phe Ser Pro Val Ile Val Pro Ala Leu Leu Thr Ile Gly Leu Ala Val
            100                 105                 110

Thr Gly Phe Leu Thr Ser Gly Thr Phe Gly Leu Thr Gly Leu Ser Ser
        115                 120                 125

Leu Ser Tyr Leu Val Thr Met Leu Arg Gln Ser Ala Pro Ser Val Pro
    130                 135                 140

Asp Gln Met Asp Tyr Val Lys Gly Lys Leu Gln Asp Val Gly Asp Tyr
145                 150                 155                 160

Ala Gly Gln Lys Thr Lys Asp Val Gly Gln Gly Ile Gln Asn Lys Ala
                165                 170                 175

His Asp Ile Gly Asn Ile Asp Leu Gly Gly Gln Ala Gly Ala Gly
            180                 185                 190

Gly Gly Val His Val Gln Val Gly Gly Gly Lys Glu Gly Gly Lys
        195                 200                 205

Glu Gly Arg Lys Gly Gly Asp Arg
    210                 215

<210> SEQ ID NO 59
<211> LENGTH: 558
<212> TYPE: DNA
<213> ORGANISM: Momordica charantia
<220> FEATURE:
<221> NAME/KEY: CDS
<222> LOCATION: (1)..(558)

<400> SEQUENCE: 59 atg ggt gac cgt tcg ccg ccg cac cag ctc cag gcc cac tcc cag cag    48
Met Gly Asp Arg Ser Pro Pro His Gln Leu Gln Ala His Ser Gln Gln
1               5                   10                  15 cgc ccc tac ggc cag gac ccg gcc tct tgg aag ctc gcc ggc ggc cgc    96
Arg Pro Tyr Gly Gln Asp Pro Ala Ser Trp Lys Leu Ala Gly Gly Arg
            20                  25                  30 ctc ccg gac ttc ccc tac caa cag cag cag cag caa ggc ccc tcc       144
Leu Pro Asp Phe Pro Tyr Gln Gln Gln Gln Gln Gln Gly Pro Ser
        35                  40                  45 gcc tcc aag atc ctg gcc gtc gtc acc ctc gtc ccc gtc ggg ggt acg    192
Ala Ser Lys Ile Leu Ala Val Val Thr Leu Val Pro Val Gly Gly Thr
    50                  55                  60

```
ctg ctc ggc ctc tcc ggc ctc acg ctg gcg gtc acg ctc ttc ggg ctg      240
Leu Leu Gly Leu Ser Gly Leu Thr Leu Ala Val Thr Leu Phe Gly Leu
 65                  70                  75                  80 gcc gtg tcc acg ccg gtg ttc ctg ctg ttc agc ccg gtg ata gtc ccg      288
Ala Val Ser Thr Pro Val Phe Leu Leu Phe Ser Pro Val Ile Val Pro
                 85                  90                  95 gcg gcg gtg gca ata ttc ctg gcg gtg atg gcg ttc ctt acg tcg gga      336
Ala Ala Val Ala Ile Phe Leu Ala Val Met Ala Phe Leu Thr Ser Gly
            100                 105                 110 gtg ttc gga ctg acg gct ctg tca tcg ctg tcg tgg gtg tac cgg tac      384
Val Phe Gly Leu Thr Ala Leu Ser Ser Leu Ser Trp Val Tyr Arg Tyr
        115                 120                 125 ata cga aag gcg acg ggg acg atg ccg gag cag atg gac atg gcg aag      432
Ile Arg Lys Ala Thr Gly Thr Met Pro Glu Gln Met Asp Met Ala Lys
130                 135                 140 agg cgc atg cag gac atg gcc ggg tac gtg ggg cag aag aca aag gat      480
Arg Arg Met Gln Asp Met Ala Gly Tyr Val Gly Gln Lys Thr Lys Asp
145                 150                 155                 160 gtg gga caa gag att cag agc agg gct cag gaa ggg agg agg acc gcc      528
Val Gly Gln Glu Ile Gln Ser Arg Ala Gln Glu Gly Arg Arg Thr Ala
                165                 170                 175 act gaa caa cat gaa cga cga aca act taa                              558
Thr Glu Gln His Glu Arg Arg Thr Thr
            180                 185

<210> SEQ ID NO 60
<211> LENGTH: 185
<212> TYPE: PRT
<213> ORGANISM: Momordica charantia

<400> SEQUENCE: 60

Met Gly Asp Arg Ser Pro Pro His Gln Leu Gln Ala His Ser Gln Gln
  1               5                  10                  15

Arg Pro Tyr Gly Gln Asp Pro Ala Ser Trp Lys Leu Ala Gly Gly Arg
             20                  25                  30

Leu Pro Asp Phe Pro Tyr Gln Gln Gln Gln Gln Gln Gln Gly Pro Ser
         35                  40                  45

Ala Ser Lys Ile Leu Ala Val Val Thr Leu Val Pro Val Gly Gly Thr
     50                  55                  60

Leu Leu Gly Leu Ser Gly Leu Thr Leu Ala Val Thr Leu Phe Gly Leu
 65                  70                  75                  80

Ala Val Ser Thr Pro Val Phe Leu Leu Phe Ser Pro Val Ile Val Pro
                 85                  90                  95

Ala Ala Val Ala Ile Phe Leu Ala Val Met Ala Phe Leu Thr Ser Gly
            100                 105                 110

Val Phe Gly Leu Thr Ala Leu Ser Ser Leu Ser Trp Val Tyr Arg Tyr
        115                 120                 125

Ile Arg Lys Ala Thr Gly Thr Met Pro Glu Gln Met Asp Met Ala Lys
130                 135                 140

Arg Arg Met Gln Asp Met Ala Gly Tyr Val Gly Gln Lys Thr Lys Asp
145                 150                 155                 160

Val Gly Gln Glu Ile Gln Ser Arg Ala Gln Glu Gly Arg Arg Thr Ala
                165                 170                 175

Thr Glu Gln His Glu Arg Arg Thr Thr
            180                 185

<210> SEQ ID NO 61
```

```
<211> LENGTH: 408
<212> TYPE: DNA
<213> ORGANISM: Pricamnia sp.
<220> FEATURE:
<221> NAME/KEY: CDS
<222> LOCATION: (1)..(408)

<400> SEQUENCE: 61 atg gct gat tat cgc caa gga ttt caa caa caa ccc act gaa gct ttc      48
Met Ala Asp Tyr Arg Gln Gly Phe Gln Gln Gln Pro Thr Glu Ala Phe
1               5                   10                  15 aaa ggc ctt ctt cct gaa agg gct ccc tcc aag tca caa gta ctg gct      96
Lys Gly Leu Leu Pro Glu Arg Ala Pro Ser Lys Ser Gln Val Leu Ala
            20                  25                  30 gtt gtc act ctc tta cct gtt ggt ggg act cta ctc cta ctt gca ggc     144
Val Val Thr Leu Leu Pro Val Gly Gly Thr Leu Leu Leu Leu Ala Gly
        35                  40                  45 ctc gtt ctt gct ggc act ctc att ggg ctc gct ctc aca acc cca ctt     192
Leu Val Leu Ala Gly Thr Leu Ile Gly Leu Ala Leu Thr Thr Pro Leu
    50                  55                  60 ttc ttg tta ttc agc cca ata ctt gtc cct gcg gtt gta gta gtt ggc     240
Phe Leu Leu Phe Ser Pro Ile Leu Val Pro Ala Val Val Val Val Gly
65                  70                  75                  80 ttg gct gtg atg ggg ttt ctt gca tcg gga gct ttt ggc atc aca tca     288
Leu Ala Val Met Gly Phe Leu Ala Ser Gly Ala Phe Gly Ile Thr Ser
                85                  90                  95 ctt tcc tca ctg tct tgg atg gtc aag tat ctg cgg caa agc agg gcc     336
Leu Ser Ser Leu Ser Trp Met Val Lys Tyr Leu Arg Gln Ser Arg Ala
            100                 105                 110 cct gag tat atg gac cag gca aag cgg cgc gtg caa gaa acg gca ggt     384
Pro Glu Tyr Met Asp Gln Ala Lys Arg Arg Val Gln Glu Thr Ala Gly
        115                 120                 125 caa gtt ggg cga aag gcc cag taa                                     408
Gln Val Gly Arg Lys Ala Gln
    130                 135

<210> SEQ ID NO 62
<211> LENGTH: 135
<212> TYPE: PRT
<213> ORGANISM: Pricamnia sp.

<400> SEQUENCE: 62

Met Ala Asp Tyr Arg Gln Gly Phe Gln Gln Gln Pro Thr Glu Ala Phe
1               5                   10                  15

Lys Gly Leu Leu Pro Glu Arg Ala Pro Ser Lys Ser Gln Val Leu Ala
            20                  25                  30

Val Val Thr Leu Leu Pro Val Gly Gly Thr Leu Leu Leu Leu Ala Gly
        35                  40                  45

Leu Val Leu Ala Gly Thr Leu Ile Gly Leu Ala Leu Thr Thr Pro Leu
    50                  55                  60

Phe Leu Leu Phe Ser Pro Ile Leu Val Pro Ala Val Val Val Val Gly
65                  70                  75                  80

Leu Ala Val Met Gly Phe Leu Ala Ser Gly Ala Phe Gly Ile Thr Ser
                85                  90                  95

Leu Ser Ser Leu Ser Trp Met Val Lys Tyr Leu Arg Gln Ser Arg Ala
            100                 105                 110

Pro Glu Tyr Met Asp Gln Ala Lys Arg Arg Val Gln Glu Thr Ala Gly
        115                 120                 125

Gln Val Gly Arg Lys Ala Gln
    130                 135
```

```
<210> SEQ ID NO 63
<211> LENGTH: 501
<212> TYPE: DNA
<213> ORGANISM: Glycine max
<220> FEATURE:
<221> NAME/KEY: CDS
<222> LOCATION: (1)..(501)

<400> SEQUENCE: 63 atg gca acc att tct act gat caa cca aga gga tcc tac tcc tat gga        48
Met Ala Thr Ile Ser Thr Asp Gln Pro Arg Gly Ser Tyr Ser Tyr Gly
 1               5                  10                  15 acc tcc tat gga gca ccc tat gga acc acc tat gag acc aac agc agc        96
Thr Ser Tyr Gly Ala Pro Tyr Gly Thr Thr Tyr Glu Thr Asn Ser Ser
            20                  25                  30 att aac aac cct cct tca cgc caa acc gtg aag ttc ata act gct gca       144
Ile Asn Asn Pro Pro Ser Arg Gln Thr Val Lys Phe Ile Thr Ala Ala
        35                  40                  45 act att ggc atc aca ctc tta ctc ctg tct ggg ttg acc ctc aca ggc       192
Thr Ile Gly Ile Thr Leu Leu Leu Leu Ser Gly Leu Thr Leu Thr Gly
    50                  55                  60 act gtc ata ggt ttg atc att gca acc cct ctt ctt gtt atc ttc agc       240
Thr Val Ile Gly Leu Ile Ile Ala Thr Pro Leu Leu Val Ile Phe Ser
65                  70                  75                  80 ccc atc ctt gtc cct gct gcg ttt gtg ctg ttc ctg gtt gct tct ggc       288
Pro Ile Leu Val Pro Ala Ala Phe Val Leu Phe Leu Val Ala Ser Gly
                85                  90                  95 ttt ttg ttc tct ggg ggc tgt ggt gtg gct gcc att gct gct tta tct       336
Phe Leu Phe Ser Gly Gly Cys Gly Val Ala Ala Ile Ala Ala Leu Ser
            100                 105                 110 tgg att tac aac tac gtt tct ggg aac cag cct gcg ggt tct gac acc       384
Trp Ile Tyr Asn Tyr Val Ser Gly Asn Gln Pro Ala Gly Ser Asp Thr
        115                 120                 125 ctt gac tat gca aaa ggg tac ctt act gat aag gca agg gat gtg aag       432
Leu Asp Tyr Ala Lys Gly Tyr Leu Thr Asp Lys Ala Arg Asp Val Lys
    130                 135                 140 gag agg gca aag gat tat gga agt tat gct caa ggt aga att aat gag       480
Glu Arg Ala Lys Asp Tyr Gly Ser Tyr Ala Gln Gly Arg Ile Asn Glu
145                 150                 155                 160 gcc aca caa gga act tat taa                                           501
Ala Thr Gln Gly Thr Tyr
                165

<210> SEQ ID NO 64
<211> LENGTH: 166
<212> TYPE: PRT
<213> ORGANISM: Glycine max

<400> SEQUENCE: 64

Met Ala Thr Ile Ser Thr Asp Gln Pro Arg Gly Ser Tyr Ser Tyr Gly
 1               5                  10                  15

Thr Ser Tyr Gly Ala Pro Tyr Gly Thr Thr Tyr Glu Thr Asn Ser Ser
            20                  25                  30

Ile Asn Asn Pro Pro Ser Arg Gln Thr Val Lys Phe Ile Thr Ala Ala
        35                  40                  45

Thr Ile Gly Ile Thr Leu Leu Leu Leu Ser Gly Leu Thr Leu Thr Gly
    50                  55                  60

Thr Val Ile Gly Leu Ile Ile Ala Thr Pro Leu Leu Val Ile Phe Ser
65                  70                  75                  80
```

```
Pro Ile Leu Val Pro Ala Ala Phe Val Leu Phe Leu Val Ala Ser Gly
            85                  90                  95

Phe Leu Phe Ser Gly Gly Cys Gly Val Ala Ile Ala Ala Leu Ser
            100                 105                 110

Trp Ile Tyr Asn Tyr Val Ser Gly Asn Gln Pro Ala Gly Ser Asp Thr
            115                 120                 125

Leu Asp Tyr Ala Lys Gly Tyr Leu Thr Asp Lys Ala Arg Asp Val Lys
    130                 135                 140

Glu Arg Ala Lys Asp Tyr Gly Ser Tyr Ala Gln Gly Arg Ile Asn Glu
145                 150                 155                 160

Ala Thr Gln Gly Thr Tyr
                165
```

<210> SEQ ID NO 65
<211> LENGTH: 531
<212> TYPE: DNA
<213> ORGANISM: Helianthus Annuus
<220> FEATURE:
<221> NAME/KEY: CDS
<222> LOCATION: (1)..(531)

<400> SEQUENCE: 65

```
atg acg gac ata cac acc aaa gaa caa ggc cag caa cag tca cgt tgg     48
Met Thr Asp Ile His Thr Lys Glu Gln Gly Gln Gln Gln Ser Arg Trp
1               5                   10                  15 cat gta gaa cca caa cac caa agc cag cat tgg acc aca cag tcc caa     96
His Val Glu Pro Gln His Gln Ser Gln His Trp Thr Thr Gln Ser Gln
                20                  25                  30 cgc cag tgg aac gag ccc cgg gcc cac cag gtt gtg aaa gcg gcc acc    144
Arg Gln Trp Asn Glu Pro Arg Ala His Gln Val Val Lys Ala Ala Thr
            35                  40                  45 gcg gca gcg gtg ggt ggc tcg ctt ctc gtc ctg gcg ggc ctg gtg ctc    192
Ala Ala Ala Val Gly Gly Ser Leu Leu Val Leu Ala Gly Leu Val Leu
        50                  55                  60 gct ggg aca gtg atc gcg ctg aca cta gcg aca ccg gtg cta gtc ata    240
Ala Gly Thr Val Ile Ala Leu Thr Leu Ala Thr Pro Val Leu Val Ile
65                  70                  75                  80 ttt agc ccg gtg ctc gtg cca gcg ctg atc gct gtc ttt ctg ctg gtg    288
Phe Ser Pro Val Leu Val Pro Ala Leu Ile Ala Val Phe Leu Leu Val
                85                  90                  95 agc ggg ttt ttg acg tcg ggc ggg ttt ggt gtg gcc gcg gcg acg gtg    336
Ser Gly Phe Leu Thr Ser Gly Gly Phe Gly Val Ala Ala Ala Thr Val
            100                 105                 110 ttg gcg tgg atg tat cgg tat gtg acc ggg gag caa ccg agc ggt gcg    384
Leu Ala Trp Met Tyr Arg Tyr Val Thr Gly Glu Gln Pro Ser Gly Ala
        115                 120                 125 gat aca tcg gat gag gcg tcg cac agg ctc gga gcg aag gcg cgg gat    432
Asp Thr Ser Asp Glu Ala Ser His Arg Leu Gly Ala Lys Ala Arg Asp
130                 135                 140 att aag gac cga ggc gag cat gcg ggc cga ggg ggt cat tat gga acc    480
Ile Lys Asp Arg Gly Glu His Ala Gly Arg Gly Gly His Tyr Gly Thr
145                 150                 155                 160 gcg ggg gtt cat acg ggc gga ccc gga ggg gga gta ggt act tat gtt    528
Ala Gly Val His Thr Gly Gly Pro Gly Gly Gly Val Gly Thr Tyr Val
                165                 170                 175 tga                                                                 531
```

<210> SEQ ID NO 66
<211> LENGTH: 176
<212> TYPE: PRT

<213> ORGANISM: Helianthus Annuus

<400> SEQUENCE: 66

```
Met Thr Asp Ile His Thr Lys Glu Gln Gly Gln Gln Gln Ser Arg Trp
1               5                   10                  15

His Val Glu Pro Gln His Gln Ser Gln His Trp Thr Thr Gln Ser Gln
            20                  25                  30

Arg Gln Trp Asn Glu Pro Arg Ala His Gln Val Val Lys Ala Ala Thr
        35                  40                  45

Ala Ala Ala Val Gly Gly Ser Leu Leu Val Leu Ala Gly Leu Val Leu
50                  55                  60

Ala Gly Thr Val Ile Ala Leu Thr Leu Ala Thr Pro Val Leu Val Ile
65                  70                  75                  80

Phe Ser Pro Val Leu Val Pro Ala Leu Ile Ala Val Phe Leu Leu Val
                85                  90                  95

Ser Gly Phe Leu Thr Ser Gly Gly Phe Gly Val Ala Ala Ala Thr Val
            100                 105                 110

Leu Ala Trp Met Tyr Arg Tyr Val Thr Gly Glu Gln Pro Ser Gly Ala
        115                 120                 125

Asp Thr Ser Asp Glu Ala Ser His Arg Leu Gly Ala Lys Ala Arg Asp
130                 135                 140

Ile Lys Asp Arg Gly Glu His Ala Gly Arg Gly His Tyr Gly Thr
145                 150                 155                 160

Ala Gly Val His Thr Gly Gly Pro Gly Gly Val Gly Thr Tyr Val
            165                 170                 175
```

<210> SEQ ID NO 67
<211> LENGTH: 471
<212> TYPE: DNA
<213> ORGANISM: Pyrus sp.
<220> FEATURE:
<221> NAME/KEY: CDS
<222> LOCATION: (1)..(471)

<400> SEQUENCE: 67

```
atg gct gat cgt cca caa cca cac cag atc caa gtc cat ccc cac cac    48
Met Ala Asp Arg Pro Gln Pro His Gln Ile Gln Val His Pro His His
1               5                   10                  15 cgc tac gac ggc ggc gcc aag gga gga ggc cct tca gcc tcc aca gtc    96
Arg Tyr Asp Gly Gly Ala Lys Gly Gly Gly Pro Ser Ala Ser Thr Val
            20                  25                  30 ctc gcc gtc gtc acc ctt gtg cct ctc ggc ggc ttg ctg cta gga ctc    144
Leu Ala Val Val Thr Leu Val Pro Leu Gly Gly Leu Leu Leu Gly Leu
        35                  40                  45 gcc ggt ttg acg ctg gcg gtc acg ctc ttc ggc ctg gtg gtc tcc act    192
Ala Gly Leu Thr Leu Ala Val Thr Leu Phe Gly Leu Val Val Ser Thr
50                  55                  60 ccg gta ttc atc atc ttc agc ccc gtt ata gtg cca gca atc tta acc    240
Pro Val Phe Ile Ile Phe Ser Pro Val Ile Val Pro Ala Ile Leu Thr
65                  70                  75                  80 att ggt ctg gct gtc ctt gcc ttc ttg acc tct ggg gca ttt ggg ctc    288
Ile Gly Leu Ala Val Leu Ala Phe Leu Thr Ser Gly Ala Phe Gly Leu
                85                  90                  95 acg gct gtc tct tcg ctc aca tgg gcc tac gac tac cta cgc gag gtc    336
Thr Ala Val Ser Ser Leu Thr Trp Ala Tyr Asp Tyr Leu Arg Glu Val
            100                 105                 110 acc ggg ttc atg ccg gat cag att gac caa gct aag agg cgc atg cag    384
Thr Gly Phe Met Pro Asp Gln Ile Asp Gln Ala Lys Arg Arg Met Gln
        115                 120                 125
```

```
gat atg gct ggt tct gtg ggg cag aag aca aag gag ctg gga cag gaa       432
Asp Met Ala Gly Ser Val Gly Gln Lys Thr Lys Glu Leu Gly Gln Glu
    130                 135                 140 att caa agc agg tcc cga gaa caa ggg agg agg acg tga                   471
Ile Gln Ser Arg Ser Arg Glu Gln Gly Arg Arg Thr
145                 150                 155

<210> SEQ ID NO 68
<211> LENGTH: 156
<212> TYPE: PRT
<213> ORGANISM: Pyrus sp.

<400> SEQUENCE: 68

Met Ala Asp Arg Pro Gln Pro His Gln Ile Gln Val His Pro His His
1               5                   10                  15

Arg Tyr Asp Gly Gly Ala Lys Gly Gly Pro Ser Ala Ser Thr Val
            20                  25                  30

Leu Ala Val Thr Leu Val Pro Leu Gly Gly Leu Leu Leu Gly Leu
        35                  40                  45

Ala Gly Leu Thr Leu Ala Val Thr Leu Phe Gly Leu Val Val Ser Thr
    50                  55                  60

Pro Val Phe Ile Ile Phe Ser Pro Val Ile Val Pro Ala Ile Leu Thr
65                  70                  75                  80

Ile Gly Leu Ala Val Leu Ala Phe Leu Thr Ser Gly Ala Phe Gly Leu
                85                  90                  95

Thr Ala Val Ser Ser Leu Thr Trp Ala Tyr Asp Tyr Leu Arg Glu Val
            100                 105                 110

Thr Gly Phe Met Pro Asp Gln Ile Asp Gln Ala Lys Arg Arg Met Gln
        115                 120                 125

Asp Met Ala Gly Ser Val Gly Gln Lys Thr Lys Glu Leu Gly Gln Glu
    130                 135                 140

Ile Gln Ser Arg Ser Arg Glu Gln Gly Arg Arg Thr
145                 150                 155

<210> SEQ ID NO 69
<211> LENGTH: 187
<212> TYPE: PRT
<213> ORGANISM: Zea mays P21641

<400> SEQUENCE: 69

Met Ala Asp Arg Asp Arg Ser Gly Ile Tyr Gly Gly Ala His Ala Thr
1               5                   10                  15

Tyr Gly Gln Gln Gln Gln Gln Gly Gly Gly Gly Arg Pro Met Gly Glu
            20                  25                  30

Gln Val Lys Lys Gly Met Leu His Asp Lys Gly Pro Thr Ala Ser Gln
        35                  40                  45

Ala Leu Thr Val Ala Thr Leu Phe Pro Leu Gly Gly Leu Leu Leu Val
    50                  55                  60

Leu Ser Gly Leu Ala Leu Thr Ala Ser Val Val Gly Leu Ala Val Ala
65                  70                  75                  80

Thr Pro Val Phe Leu Ile Phe Ser Pro Val Leu Val Pro Ala Ala Leu
                85                  90                  95

Leu Ile Gly Thr Ala Val Met Gly Phe Leu Thr Ser Gly Ala Leu Gly
            100                 105                 110

Leu Gly Gly Leu Ser Ser Leu Thr Cys Leu Ala Asn Thr Ala Arg Gln
        115                 120                 125
```

```
Ala Phe Gln Arg Thr Pro Asp Tyr Val Glu Glu Ala Arg Arg Arg Met
    130                 135                 140

Ala Glu Ala Ala Ala Gln Ala Gly His Lys Thr Ala Gln Ala Gly Gln
145                 150                 155                 160

Ala Ile Gln Gly Arg Ala Gln Glu Ala Gly Thr Gly Gly Gly Ala Gly
                165                 170                 175

Ala Gly Ala Gly Gly Gly Gly Arg Ala Ser Ser
            180                 185

<210> SEQ ID NO 70
<211> LENGTH: 14
<212> TYPE: PRT
<213> ORGANISM: artificial sequence
<220> FEATURE:
<223> OTHER INFORMATION: Oleosin diagnostic sequence

<400> SEQUENCE: 70

Thr Pro Leu Phe Val Ile Phe Ser Pro Val Leu Val Pro Ala
1               5                   10

<210> SEQ ID NO 71
<211> LENGTH: 26
<212> TYPE: DNA
<213> ORGANISM: artificial sequence
<220> FEATURE:
<223> OTHER INFORMATION: Primer

<400> SEQUENCE: 71
atggcaacca tttctactga tcaacc                                          26

<210> SEQ ID NO 72
<211> LENGTH: 73
<212> TYPE: DNA
<213> ORGANISM: artificial sequence
<220> FEATURE:
<223> OTHER INFORMATION: Primer

<400> SEQUENCE: 72
tatattctag aaaaatgccg ccagcggaac tggcggctgt gggattagat taataagttc    60
cttgtgtggc ctc                                                       73
```

METHOD TO INCREASE HYDROPHOBIC COMPOUND TITER IN A RECOMBINANT MICROORGANISM

FIELD OF THE INVENTION

This invention is in the field of microbiology and molecular biology. A method of increasing the titer of hydrophobic/lipophilic compounds produced in a microorganism is provided. More specifically, recombinant expression of a plant oleosin gene in a microbial host cell increases the titer of hydrophilic/lipophilic compounds. Recombinant microbial expression of an oleosin gene significantly increases carotenoid titer in microbial host cells engineered to produce carotenoids.

BACKGROUND OF THE INVENTION

Engineering microbial production of many commercially useful products has both advantages and disadvantage when compared to traditional chemical routes or isolation from organisms that naturally produce the desired compound. Many of the advantages associated with recombinant microbial production over traditional chemical synthesis include 1) the ability to synthesize the desired compounds at ambient temperature (decreased energy costs), 2) use of less expensive, readily available, typically renewable, and less toxic raw materials, 3) the production of less environmental waste, 4) the ability to harness regioselective and stereoseletive chemistry frequently observed when using biological catalysts, and 5) decreased purification costs from organisms that naturally produce the desired compound, often in commercially insignificant amounts. However, recombinant microbial production of a desirable compound has some disadvantages as well, such as inadequate compound production, poor growth characteristics, inadequate precursor supply, catalyst robustness and stability, regulatory issues (use of antibiotic markers), and host cell toxicity issues observed as a result of genetic modification. One particular problem associated with producing hydrophobic/lipophilic compounds in many microorganisms is limited internal storage capacity. Many hydrophobic/lipophilic compounds tend to accumulate in internal hydrophobic compartments within the cell (for example, intracellular membranes). Accumulation of these materials within the various compartments tends to be limited, as excess accumulation may have adverse effects on the viability of the host organisms (i.e. disrupting normal membrane function, decreased growth, increased toxicity to host cell, etc.).

One method used to increase the storage capacity in recombinant host cells is to increase one or more storage components of the cell. Arechaga et al. (*FEBS Lett.* 482: 215-219 (2000); WO 01/29236 A1) describes a method to alter the intracytoplasmic membrane content and composition by expressing the b and/or c subunit of ATP synthase. Membrane proliferation was induced, allowing elevated expression of genes encoding membrane proteins. Arechaga et al. do not describe a method to increase the intracellular storage capacity of hydrophobic compounds produced in microorganisms, especially non-proteinaceous compounds.

The intracellular storage of hydrophobic compounds (such as oils) is known to naturally occur in some organisms. For example, many plants store triacylglycerides (TAG) in oil bodies. These oil bodies consist of a phospholipid monolayer stabilized primarily with a unique plant protein called oleosin, along with other minor proteins surrounding the TAG core. Oleosins have a thumbtack-like architecture, with the "shaft" portion consisting of hydrophobic amino acids and the head exhibiting an amphipathic structure (in *Biochemistry and Molecular Biology of Plants*, Buchanan, B., Gruissem, W. and Jones, R., eds., American Society of Plant Physiologists, Rockville, Md., 2000, pp 17-18). Oleosins are required for significant accumulation of TAG in the oil bodies. The recombinant expression of plant oleosins in microorganisms for storage of hydrophobic/lipophilic compounds has not been reported.

Many commercially valuable hydrophobic/lipophilic compounds are naturally produced in microorgansisms. Additionally, microorganisms can be genetically engineered to produce the desired molecules. Examples of these hydrophobic molecules include, but are not limited to, hydrophobic peptides and compounds derived from isoprene such as carotenoids, quinones, dolichols, tocopherols, fatty acids (i.e. omega-3 fatty acids), terpenes, steroids, chlorophylles, polyhydroxyalkanoates, and natural rubber. Based on their hydrophobic/lipophilic nature, many of these compounds accumulate or associate near or within the hydrophobic portions of cellular membranes, leading to changes in membrane structure which may result in the loss of cell viability (Sikkema et al., *Microbiol Rev.,* 59(2):201-222 (1995)). Accumulation of hydrophobic/lipophilic compounds, especially in recombinant microorganisms engineered to produce them at elevated levels, is frequently limited by the amount of internal storage capacity within the microorganism.

Carotenoids represent a class of hydrophobic compounds currently being produced in recombinant microorganisms. The genetics of carotenoid production are well-known and have been exploited to produce a variety of carotenoids in recombinant bacteria (Lee et al., *Chem Biol,* 10:453-462 (2003)). Various genetic modifications to the isoprenoid/carotenoid biosynthesis pathway have been employed to engineer bacteria, such as *E. coli*, to produce high levels of various carotenoids.

Carotenoids, such as β-carotene and astaxanthin, associate and/or aggregate with phospholipid monolayers and bilayers (Shibata et al., *Chem Phys Lipids,* 113:11-22 (2001)). As a result, the capacity to store carotenoids may ultimately be limited to the amount of available hydrophobic storage capacity. For example, it has been reported that one of the primary limitations associated with microbial carotenoid production, especially in bacteria such as *E. coli*, is the inability to accumulate commercially-useful levels of carotenoids, as is the case in many industrially suitable production hosts (Schmidt-Dannert, C. and Lee, P., *Appl Microbiol Biotechnol,* 60:1-11 (2002)).

It has been speculated that the limits for carotenoid production in a non-carotenogenic host, such as *E. coli*, had been reached at the level of around 1.5 mg/g dry cell weight due to overload of membranes and blocking of membrane functionality (although U.S. Ser. No. 10/735442 has recently reported levels up to about 6 mg/g dry cell weight). It has been suggested that the future focus of engineering *E. coli* for high levels of carotenoid production should be on formation of additional membranes and on genetic manipulations leading to novel carotenoid sequestering systems (Albrecht et al., *Biotechnol Lett,* 21:791-795 (1999)).

The problem to be solved therefore is to provide a method to increase the hydrophobic/lipophilic compound titer in a microbial cell, especially in recombinant microorganisms engineered to produce such compounds.

SUMMARY OF THE INVENTION

The stated problem has been solved by providing a method to increase hydrophobic/lipophilic compound titer in a microorganism by recombinantly expressing one or more plant oleosin genes. In plants, oleosins are known to stability storage of oil bodies. Expression of any plant oleosin gene is believed to increase the available hydrophobic/lipophilic storage capacity (as measured by a significant increase in hydrophobic/lipophilic compound titer) in the transformed microbial host cell. Specifically, recombinant *E. coli* cells capable of producing elevated levels of carotenoids were engineered to express plant oleosin genes, resulting in a significant increase in the titer of several recombinantly produced carotenoids.

Oleosins can be identified by the existence of a diagnostic motif as represented by SEQ ID NO: 70. An amino acid sequence analysis of numerous oleosins obtained from a variety of sources indicates that suitable oleosins can be identified as those comprised of a 14 amino acid sequence having at least 70% similarity to the diagnostic motif represented by SEQ ID NO: 70.

Accordingly, in one embodiment the invention provides a recombinant microbial production host for the production of hydrophobic compounds comprising:
  a) an intracellular system for the production of a hydrophobic compound; and
  b) at least one genetic construct encoding an oleosin polypeptide having an amino acid sequence comprising an oleosin diagnostic motif, said motif having about 70% identity to the amino acid sequence as set forth in SEQ ID NO: 70.

Hosts preferred in the present invention include, but are not limited to bacteria, yeast, and algae, and preferred polypeptides encoded by the oleosin encoding genetic construct are selected from the group consisting of SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68.

In another embodiment the invention provides a method for the production of a hydrophobic compound comprising:
  a) providing a recombinant microbial production host comprising:
    i) an intracellular system for the production of a hydrophobic compound; and
    ii) at least one genetic construct encoding an oleosin polypeptide having an amino acid sequence comprising an oleosin diagnostic motif, said motif having about 70% identity to the amino acid sequence as set forth in SEQ ID NO: 70; and
  b) growing the production host of (a) under conditions whereby a hydrophobic compound is produced.

In a similar embodiment the invention provides a method to increase the titer of a hydrophobic compound in a recombinant microbial host cell comprising:
  a) providing a transformed microbial host cell producing a hydrophobic compound, said host comprising:
    i) at least one genetic construct encoding an oleosin polypeptide having an amino acid sequence comprising an oleosin diagnostic motif, said motif having about 70% identity to the amino acid sequence as set forth in SEQ ID NO: 70; and
  b) growing the transformed microbial host cell of (a) under suitable growth conditions whereby the oleosin construct is expressed and whereby the titer of hydrophobic compound produced in said transformed microbial host cell is increased relative to the microbial host cell lacking said oleosin construct when grown under the similar conditions;
  d) optionally, recovering the hydrophobic compound produced by said transformed microbial host cell in c).

In an additional embodiment the invention provides an isolated polynucleotide encoding an oleosin having the amino acid sequence selected from the group consisting of SEQ ID NO: 40, SEQ ID NO: 42, SEQ ID NO: 44, SEQ ID NO: 46, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, and SEQ ID NO: 68.

Similarly the invention provides an isolated polynucleotide selected from the group consisting of SEQ ID NO: 39, SEQ ID NO: 41, SEQ ID NO: 43, SEQ ID NO: 45, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, and SEQ ID NO: 67.

BRIEF DESCRIPTION OF THE FIGURES AND SEQUENCE DESCRIPTIONS

Figure 1:
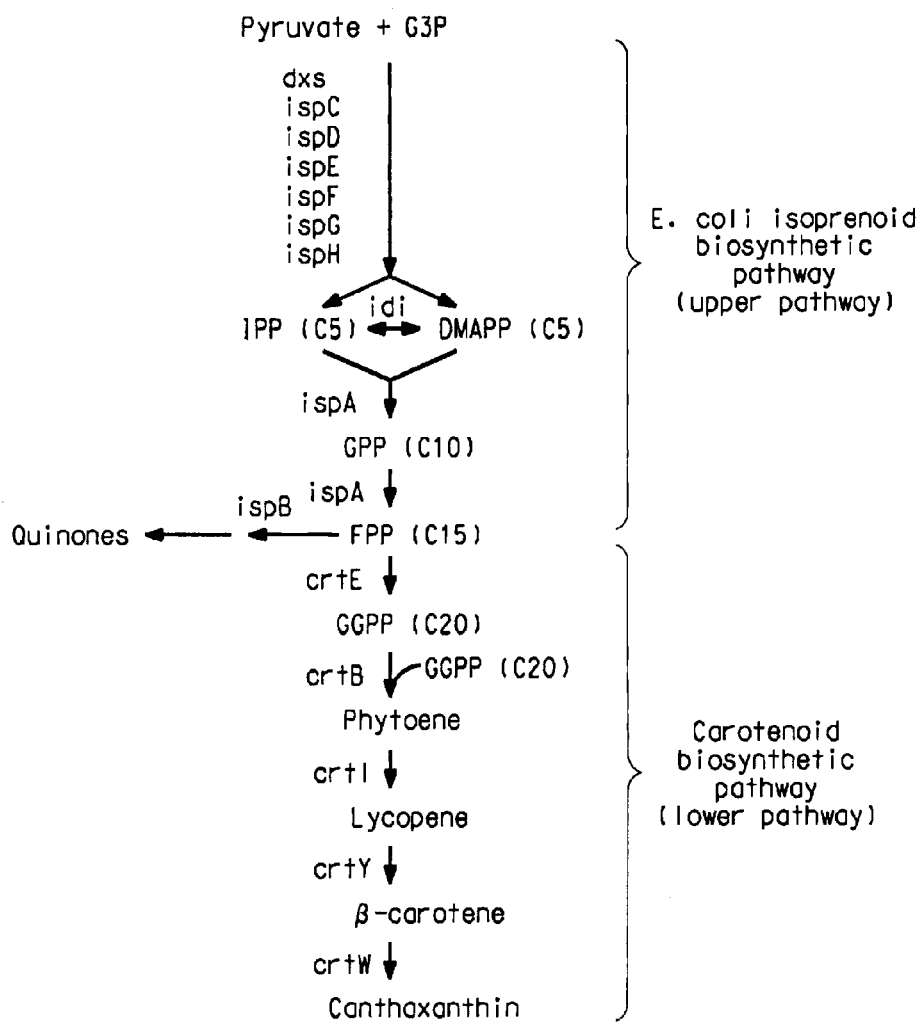

FIG. 1 shows the isoprenoid biosynthesis pathway in *E. coli*.

Figure 2B:
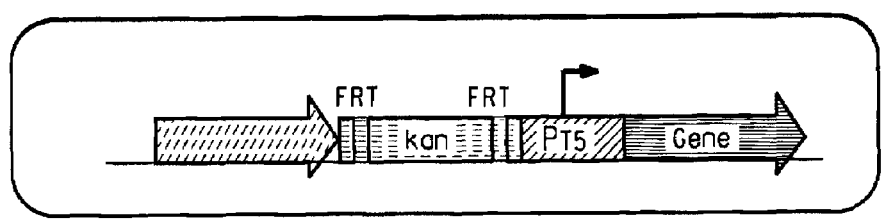
Figure 2B:
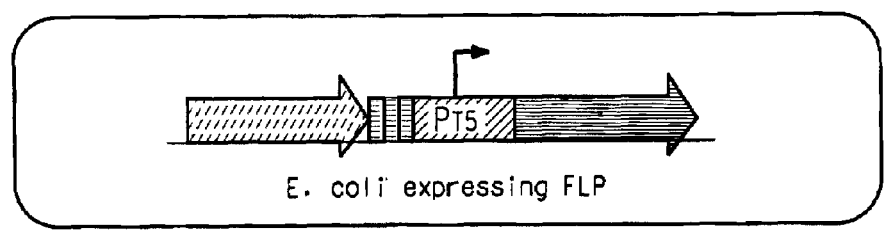

FIG. 2 shows the two PCR fragment method for integration of a strong promoter upstream of isoprenoid genes in the *E. coli* chromosome (U.S. Ser. Nos. 10/734936 and 10/735442; hereby incorporated by reference). The method is exemplified by replacing the native promoter of the idi gene with the strong promoter $P_{T5}$.

FIG. 3 shows the Clustal alignment of several publicly available oleosin genes and the identification of several conversed amino acids.

The invention can be more fully understood from the following detailed description, biological deposits, and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleic acid sequence of the coding region of the *Pantoea stewartii* crtE gene.

SEQ ID NO: 2 is the deduced amino acid sequence of the *Pantoea stewartii* CrtE enzyme.

SEQ ID NO: 3 is the nucleic acid sequence of the coding region of the *Pantoea stewartii* crtX gene.

SEQ ID NO: 4 is the deduced amino acid sequence of the *Pantoea stewartii* CrtX enzyme.

SEQ ID NO: 5 is the nucleic acid sequence of the coding region of the *Pantoea stewartii* crtY gene.

SEQ ID NO: 6 is the deduced amino acid sequence of the *Pantoea stewartii* CrtY enzyme.

SEQ ID NO: 7 is the nucleic acid sequence of the coding region of the *Pantoea stewartii* crtI gene.

SEQ ID NO: 8 is the deduced amino acid sequence of the *Pantoea stewartii* CrtI enzyme.

SEQ ID NO: 9 is the nucleic acid sequence of the coding region of the *Pantoea stewartii* crtB gene.

SEQ ID NO: 10 is the deduced amino acid sequence of the *Pantoea stewartii* CrtB enzyme.

SEQ ID NO: 11 is the nucleic acid sequence of the coding region of the *Pantoea stewartii* crtZ gene.

SEQ ID NO: 12 is the deduced amino acid sequence of the *Pantoea stewartii* CrtZ enzyme.

SEQ ID NO:13-14 are oligonucleotide primers used to amplify the carotenoid biosynthetic genes from *P. stewartii*.

SEQ ID NO:15 is the nucleotide sequence for the $P_{T5}$ promoter.

SEQ ID NO:16 is the nucleic acid sequence of primer 5'-kan(dxs).

SEQ ID NO:17 is the nucleic acid sequence of primer 5'-kan(idi).

SEQ ID NO:18 is the nucleic acid sequence of primer 5'-kan(ispDF).

SEQ ID NO:19 is the nucleic acid sequence of primer 3'-kan.

SEQ ID NO:20 is the nucleic acid sequence of primer 5'-T5.

SEQ ID NO:21 is the nucleic acid sequence of primer 3'-T5(dxs).

SEQ ID NO:22 is the nucleic acid sequence of primer 3'-T5(idi).

SEQ ID NO:23 is the nucleic acid sequence of primer 3'-T5(ispDF).

SEQ ID NO:24 is the nucleotide sequence for plasmid pKD46.

SEQ ID NO:25 is the nucleotide sequence for plasmid pPCB15.

SEQ ID NO:26 is the nucleic acid sequence of primer T-kan.

SEQ ID NO:27 is the nucleic acid sequence of primer B-dxs.

SEQ ID NO:28 is the nucleic acid sequence of primer T-T5.

SEQ ID NO:29 is the nucleic acid sequence of primer B-idi.

SEQ ID NO:30 is the nucleic acid sequence of primer B-ispDF.

SEQ ID NO:31 is the nucleotide sequence of the wild-type β-carotene ketolase (crt) gene from *Agrobacterium aurantiacum*.

SEQ ID NO:32 is the nucleotide sequence of the codon-optimized β-carotene ketolase (crtW) gene from *Agrobacterium aurantiacum*.

SEQ ID NO:33 is the amino acid sequence of the β-carotene ketolase (CrtW) enzyme from *Agrobacterium aurantiacum*.

SEQ ID NO:34 is the nucleotide sequence of the crtYIB gene cluster from *Pantoea stewartii*.

SEQ ID NO:35 is the nucleic acid sequence of primer pBHRcrt_1F.

SEQ ID NO:36 is the nucleic acid sequence of primer pBHRcrt_1R.

SEQ ID NO:37 is the nucleic acid sequence of primer pBHRcrt_2F.

SEQ ID NO:38 is the nucleic acid sequence of primer pBHRcrt_2R.

SEQ ID NO:39 is the nucleic acid sequence of an oleosin gene identified in clone ids3c.pk011.e15 and denoted as OL3.

SEQ ID NO:40 is the deduced amino acid sequence of the OL3 oleosin protein.

SEQ ID NO:41 is the nucleic acid sequence of an oleosin gene identified in clone ceb7f.pk004.b6a and denoted as OL4.

SEQ ID NO:42 is the deduced amino acid sequence of the OL4 oleosin protein.

SEQ ID NO:43 is the nucleic acid sequence of an oleosin gene identified in clone ece1c.pk006.p7 and denoted as OL5.

SEQ ID NO:44 is the deduced amino acid sequence of the OL5 oleosin protein.

SEQ ID NO:45 is the nucleic acid sequence of an oleosin gene identified in clone ece1c.pk003.i24 and denoted as OL6.

SEQ ID NO:46 is the deduced amino acid sequence of the OL6 oleosin protein.

SEQ ID NO:47 is the nucleic acid sequence of an oleosin gene identified in clone vmb1na.pk002.f2 and denoted as OL7.

SEQ ID NO:48 is the deduced amino acid sequence of the OL7 oleosin protein.

SEQ ID NO:49 is the nucleic acid sequence of an oleosin gene identified in clone e eas1c.pk003.I3 and denoted as OL8.

SEQ ID NO:50 is the deduced amino acid sequence of the OL8 oleosin protein.

SEQ ID NO:51 is the nucleic acid sequence of an oleosin gene identified in clone ncs.pk0006.a2 and denoted as OL9.

SEQ ID NO:52 is the deduced amino acid sequence of the OL9 oleosin protein.

SEQ ID NO:53 is the nucleic acid sequence of an oleosin gene identified in clone vs1.pk0015.b7 and denoted as OL11.

SEQ ID NO:54 is the deduced amino acid sequence of the OL11 oleosin protein.

SEQ ID NO:55 is the nucleic acid sequence of an oleosin gene identified in clone egh1c.pk003.h3 and denoted as OL16.

SEQ ID NO:56 is the deduced amino acid sequence of the OL16 oleosin protein.

SEQ ID NO:57 is the nucleic acid sequence of an oleosin gene identified in clone ecs1c.pk007.g10 and denoted as OL17.

SEQ ID NO:58 is the deduced amino acid sequence of the OL17 oleosin protein.

SEQ ID NO:59 is the nucleic acid sequence of an oleosin gene identified in clone fds1n.pk018.c6 and denoted as OL18.

SEQ ID NO:60 is the deduced amino acid sequence of the OL18 oleosin protein.

SEQ ID NO:61 is the nucleic acid sequence of an oleosin gene identified in clone pps.pk0001.f6 and denoted as OL19.

SEQ ID NO:62 is the deduced amino acid sequence of the OL19 oleosin protein.

SEQ ID NO:63 is the nucleic acid sequence of an oleosin gene identified in clone sdp2c.pk001.o14 and denoted as OL20.

SEQ ID NO:64 is the deduced amino acid sequence of the OL20 oleosin protein.

SEQ ID NO:65 is the nucleic acid sequence of an oleosin gene identified in clone hls1c.pk009.c and denoted as OL23.

SEQ ID NO:66 is the deduced amino acid sequence of the OL23 oleosin protein.

SEQ ID NO:67 is the nucleic acid sequence of an oleosin gene identified in clone fds1n.pk018.I23 and denoted as OL24.

SEQ ID NO:68 is the deduced amino acid sequence of the OL24 oleosin protein.

SEQ ID NO:69 is the amino acid sequence of *Zea mays* oleosin ZM-II from GENBANK® Accession No. P21641.

SEQ ID NO:70 is the amino acid sequence of the conserved diagnostic motif (the "proline knot") useful for identifying oleosins suitable in the present invention.

SEQ ID NO: 71 is the nucleic acid sequence of primer ST-OL20.

SEQ ID NO: 72 is the nucleic acid sequence of primer SB-OL20(trpXbaI).

BRIEF DESCRIPTION OF BIOLOGICAL DEPOSITS

The following biological deposits were made under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Plasmid pCP20 | ATCC PTA-4455 | Jun. 13, 2002 |
| WS#124 *E. coli* strain $P_{T5}$-dxs $P_{T5}$-idi $P_{T5}$-ygbBP yjeR::Tn5, pPCB15 | ATCC PTA-4807 | Nov. 20, 2002 |
| WS#208 *E. coli* strain $P_{T5}$-dxs $P_{T5}$-idi $P_{T5}$-ygbBP $P_{T5}$-ispB, pDCQ108 | ATCC PTA-4823 | Nov. 26, 2002 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

In this disclosure, a number of terms and abbreviations are used. The following definitions are provided.

As used herein, the terms "comprising" means the presence of the stated features, integers, steps, or components as referred to in the claims, but that it does not preclude the presence or addition of one or more other features, integers, steps, components or groups thereof.

"Open reading frame" is abbreviated ORF.

"Polymerase chain reaction" is abbreviated PCR.

As used herein, the terms "hydrophobic compound", "lipophilic compound", and "hydrophobic/lipophilic compound" will be used interchangeably to described a molecule that has limited solubility in water and tends to have an affinity and/or accumulate with other hydrophobic molecules, such as the fatty acid portion of lipid molecules. As used herein, "lipid" refers to an organic compound including fats, oils, waxes, sterols, and glycerides that are insoluble in water but soluble in organic solvents. Typical examples of hydrophobic/lipophilic molecules include, but are not limited to, hydrophobic peptides, isoprenoids, carotenoids, quinones, dolichols, tocopherols, fatty acids (i.e. omega-3 fatty acids) and and their esters, terpenes, steroids, chlorophylles, polyhydroxyalkanoates, and natural rubber.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, the term "isoprenoid" or "terpenoid" refers to the compounds and any molecules derived from the isoprenoid pathway, including 10, 15 and 20 carbon terpenoids and their derivatives, as well as carotenoids and xanthophylls.

The term "Dxs" refers to the enzyme D-1-deoxyxylulose 5-phosphate synthase encoded by the dxs gene which catalyzes the condensation of pyruvate and D-glyceraldehyde 3-phosphate to D-1-deoxyxylulose 5-phosphate (DOXP).

The term "YgbP", recently renamed as "IspD", refer to the enzyme encoded by the ispD gene that catalyzes the CTP-dependent cytidylation of 2-C-methyl-D-erythritol-4-phosphate to 4-diphophocytidyl-2C-methyl-D-erythritol.

The term "YgbB" has also been renamed "IspF" and refers to the enzyme encoded by the ispF gene that catalyzes the cyclization with loss of CMP of 4-diphophocytidyl-2C-methyl-D-erythritol to 4-diphosphocytidyl-2C-methyl-D-erythritol-2-phosphate to 2C-methyl-D-erythritol-2,4-cyclodiphosphate.

The term "Idi" refers to the enzyme isopentenyl diphosphate isomerase encoded by the *E. coli* idi gene that converts isopentenyl diphosphate to dimethylallyl diphosphate.

The term "LytB" refers to the enzyme involved in conversion of 2C-methyl-D-erythritol-2,4-cyclodiphosphate to dimethylallyl diphosphate (DMAPP) and isopentenyl diphosphate (IPP) encoded by the lytB gene (recently renamed ispH).

The term "GcpE" refers to the enzyme involved in conversion of 2C-methyl-D-erythritol-2,4-cyclodiphosphate to dimethylallyl diphosphate (DMAPP) and isopentenyl diphosphate (IPP) encoded by the *E. coli* gcpE gene (recently renamed ispG).

The term "IspA" refers to the enzyme FPP synthase encoded by the ispA gene that forms farnesyl pyrophosphate (FPP).

As used herein, the term "pPCB15" refers to the plasmid (SEQ ID NO: 25) comprising the *Pantoea stewarti* β-carotene synthesis genes (crtEXYIB), used as a reporter plasmid for monitoring β-carotene production in recombinant *E. coli*.

As used herein, the term "pDCQ108" refers to the plasmid containing β-carotene synthesis genes *Pantoea* crtEXYIB used as a reporter plasmid for monitoring β-carotene production in *E. coli*. This plasmid has been previously deposited to the American Type Culture Collection (ATCC PTA4823) in *E. coli* strain WS#208. Briefly, pDCQ108 is a tetracycline resistant derivative of pBHR1-crt1 carrying crtEXYIB gene cluster that produces β-carotene. The tetracycline resistant gene was introduced by in vitro Tn5 insertion using Epicentre EZ-TN<TET> kit (Madison, Wis.). The original kanamycin resistant gene on pBHR-crt1 was partially deleted.

As used herein, the term "pBHR-crt1" refers to a plasmid comprised of the *Pantoea stewartii* (crtEXYIB) gene cluster (U.S. Ser. No. 10/209372; hereby incorporated by reference). Briefly, a 6.3 kb EcoRI fragment containing the crt gene cluster (crtEXYIB) was cloned into broad-host range vector pBHR1 (MoBiTec, LLC, Marco Island, Fla.) to form pBHR-crt1. The *E. coli* strain with pBHR-crt1 containing the wild type crtEXYIB gene cluster produced β-carotene.

The chloramphenicol resistance gene promoter on pBHR1 vector directed the functional expression of the crt genes.

As used herein, the term "pKD46" refers to the plasmid (SEQ ID NO: 24; Datseniko and Wanner, supra) having GENBANK® Accession number AY048746. Plasmid pKD46 expresses the components of the λ-Red Recombinase system.

As used herein, the term "expressible DNA fragment" means any DNA that influences phenotypic changes in the host cell. An "expressible DNA fragment" may include for example, DNA comprising regulatory elements, isolated promoters, open reading frames, genes, or combinations thereof.

As used herein, the terms "$P_{T5}$ promoter" and "$P_{T5}$" refers to the nucleotide sequence that comprises the −10 and −35 consensus sequences, lactose operator (lacO), and ribosomal binding site (rbs) from phage T5 (SEQ ID NO: 15).

As used herein, the term "carotenoid overproducing bacteria" refers to bacteria of the invention which has been genetically modified by the up-regulation or down-regulation of various genes to produce a carotenoid compound a levels greater than the wildtype or unmodified host.

As used herein, the term "*E. coli*" refers to *Escherichia coli* strain K-12 derivatives, such as MG1655 (ATCC 47076) and MC1061 (ATCC 53338).

The term "*Pantoea stewartii* subsp. *stewartii*" is abbreviated as "*Pantoea stewartii*" and is used interchangeably with *Erwinia stewartii* (Mergaert et al., *Int J. Syst. Bacteriol.*, 43:162-173 (1993)).

The term "*Pantoea ananatas*" is used interchangeably with *Erwinia uredovora* (Mergaert et al., supra)

As used herein, the term "*Pantoea* crtEXYIB cluster" refers to a gene cluster containing carotenoid synthesis genes crtEXYIB amplified from *Pantoea stewartii* ATCC 8199. The gene cluster is comprised of the genes crtE, crtX, crtY, crtI, and crtB. The cluster also contains a crtZ gene organized in opposite direction and adjacent to the crtB gene.

As used herein, the term "CrtE" refers to geranylgeranyl pyrophosphate synthase enzyme encoded by crtE gene which converts trans-trans-farnesyl diphosphate+isopentenyl diphosphate to pyrophosphate+geranylgeranyl diphosphate.

As used herein, the term "CrtY" refers to lycopene cyclase enzyme encoded by crtY gene which converts lycopene to β-carotene.

As used herein, the term "CrtI" refers to phytoene dehydrogenase enzyme encoded by crtI gene which converts phytoene into lycopene via the intermediaries of phytofluene, zeta-carotene and neurosporene by the introduction of 4 double bonds As used herein, the term "CrtB" refers to phytoene synthase enzyme encoded by crtB gene which catalyzes reaction from prephytoene diphosphate (geranylgeranyl pyrophosphate) to phytoene.

As used herein, the term "CrtX" refers to zeaxanthin glucosyl transferase enzyme encoded by crtX gene which converts zeaxanthin to zeaxanthin-β-diglucoside.

As used herein, the term "CrtZ" refers to a carotenoid hydroxylase enzyme (e.g. β-carotene hydroxylase) encoded by the crtZ gene which catalyzes a hydroxylation reaction. The oxidation reaction adds a hydroxyl group to cyclic carotenoids having a β-ionone type ring. This reaction converts cyclic carotenoids, such as β-carotene or canthaxanthin, into the hydroxylated carotenoids zeaxanthin or astaxanthin, respectively. Intermediates in the process typically include β-cryptoxanthin and adonirubin. CrtZ hydroxylases typically exhibit substrate flexibility, enabling production of a variety of hydroxylated carotenoids depending upon the available substrates.

As used herein, the term "CrtW" refers to a β-carotene ketolase enzyme encoded by the crtW gene which catalyzes an oxidation reaction where a keto group is introduced on the β-ionone type ring of cyclic carotenoids. This reaction converts cyclic carotenoids, such as β-carotene or zeaxanthin, into the ketocarotenoids canthaxanthin or astaxanthin, respectively. Intermediates in the process typically include echinenone and adonixanthin. CrtW ketolases typically exhibit substrate flexibility.

As used herein, the terms "upper isoprenoid pathway", "upper pathway", "isoprenoid pathway", and "*E. coli* isoprenoid biosynthetic pathway" will be use interchangeably and will refer to enzymes involved in converting pyruvate and glyceraldehyde-3-phosphate (G3P) to farnesyl pyrophosphate (FPP). These enzymes are encoded by genes that include, but are not limited to: the "dxs" gene (encoding 1-deoxyxylulose-5-phosphate synthase); the "ispC" gene (encoding 1-deoxyxylulose-5-phosphate reductoisomerase; also known at dxr); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "ispH" gene (also known as lytB) involved in the formation of dimethylallyl diphosphate; the "ispG" gene (also known as gcpE) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase). As used herein, the terms "lower carotenoid biosynthetic pathway", "carotenoid biosynthesis pathway", and "lower pathway" will be used interchangeably and refer to those enzymes which convert FPP to a suite of carotenoids. These enzymes are encoded by genes that include, but are not limited to: crtA, crtB, crtC, crtD, crtE, crtI, crtL, crtM, crtN, crtO, crtR, crtU, crtW, crtX, crtY, and crtZ. Finally, the term "lower carotenoid biosynthetic enzyme" is a term referring to one or more of the enzymes in the present lower pathway including, but not limited to CrtA, CrtB, CrtC, CrtD, CrtE, CrtI, CrtL, CrtM, CrtN, CrtO, CrtR, CrtU, CrtW, CrtX, CrtY, and CrtZ. In the present invention, the "lower pathway" genes necessary to produce β-carotene (crtE, crtY, crtI, and crtB) are expressed on reporter plasmids pPCB15 or pDCQ108.

As used herein, the term "helper plasmid" refers to either pKD46 (encoding λ-Red recombinase) or pCP20 (ATCC PTA-4455; encoding FLP site-specific recombinase (Datsenko and Wanner, *PNAS.* 97:6640-6645 (2000)).

As used herein, the terms "λ-Red recombinase system", "λ-Red system", and "λ-Red recombinase" are used interchangeably and refer to three essential genes, exo, bet, and gam, that are contained on a helper plasmid, pKD46 (Datsenko and Wanner, supra; SEQ ID NO:24).

As used herein, the term "homology arm" refers to a portion of a nucleic acid molecule having a nucleotide sequence that enables homologous recombination between two nucleic acids having substantially the same nucleotide sequence in a particular region of two different nucleic acids. The preferred size range of the homology arm is from about 10 to about 50 nucleotides in length.

As used herein, the term "triple homologous recombination" in the present invention refers to a genetic recombination between two linear DNA nucleotides and the target chromosome via their homologous sequences resulting in chromosomal integration of two linear nucleic acid molecules into the target of chromosome.

As used herein, the term "site-specific recombinase" is used in the present invention to describe a system comprised of one or more enzymes which recognize specific nucleotide sequences (recombination target sites) and which catalyze recombination between the recombination target sites. Site-specific recombination provides a method to rearrange, delete, or introduce exogenous DNA. Examples of site-specific recombinases and their associated recombination target sites are flippase (FLP/FRT), Cre-lox, R/RS, Gin/gix, Xer/dif, and Int/att. In the present invention, a site-specific recombinase was used to remove selectable markers. Antibiotic resistance markers, flanked on both sides by FRT recombination target sites, are removed by expression of the FLP site-specific recombinase. This method is used so that the numbers of chromosomal modifications necessary for microbial pathway engineering is not limited to the number of available selection markers (Huang et al., *J. Bacteriol.*, 179(19): 6076-6083 (1997)).

As used herein, the terms "transduction" and "generalized transduction" are used interchangeably and refer to a phenomenon in which bacterial DNA is transferred from one bacterial cell (the donor) to another (the recipient) by a phage particle containing bacterial DNA.

As used herein, the terms "P1 donor cell" and "donor cell" are used interchangeably and refer to a bacterial strain susceptible to infection by a bacteriophage or virus, and which serves as a source for the nucleic acid fragments packaged into the transducing particles. Typically, the genetic make up of the donor cell is similar or identical to the "recipient cell" which serves to receive P1 lysate containing transducing phage or virus produced by the donor cell.

As used herein, the terms "P1 recipient cell" and "recipient cell" are used interchangeably and refer to a bacterial strain susceptible to infection by a bacteriophage or virus and which serves to receive lysate containing transducing phage or virus produced by the donor cell.

As used herein, the terms "stacking", "combinatorial stacking", "chromosomal stacking", and "trait stacking" are used interchangeably and refer to the repeated process of stacking multiple genetic traits into one *E. coli* host using the bacteriophage P1 in combination with the site-specific recombinase system for removal of selection markers (U.S. Ser. No. 10/734778; hereby incorporated by reference).

As used herein, the terms "parallel combinatorial fashion" and "combinatorial fashion" are used interchangeably and refer to the P1 transduction with the P1 lysate mixture made from various donor cells, so that multiple genetic traits can be moved to the recipient cell in parallel (U.S. Ser. No. 10/734778).

As used herein, the terms "integration cassette" and "recombination element" refer to a linear nucleic acid construct useful for the transformation of a recombination proficient bacterial host. Recombination elements of the invention may include a variety of genetic elements such as selectable markers, functional DNA fragments, and recombination regions having homology to regions on a bacterial chromosome or on other recombination elements. Functional DNA fragments can include coding sequences, genes, gene clusters, sequences encoding functional RNA, promoters, and other regulatory elements specifically engineered into the recombination element to impart a desired phenotypic change upon recombination.

As used herein, the terms "inter-operon chromosomal integration site" or "inter-operon region" refer to a chromosomal site where integration of exogenous DNA using the current invention is targeted and where integration of the exogenous DNA will not disrupt the functionality of an endogenous operon within the host.

As used herein, the term "carotenoid biosynthesis enzyme" is an inclusive term referring to any and all of the enzymes known to be involved in carotenoid biosynthesis (converting farnesyl pyrophosphate to the desired carotenoid end product). These enzymes include, but are not limited to Ald, Sqs, Bkt, CrtA, CrtB, CrtC, CrtD, CrtE, CrtF, CrtI, CrtL, CrtM, CrtN1, CrtN2, CrtN3, CrtO, CrtR, CrtU, CrtW, CrtX, CrtY, and CrtZ. The term "carotenoid biosynthesis gene" is an inclusive term referring to any and all of the genes encoding carotenoid biosynthesis enzymes. These gene include, but are not limited to ald, sqs, bkt, crtA, crtB, crtC, crtD, crtE, crtF, crtI, crtL, crtM, crtN1, crtN2, crtN3, crtO, crtR, crtU, crtW, crtX, crtY, and crtZ.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genetic construct" is a non-limiting term meaning any contiguous series of nucleic acids capable of being expressed in a host organism. A genetic construct may include but is not limited to an open reading frame, an open reading frame operably linked to regulatory sequences, or a wildtype or mutant gene. Genetic constructs may encode poylpeptides or be nucleic acid fragments or molecules that are oriented for antisense expression.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe. In one aspect, nucleic acid fragments that hybridize to at least one of the present oleosin genes are suitable in the present methods.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods including, but not limited to, those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp, *CABIOS.*, 5:151-153 (1989)) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

"Codon degeneracy" refers to the nature in the genetic code permitting variation of the nucleotide sequence without effecting the amino acid sequence of an encoded polypeptide. Accordingly, the present methods use any nucleic acid fragment that encodes the amino acid sequence encoding oleosin polypeptides as set forth in SEQ ID NOs: 40, 42, 44, 46, 48, 50, 52, 54, 56, 58, 60, 62, 64, 66, 68, and 70. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "genetic end product" means the substance, chemical or material that is produced as the result of the activity of a gene product. Typically a gene product is an enzyme and a genetic end product is the product of that enzymatic activity on a specific substrate. A genetic end product may the result of a single enzyme activity or the result of a number of linked activities such as is found in an enzyme pathway.

"Operon", in bacterial DNA, is a cluster of contiguous genes transcribed from one promoter that gives rise to a polycistronic mRNA.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions ("inducible promoters").

The "3' non-coding sequences" refer to DNA sequences located downstream of a coding sequence and include sequences encoding regulatory signals capable of affecting mRNA processing or gene expression.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein, "transformation" refers to the transfer of a nucleic acid fragment into the genome of a host organism, resulting in genetically stable inheritance. As used herein, the host cell genome includes both chromosomal or extra-chromosomal (i.e. a vector) genes with the host cell. Host organisms containing the transformed nucleic acid fragments are referred to as "transgenic" or "recombinant" or "transformed" organisms. The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y. Within the context of this application it will be understood that where sequence analysis software is used for analysis, that the results of the analysis will be based on the "default values" of the program referenced, unless otherwise specified. As used herein "default values" will mean any set of values or parameters (as set by the software manufacturer) which originally load with the software when first initialized unless otherwise specified.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-lnterscience (1987).

Oleosins

Many plants store triacylglycerides (TAG) in oil bodies (typically about 0.5 to about 2.0 μm in diameter). Oleosins are "T"-shaped plant proteins responsible for the maintenance of size and structural integrity of oil bodies found in plants (Napier, J. et al., "The Seed Oleosins: Structure, Properties, and Biological Role" in *Advances in Botanical Research* incorporating *Advances in Plant Pathology* Vol 35. 111-138 (2001), Ed. J. Callow, Academic Press Ltd., London, England). Oleosins are alkaline proteins of low molecular mass, typical about 15-26 kDa (Huang, A., "Oil bodies and oleosins in seeds", in *Annual Review of Plant Physiology and Plant Molecular Biology* Vol. 43:177-200 (1992), Briggs, W., Jones, R., and Walbot, V. (Editors), Annual Reviews Inc., Palo Alto, Calif.). Oleosins are found in all oil-storing seeds. Amino acid sequence analysis of oleosins reveals that they are relatively conserved with most of the similarity present in the central hydrophobic domain of the protein (typically about 68-74 hydrophobic amino acids in length flanked by N- and C-terminal regions that are less hydrophobic and less conserved (Huang, A., supra). The central hydrophobic region is comprised of a highly conserved proline motif (the "proline knot"), providing the turn in α-helices to form an anti-parallel helical structure (Huang, A., supra). The proline knot is comprised of 3 proline residues and at least one serine residue within a 12-14 amino acid sequence forming the loop of the antiparallel β-strand structure. The amino acid sequence of the conserved central hydrophobic region is therefore useful for identifying plant oleosins (SEQ ID NO: 70).

In the present invention, a variety of oleosins were recombinantly expressed in a bacterial host cell engineered to produce hydrophobic/lipophilic compounds. Expression of one or more plant oleosins genes in the host cell resulted in a significant increase (typically at least about 2-fold) in the titer of the measured carotenoid. The effect appears to be associated with the recombinant expression of any oleosin gene. Consequently, any plant oleosin gene is suitable in the present invention. In one embodiment, an oleosin is defined as any protein, natural or synthetic, that includes a 60 to 80 amino acid-long fragment that can be aligned with the sequence segment of the Corn Oleosin Zm-II (GENBANK® accession number P21641; SEQ ID NO: 69) segment extending from position 50 to 120, having more than 25% amino acid identity over that segment and sharing 8 or more of the 13 conserved amino acids listed in Table 9.

Alternatively, oleosins can be identified by the highly conserved "proline knot" structure having the amino acid sequence represented by SEQ ID NO: 70 ("diagnostic amino acid sequence"). As described herein, this sequence is about 14 amino acids in length. Oleosin genes encoding a polypeptide comprised of the "proline knot" diagnostic amino acid sequence are suitable in the present invention. In one embodiment, suitable oleosins genes are those encoding a polypeptide comprised of an amino acid sequence having at least about 50% identity and/or 70% similarity to the diagnostic sequence represented by SEQ ID NO: 70. In another embodiment, suitable oleosins have at least about 55% amino acid sequence identity and/or 75% similarity to SEQ ID NO: 70. In a further embodiment, suitable oleosins have about at least 70% identity and/or 90% similarity to SEQ ID NO: 70.

In another embodiment, suitable oleosin genes encode polypeptides having an amino acid sequence selected from the group consisting of SEQ ID NOs: 40, 42, 44, 46, 48, 50, 52, 54, 56, 58, 60, 62, 64, 66, 68, and 69.

In another embodiment, suitable oleosin genes are comprised of nucleic acid sequences selected from the group consisting of SEQ ID NOs: 39, 41, 43, 45, 47, 49, 51, 53, 55, 57, 59, 61, 63, 65, and 67.

Hydrophilic and Lipophilic Compound Production

The present invention relates to bacteria engineered for the production of hydrophobic and/or lipophilic compounds. Many bacteria, such as E. coli, have been genetically engineered to produce a variety of hydrophobic/lipophilic compounds. Examples of these compounds include, but are not limited to isoprenoids (including lipid soluble vitamins A, D, E, and K), carotenoids, quinones (i.e. ubiquinones), dolichols (i.e. polyprenols), tocopherols, fatty acids (i.e. omega-3 fatty acids), terpenes (i.e. monoterpenes, sesquiterpenes, diterpenes, and tetraterpenes), steroids, chlorophylles, polyhydroxyalkanoates, natural rubber (cis-polyisoprene), and hydrophobic peptides. Expression of oleosin genes in bacteria is believed to affect the hydrophobic/lipophilic compartment in the cell for example by increasing or stabilizing it. The highly conserved hydrophobic motif characteristic of all oleosins is believed to create an intracellular surface to which the recombinantly produced hydrophobic/lipophilic compounds bind. Expression of the oleosin proteins is believed to facilitate an increase in the hydrophobic/hydrophilic storage capacity of the bacterial cell.

In one aspect, the present method is used to increase the production of hydrophobic and/or lipophilic compounds in a microbial host cell. In another aspect, the hydrophobic/lipophilic compound is an isoprenoid compound. In yet another aspect, the isoprenoid compound is a carotenoid. In a further aspect, the carotenoid is selected from the group consisting of lycopene, β-carotene, zeaxanthin, canthaxanthin, astaxanthin, and lutein.

Carotenoid Biosynthesis

The ability to increase the titer of a hydrophobic/lipophilic compound by recombinantly expressing a plant oleosin in a microbial host cell is exemplified by the increased production of various carotenoids. Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (isopentenyl pyrophosphate, IPP). The term "carotenoid" actually includes both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (Armstrong, G., supra).

The genetics of carotenoid pigment biosynthesis are well known (Armstrong, G., in *Comprehensive Natural Products Chemistry*, Elsevier Press, volume 2, pp 321-352 (1999); Lee, P. and Schmidt-Dannert, C., *Appl Microbiol Biotechnol*, 60:1-11 (2002); Lee et al., *Chem Biol* 10:453-462 (2003)) with a focussed discussion on biosynthesis in plants and nutritional uses by Fraser, P. and Bramley, P. (*Progress in Lipid Research*, 43:228-265 (2004)). This pathway is extremely well studied in the Gram-negative, pigmented bacteria of the genera *Pantoea*, formerly known as *Erwinia*.

Isoprenoids constitute the largest class of natural products in nature, and serve as precursors for sterols (eukaryotic membrane stabilizers), gibberelinns and abscisic acid (plant hormones), menaquinone, plastoquinones, and ubiquinone (used as carriers for electron transport), tetrapyrroles as well as carotenoids and the phytol side chain of chlorophyll (pigments for photosynthesis). All isoprenoids are synthesized via a common metabolic precursor, isopentenyl pyrophosphate (IPP). Until recently, the biosynthesis of IPP was generally assumed to proceed exclusively from acetyl-CoA via the classical mevalonate pathway. However, the existence of an alternative, mevalonate-independent pathway for IPP formation has been characterized for eubacteria and a green alga.

Farnesyl pyrophosphate (FPP) synthesis is common in both carotenogenic and non-carotenogenic bacteria. *E. coli* do not normally contain the genes necessary for conversion of FPP to β-carotene. Because of this, an *E. coli* strain containing a reporter plasmid comprised of the additional genes necessary for β-carotene production was used. Enzymes in the subsequent carotenoid pathway used to generate carotenoid pigments from FPP precursor can be divided into two categories: carotene backbone synthesis enzymes and subsequent modification enzymes. The backbone synthesis enzymes include geranyl-geranyl pyrophosphate synthase (CrtE), phytoene synthase (CrtB), phytoene dehydrogenase (CrtI) and lycopene cyclase (CrtY/L), etc. The modification enzymes include ketolases, hydroxylases, dehydratases, glycosylases, etc.

*E. coli* is a convenient host for heterologous carotenoid production. Most of the carotenogenic genes from bacteria, fungi and higher plants can be functionally expressed in *E. coli* (Sandmann, G. *Trends in Plant Science*, 6:14-17 (2001)). Further, many genetic tools are available for use in *E. coli* and it is often used as a production host for large-scale bioprocesses.

*E. coli* has been recently genetically modified to create several strains capable of enhanced production of β-carotene. One of the strains has been shown to produce up to 6 mg β-carotene per gram of dry cell weight (U.S. Ser. No. 10/734778 and U.S. Ser. No. 10/735442; hereby incorporated by reference). In contrast, engineered strains of *Candida utilis* produce 7.8 mg of lycopene per gram of cell dry weight of lycopene (Sandmann, supra). It has been speculated in the past that the limits for carotenoid production in a non-carotenogenic host such as *E. coli* had been reached at the level of around 1.5 mg/g cell dry weight due to overload of the membranes and blocking of membrane functionality. Because of this, it has been suggested that the future focus of engineering *E. coli* for high levels of carotenoid production should be on formation of additional membranes (Albrecht et al., supra).

It has also been found that over-expression of a certain combination of carotenoid biosynthetic genes, will give an unexpectedly high level of carotenoid end product production. Examples of genes useful in this manner that are part of the isoprenoid/carotenoid biosynthetic pathway include, but are not limited to dxs, ispC, ispD, ispE, ispF, ispG, ispH, idi, ispA, and the ispB gene. When these genes are selectively over expressed under the control of a strong promoter the result is an unexpectedly high level of carotenoid production. It is important to note that it is the combination of the over-expression of these genes that has been shown to give the desired effect.

The enzyme pathway involved in the biosynthesis of carotenoids can be conveniently viewed in two parts, the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids (FIG. 1). The upper pathway is ubiquitous in many non-carotogenic microorganisms and in these cases it will only be necessary to introduce genes that comprise the lower pathway for the biosynthesis of the desired carotenoid. The key division between the two pathways concerns the synthesis of farnesyl pyrophosphate (FPP). Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common C5 isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135-140 (1993); Rohmer et al, *Biochem.* 295: 517-524 (1993); Schwender et al., *Biochem.* 316: 73-80 (1996); Eisenreich et al., *Proc. Natl. Acad. Sci. USA* 93: 6431-6436 (1996)).

The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209).

The product of ygbB gene converts 4-diphosphocytidyl-2C-methyl-D-erythritol 2-phosphate to 2C-methyl-D-erythritol 2,4-cyclodiphosphate. 2C-methyl-D-erythritol 2,4-cyclodiphosphate can be further converted into carotenoids in carotenoid biosynthesis pathway. Recently, ygbB gene was renamed as ispF as a part of isp gene cluster (SwissProt #P36663). The reaction catalyzed by YgbP enzyme is carried out in CTP dependent manner.

The enzymes encoded by the lytB and gcpE genes (and perhaps others) are thought to participate in the reactions leading to formation of isopentenyl pyrophosphate (IPP) and dimethylallyl pyrophosphate (DMAPP).

IPP may be isomerized to DMAPP via IPP isomerase, encoded by the idi gene, however this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the Applicants consider the first step in the lower carotenoid biosynthetic pathway to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene, which imparts a "red" colored spectra, is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. In the present invention, a reporter plasmid is used which produces β-carotene as the genetic end product. However, additional genes may be used to create a variety of other carotenoids. For example as presented later, β-carotene can converted to canthaxanthin by a β-carotene ketolase encoded by the crtW, bkt, or crtO genes.

In one embodiment, the source of crt genes are primarily from *Pantoea stewartii*. Sequences of these preferred genes are presented as the following SEQ ID numbers: the crtE gene (SEQ ID NO:1), the crtX gene (SEQ ID NO:3), crtY (SEQ ID NO:5), the crtI gene (SEQ ID NO:7), the crtB gene (SEQ ID NO:9) and the crtZ gene (SEQ ID NO:11).

By using various combinations of the carotenoid biosynthesis genes, innumerable different carotenoids and carotenoid derivatives can be made, provided sufficient sources of FPP are available in the host organism. For example, the gene cluster crtEXYIB enables the production of β-carotene. Addition of the crtZ to crtEXYIB enables the production of zeaxanthin, while the crtEXYIBZO cluster leads to production of astaxanthin and canthaxanthin.

It is envisioned that expression of one or more oleosin genes in the recombinant microbial host cell (capable of producing a carotenoid) will increase the overall titer of any $C_{30}$ or $C_{40}$ carotenoid compound as defined herein including, but not limited to, antheraxanthin, adonixanthin, astaxanthin, canthaxanthin, capsorubrin, β-cryptoxanthin, didehydrolycopene, didehydrolycopene, β-carotene, γ-carotene, ζ-carotene, δ-carotene, keto-γ-carotene, ψ-carotene, ε-carotene, β,ψ-carotene, torulene, echinenone, gamma-carotene, zeta-carotene, alpha-cryptoxanthin, diatoxanthin, 7,8-didehydroastaxanthin, fucoxanthin, fucoxanthinol, isorenieratene, β-isorenieratene lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, zeaxanthin, tetradehydrolycopene, and C30-carotenoids.

Methods for Optimizing the Carotenoid Biosynthetic Pathway

Metabolic engineering generally involves the introduction of new metabolic activities into the host organism or the improvement of existing processes by engineering changes such as adding, removing, or modifying genetic elements (Stephanopoulos, G., *Metab. Eng.*, 1: 1-11 (1999)). One such modification relies on genetically engineered modulations of the expression of relevant genes in a metabolic pathway. The effect of oleosin expression using the present methods was measured in microbial strains engineered to produce hydrophobic/lipophilic compounds (i.e. carotenoids). The modifications used to create these strains has been previous reported in copending applications U.S. Ser. Nos. 10/734778 and 10/735442, hereby incorporated by reference. Strong promoters are widely used for overexpression of key genes in a metabolic pathway (U.S. Ser. Nos. 10/734778 and 10/735442). Strong and moderately strong promoters that are useful for expression in *E. coli* include lac, trp, $IP_L$, $IP_R$, T7, tac, T5, and trc. A conventional way to regulate the amount and the timing of protein expression is to use an inducible promoter. An inducible promoter is not always active the way constitutive promoters are (e.g. viral promoters). Some inducible promoters are activated by physical means, such as the heat shock promoter. Other inducible promoters are activated by chemicals such as isopropyl-β-thiogalactopyranoside (IPTG) or Tetracycline (Tet).

Termination control regions may also be derived from various genes native to the preferred hosts. Optionally, a termination site may be unnecessary, however, it is most preferred if included.

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods of gene down-regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell or by the λ-Red recombination system used in the present invention. (See for example Hamilton et al., *J. Bacteriol.*, 171:4617-4622. (1989), Balbas et al., *Gene*, 136:211-213. (1993), Gueldener et al., *Nucleic Acids Res.*, 24:2519-2524 (1996), and Smith et al., *Methods Mol. Cell. Biol.*, 5:270-277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frame-shift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass.(hereinafter "Brock"), or Deshpande, Mukund V., *Appl. Biochem. Biotechnol.*, 36:227 (1992) (hereinafter "Deshpande").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element). Transposon-mediated random insertion in the chromosome can be used for isolating mutants for any number of applications including enhanced production of any number of desired products including enzymes or other proteins, amino acids, or small organic molecules including alcohols.

In the present invention it is preferred if the expressible DNA fragment is a promoter or some coding region useful for modulation of a biosynthetic pathway. Exemplified in the invention is the phage T5 strong promoter ($P_{T5}$) used for the modulation of the isoprenoid biosynthetic pathway in a recombination proficient E. coli host (U.S. Ser. Nos. 10/734778 and 10/735442).

Generally, the preferred length of the homology arms is about 10 to about 50 base pairs in length. Given the relatively short lengths of the homology arms used in the present invention for homologous recombination, one would expect that the level of acceptable mismatched sequences should be kept to an absolute minimum for efficient recombination, preferably using sequences which are identical to those targeted for homologous recombination. From 20 to 40 base pairs of homology, the efficiency of homologous recombination increases by four orders of magnitude (Yu et al., *PNAS.* 97:5978-5983. (2000)). Therefore, multiple mismatching within homology arms may decrease the efficiency of homologous.

The incorporation of multiple chromosomal modifications to the isoprenoid pathway genes makes use of a selectable marker on one of the two recombination elements (U.S. Ser. Nos. 10/734778 and 10/735442). The selectable marker is chosen from the group consisting of antibiotic resistance markers, enzymatic markers wherein the expressed marker catalyzes a chemical reaction creating a measurable difference in phenotypic appearance, and amino acid biosynthesis enzymes which enable a normally auxotrophic bacteria to grow without the exogenously supplied amino acid; the amino acid synthesized by the amino acid biosynthesis enzyme. As used herein the markers are flanked by site-specific recombinase recognition sequences. After selection and construct verification, a site-specific recombinase is used to remove the marker. The steps used to make the chromosomal modification can be repeated with additional in vivo chromosomal modifications. Selectable markers are known in the art and include, but are not limited to antibiotic resistance markers such as ampicillin, kanamycin, and tetracycline resistance. Selectable markers may also include amino acid biosynthesis enzymes (for selection of auxotrophs normally requiring the exogenously supplied amino acid of interest) and enzymes which catalyze visible changes in appearance such as β-galactosidase (catalyzes the conversion of Xgal into an easily discernable blue pigment) in lac bacteria.

The integration cassette is bounded by site-specific recombinases for the eventual removal of the selectable marker. Site-specific recombinases, such as the use of "flippase" (FLP) recombinase in the present invention, recognize specific recombination sequences (i.e. FRT sequences) and allow for the excision of the selectable marker. This aspect of the invention enables the repetitive use of the Applicant's process for multiple chromosomal modifications. The method is not limited to the FLP-FRT recombinase system as several examples of site specific recombinases and their associated specific recognition sequences are know in the art. Examples of other suitable site-specific recombinases and their corresponding recognition sequences include: Cre-lox, R/RS, Gin/gix, Xer/dif, Int/att, a pSR1 system, a cer system, and a fim system.

Measurement of the Hydrophobic/Lipophilic End Product

If the desired genetic end product is a colored product (e.g. many carotenoids) then transformants can be selected for on the basis of colored colonies, and the product can be quantitated by UV/vis spectrometry at the product's characteristic $\lambda_{max}$ peaks. Alternative analytical methods including, but not limited to HPLC, CE, GC and GC-MS can also be used.

In the present invention, β-carotene and canthaxanthin concentrations were measured by UV/vis spectrometry (using β-carotene's $\lambda_{max}$ peak of 450 and canthaxanthin $\lambda_{max}$ peak of 480 nm). The carotenoid was extracted by acetone from the cell pellet. The host strain included a reporter plasmid for the up regulation of genes involved in the synthesis of β-carotene or canthaxanthin. The reporter plasmid (pPCB15 or pDCQ108) carried the crtEXYIB gene cluster, facilitating the production of β-carotene. The reporter plasmid pDCQ307 carried the crtEWYIB gene cluster, facilitating the production of canthaxanthin.

For routine measurements, the amount of the carotenoid produced was measured by the ratio of the absorbance of the carotenoid of 1 mL of culture extracted by 1 mL of acetone (OD450 for β-carotene or OD480 for canthaxanthin) to the OD600 of the culture was used as an estimation of the relative carotenoid titers of the engineered strains.

The total carotenoid content of the cells (in grams) contained in 1 mL if culture is calculated by the formula: (Absorbance of carotenoid/Specific absorbance (M-1))×Volume of acetone (L)×Molecular weight (g/mol).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). In any case where program parameters were not prompted for, in these or any other programs, default values were used.

The meaning of abbreviations is as follows: "h" or "hr" means hour(s), "min" means minute(s), "sec" means second(s), "d" means day(s), "μL" mean microliters, "mL" means milliliters, "L" means liters.

Example 1

Cloning of Genes from *Pantoea stewartii*

Because of the relatedness between *P. stewartii* and *F. uredovora*, *P. stewartii* carotenoid synthesis genes can be amplified by PCR using primers based on the published sequence of the *E. uredovora* crt genes (GENBANK® Accession No. D90087, Misawa et al., *J. Bacteriol.*, V172: 6704 (1990)). This was demonstrated previously for the crtE, crtB and crtI genes (Scolinik and Bartley, *Plant Physiol.*, 108:1343 (1995)). Using the same approach, primers were designed using the sequence from *Erwinia uredovora* to amplify a fragment by PCR containing the crt genes. These sequences included 5'-3':

```
ATGACGGTCTGCGCAAAAAAACACG      SEQ ID NO:13

GAGAAATTATGTTGTGGATTTGGAATGC   SEQ ID NO:14
```

Chromosomal DNA was purified from *Pantoea stewartii* (ATCC No. 8199) and Pfu Turbo polymerase (Stratagene, La Jolla, Calif.) was used in a PCR amplification reaction under the following conditions: 94° C., 5 min; 94° C. (1 min)–60° C. (1 min)–72° C. (10 min) for 25 cycles, and 72° C. for 10 min. A single product of approximately 6.5 kb was observed following gel electrophoresis. Taq polymerase (Perkin Elmer) was used (10 min, 72° C. reaction) to add 3' adenosine nucleotides to the end of the PCR fragment which was then ligated into pCR4-TOPO vector (Invitrogen, Carlsbad, Calif.) to produce pPCB13. *E. coli* DH5α (Life Technologies, Rockville, Md.) was transformed by electroporation with the ligation mixture and bright yellow colonies were isolated. Their color indicated the production of a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. Nos. 5,366,860; EP 272007) using transposon specific primers. Sequence assembly was performed with the Sequencher program (Gene Codes Corp., Ann Arbor, Mich.).

Example 2

Construction of *E. coli* Strains with the Phage T5 Strong Promoter Chromosomally Integrated Upstream of Isoprenoid Genes The native promoters of the *E. coli* isoprenoid genes, dxs, idi, and ispDispF were replaced with the phage T5 ($P_{T5}$) strong promoter (SEQ ID NO: 15) using the "two PCR-fragments" chromosomal integration method as shown in FIG. 2. The two PCR-fragment method used in the present application has been previously described (U.S. Ser. Nos. 10/734778, 10/734936, and 10/735442; hereby incorporated by reference). The method for replacement is based on homologous recombination via the λ Red recombinase encoded on a helper plasmid. Recombination occurs between the *E. coli* chromosome and two PCR fragments that contain 20-50 bp homology patches at both ends of PCR fragments (FIG. 2). For integration of the T5 strong promoter upstream of these genes, a two-PCR-fragment method was employed. In this method, the two fragments were comprised of a linear DNA fragment (1489 bp) containing a kanamycin selectable marker flanked by site-specific recombinase target sequences (FRT) and a linear DNA fragment (154 bp) containing a phage T5 promoter ($P_{T5}$; SEQ ID NO:15) comprising the –10 and –35 consensus promoter sequences, lac operator (lacO), and a ribosomal binding site (RBS).

By using the two PCR fragment method, the kanamycin selectable marker and phage T5 promoter (kan-$P_{T5}$) were cointegrated upstream of the dxs, idi, and ispDF genes, yielding kan-$P_{T5}$-dxs, kan-$P_{T5}$-idi, and kan-$P_{T5}$-ispDF. The linear DNA fragment (1489 bp) which contained a kanamycin selectable marker, flanked by site-specific recombination sequences, was synthesized by PCR from plasmid pKD4 (Datsenko and Wanner, *PNAS.*, 97:6640-6645 (2000)) with primer pairs as follows in Table 3.

TABLE 3

Primers for Amplification of the Kanamycin Selectable Marker

| Primer Name | Primer Sequence | SEQ ID NO: |
|---|---|---|
| 5'-kan(dxs) | TGGAAGCGCTAGCGGACTACATCATCCAGCGTAA TAAATAACGTCTTGAGCGATTGTGTAG[1] | 16 |
| 5'-kan(idi) | TCTGATGCGCAAGCTGAAGAAAAATGAGCATGGA GAATAATATGACGTCTTGAGCGATTGTGTAG[1] | 17 |
| 5'-kan(ispDF) | GACGCGTCGAAGCGCGCACAGTCTGCGGGCAAA ACAATCGATAACGTCTTGAGCGATTGTGTAG[1] | 18 |
| 3'-kan | GAAGACGAAAGGGCCTCGTGATACGCCTATTTTT ATAGGTTATATGAATATCCTCCTTAGTTCC[2] | 19 |

[1]The underlined sequences illustrate each respective homology arm chosen to match sequences in the upstream region of the chromosomal integration site, while the remainder is the priming sequence)
[2]The underlined sequences illustrate homology arm chosen to match sequences in the 5'-end region of the T5 promoter DNA fragment The second linear DNA fragment (154 bp) containing a phage T5 promoter was synthesized by PCR from pQE30 (QIAGEN, Inc., Valencia, Calif.) with primer pairs as follows in Table 4.

TABLE 4

Primers for Amplification of the T5 Promoter

| Primer Name | Primer Sequence | SEQ ID NO: |
|---|---|---|
| 5'-T5 | CTAAGGAGGATATTCATATAACCTATAAAAATAG GCGTATCACGAGGCCC[1] | 20 |
| 3'-T5(dxs) | GGAGTCGACCAGTGCCAGGGTCGGGTATTTGGCA ATATCAAAACTCATAGTTAATTTCTCCTCTTTAA TG[2] | 21 |
| 3'-T5(idi) | TGGGAACTCCCTGTGCATTCAATAAAATGACGTG TTCCGTTTGCATAGTTAATTTCTCCTCTTTAAT G[2] | 22 |
| 3'-T5(ispDF) | CGGCCGCCGGAACCACGGCGCAAACATCCAAATG AGTGGTTGCCATAGTTAATTTCTCCTCTTTAAT G[2] | 23 |

[1]The underlined sequences illustrate homology arm chosen to match sequences in the 3'-end region of the kanamycin DNA fragment
[2]The underlined sequences illustrate each respective homology arm chosen to match sequences in the downstream region of the chromosomal integration site Standard PCR conditions were used to amplify the linear DNA fragments with AmpliTaq Gold® polymerase (Applied Biosystems, Foster City, Calif.) as follows:

| PCR reaction: | PCR reaction mixture: |
|---|---|
| Step 1 94° C. 3 min | 0.5 µL plasmid DNA |
| Step 2 93° C. 30 sec | 5 µL 10X PCR buffer |
| Step 3 55° C. 1 min | 1 µL dNTP mixture (10 mM) |
| Step 4 72° C. 3 min | 1 µL 5'-primer (20 µM) |
| Step 5 Go To Step2, 30 cycles | 1 µl 3'-primer (20 µM) |
| Step 6 72° C. 5 min | 0.5 µL AmpliTaq Gold ® polymerase |
| | 41 µL sterilized dH$_2$O |

After completing the PCR reactions, 50 µL of each PCR reaction mixture was run on a 1% agarose gel and the PCR products were purified using the QIAquick Gel Extraction Kit™ as per the manufacturer's instructions (Cat. # 28704, QIAGEN). The PCR products were eluted with 10 µL of distilled water. The DNA Clean & Concentrator™ kit (Zymo Research, Orange, Calif.) was used to further purify the PCR product fragments as per the manufacturer's instructions. The PCR products were eluted with 6-8 µL of distilled water to a concentration of 0.5-1.0 µg/µL.

The *E. coli* MC1061 strain, carrying a λ Red recombinase expression plasmid pKD46 (amp$^R$) (Datsenko and Wanner, supra; SEQ ID NO: 24), was used as a host strain for the chromosomal integration of the PCR fragments. The strain was constructed by transformation of *E. coli* strain MC1061 with the λ Red recombinase expression plasmid, pKD46 (amp$^R$). The λ-Red recombinase in pKD46 is comprised of three genes exo, bet, and gam expressed under the control of an arabinose-inducible promoter. Transformants were selected on 100 µg/mL of ampicillin LB plates at 30° C.

For transformation, electroporation was performed using 5-10 µg of the purified PCR products carrying the kanamycin marker and phage T5 promoter. Approximately one-half of the cells transformed were spread on LB plates containing 25 µg/mL of kanamycin in order to select antibiotic-resistant transformants. After incubating the plate at 37° C. overnight, antibiotic-resistance transformants were selected as follows: 10 colonies of kan-$P_{T5}$-dxs, 12 colonies of kan-$P_{T5}$-idi, and 10 colonies of kan-$P_{T5}$-ispDF.

PCR analysis was used to confirm the integration of both the kanamycin selectable marker and the phage T5 promoter ($P_{T5}$)(SEQ ID NO:15) in the correct location on the *E. coli* chromosome. For PCR, a colony was resuspended in 50 µL of PCR reaction mixture containing 200 µM dNTPs, 2.5 U AmpliTaq™ (Applied Biosytems), and 0.4 µM of specific primer pairs. Test primers were chosen to match sequences of the regions located in the kanamycin (5'-primer) and the early coding-region of each isoprenoid gene (3'-primer). The PCR reaction was performed as described in above. The resultant *E. coli* strains carrying each kan-$P_{T5}$-isoprenoid gene fusion on the chromosome were used for stacking Example 3

Construction of *E. coli* $P_{T5}$-dxs $P_{T5}$-idi $P_{T5}$-ispDF Strain

*E. coli* $P_{T5}$-dxs $P_{T5}$-idi $P_{T5}$-ispDF, was constructed as follows.

First, P1 lysate of the *E. coli* kan-$P_{T5}$-dxs strain was prepared by infecting a growing culture of bacteria with the P1 phage and allowing the cells to lyse. For P1 infection, *E. coli* kan-$P_{T5}$-dxs strain was inoculated in 4 mL LB medium with 25 µg/mL kanamycin, grown at 37° C. overnight, and then sub-cultured with 1:100 dilution of an overnight culture in 10 mL LB medium containing 5 mM CaCl$_2$. After 20-30 min of growth at 37° C., 10$^7$ P1$_{vir}$ phages were added. The cell-phage mixture was aerated for 2-3 h at 37° C. until lysed, several drops of chloroform were added and the mixture vortexed for 30 sec and incubated for an additional 30 min at room temp. The mixture was then centrifuged for 10 min at 4500 rpm, and the supernatant transferred into a new tube to which several drops of chloroform were added.

Second, P1 lysate made on *E. coli* kan-$P_{T5}$-dxs strain was transduced into the recipient strain, *E. coli* MG1655 containing a β-carotene biosynthesis expression plasmid pPCB 15 (cam$^R$). Plasmid pPCB15 (cam$^R$) (SEQ ID NO: 25) encodes the carotenoid biosynthesis gene cluster (crtEXYIB) from *Pantoea Stewartii* (ATCC 8199). Plasmid pPCB15 was constructed from ligation of SmaI digested pSU18 (Bartolome, B. et al., *Gene*, 102:75-78 (1991)) vector with a blunt-ended PmeI/NotI fragment carrying crtEXYIB from pPCB13. The *E. coli* MG1655 pPCB15 recipient cells were grown to mid-log phase (1-2×10$^8$ cells/mL) in 4 mL LB medium with 25 µg/mL chloramphenicol at 37° C. Cells were spun down for 10 min at 4500 rpm and resuspended in 2 mL of 10 mM MgSO$_4$ and 5 mM CaCl$_2$. Recipient cells (100 µL) were mixed with 1 µL, 10 µL, or 100 µL of P1 lysate stock (10$^7$ pfu/µL) made from the *E. coli* kan-$P_{T5}$-dXS strain and incubated at 30° C. for 30 min. The recipient cell-lysate mixture was spun down at 6500 rpm for 30 sec, resuspended in 100 µL of LB medium with 10 mM of sodium citrate, and incubated at 37° C. for 1 h. Cells were plated on LB plates containing both 25 µg/mL kanamycin and 25 µg/mL chloramphenicol in order to select for antibiotic-resistant transductants, and incubated at 37° C. for 1 or 2 days. Sixteen kanamycin-resistance transductants were selected.

To eliminate kanamycin selectable marker from the chromosome, a FLP recombinase expression plasmid pCP20 (amp$^R$) (ATCC PTA-4455) (Cherepanov and Wackernagel, Gene, 158:9-14 (1995)), which has a temperature-sensitive replication of origin, was transiently transformed into one of the kanamycin-resistant transductants by electroporation (see U.S. Ser. Nos. 10/734778 and 10/735442). Cells were spread onto LB agar containing 100 μg/mL ampicillin and 25 μg/mL chloramphenicol LB plates, and grown at 30° C. for 1 day. Colonies were picked and streaked on 25 μg/mL chloramphenicol LB plates without ampicillin antibiotics and incubated at 43° C. overnight. Plasmid pCP20 has a temperature sensitive origin of replication and was cured from the host cells by culturing cells at 43° C. The colonies were tested for ampicillin and kanamycin sensitivity to test loss of pCP20 and kanamycin selectable marker by streaking colonies on 100 μg/mL ampicillin LB plate or 25 μg/mL kanamycin LB plate. In this manner, the E. coli $P_{T5}$-dxs strain was constructed.

In order to stack kan-$P_{T5}$-idi on the chromosome of E. coli $P_{T5}$-dxs, P1 lysate made on E. coli kan-$P_{T5}$-idi strain was transduced into the recipient strain, E. coli $P_{T5}$-dxs, as described above in copending applications number (U.S. Ser. Nos. 10/734778; hereby incorporated by reference). Approximately 450 kanamycin-resistance transductants were selected. After transduction, the kanamycin selectable marker was eliminated from the chromosome as described above, yielding E. coli $P_{T5}$-dxs $P_{T5}$-idi strain.

$P_{T5}$-ispDF gene cluster was further stacked into the E. coli $P_{T5}$-dxs $P_{T5}$-idi strain by P1 transduction in combination with the FLP recombination system (U.S. Ser. No. 10/734778). P1 lysate was with E. coli kan-$P_{T5}$-ispDF strain was transduced into the recipient strain, E. coli kan-$P_{T5}$-dxs kan-$P_{T5}$-idi containing a β-carotene biosynthesis expression plasmid pPCB15 (cam$^R$), as described above. Twenty-one kanamycin-resistance transductants were selected. The kanamycin selectable marker was eliminated from the chromosome of the transductants using a FLP recombinase expression system, yielding E. coli $P_{T5}$-dxs $P_{T5}$-idi $P_{T5}$-ispDF strain.

For the E. coli $P_{T5}$-dxs $P_{T5}$-idi $P_{T5}$-ispDF strain, the correct integration of the phage T5 promoter upstream of dxs, idi and ispDF genes on the E. coli chromosome, and elimination of the kanamycin selectable marker, were confirmed by PCR analysis. A colony of the E. coli $P_{T5}$-dxs $P_{T5}$-idi $P_{T5}$-ispDF strain was tested by PCR with different combination of specific primer pairs, T-kan (5'-ACCGGATATCACCACTTATCTGCTC-3'; SEQ ID NO: 26) and B-dxs (5'-TGGCMCA GTCGTAGCTCCTGGGTGG-3'; SEQ ID NO: 27), T-T5 (5'-TAACCTATAAAAATAGGCG-TATCACGAGGCCC-3'; SEQ ID NO: 28) and B-dxs, T-kan and B-idi (5'-TCATGCTGACCTGGTGMGGAATCC-'3; SEQ ID NO: 29), T-T5 and B-idi, T-kan and B-ispDF (5'-CCAGCAGCGCATGCACCGAGTGTTC-3'; SEQ ID NO: 30), T-T5 and B-ispDF. Test primers were chosen to amplify regions located either in the kanamycin or the phage T5 promoter and the downstream region of the chromosomal integration site. The PCR reaction was performed as described in Example 1. The PCR results indicated the elimination of the kanamycin selectable marker from the E. coli chromosome. The chromosomal integration of the phage T5 promoter fragment upstream of the dxs, idi, and ispDF genes was confirmed based on the expected sizes; of PCR products, 229 bp, 274 bp, and 296 bp, respectively.

Example 4

Transformation of pDCQ108 into E. coli $P_{T5}$-dxs $P_{T5}$-idi $P_{T5}$-ispDF Strain The low copy number plasmid pPCB15 (SEQ ID NO: 25) containing β-carotene synthesis genes Pantoea crtEXYIB, used as a reporter plasmid for monitoring β-carotene production in E. coli $P_{T5}$-dxs $P_{T5}$-idi $P_{T5}$-ispDF was replaced with the medium copy number plasmid pDCQ108 (ATCC PTA-4823) containing β-carotene synthesis genes Pantoea crtEXYIB. The plasmid pPCB15 was eliminated form the E. coli $P_{T5}$-dxs $P_{T5}$-idi $P_{T5}$-ispDF strain by streaking on LB plate, incubating at 37° C. for 2 days, and picking up a white-colored colony.

The plasmid pDCQ108 (tet$^R$) (ATCC PTA-4823) was transformed into E. coli $P_{T5}$-dxs $P_{T5}$-idi $P_{T5}$-ispDF strain that contains no plasmid. Electroporation was performed by using a Bio-Rad Gene Pulser set at 1.8 kV, 25 μF with the pulse controller set at 200 ohms. SOC medium (1 mL) was added after electroporation. The cells were incubated at 37° C. for 1 hr, and were spread on LB plates containing both 25 μg/ml tetracycline LB plates at 37° C. Transformants were selected on 25 μg/mL of tetracycline LB plates after growing at 37° C. overnight. The resultant transformants were the E. coli $P_{T5}$-dxs $P_{T5}$-idi $P_{T5}$-ispDF strain carrying pDCQ108. This strain is identified as strain WS185.

Example 5

Synthesis of A Gene Encodinq a β-carotene Ketolase

Agrobacterium aurantiacum is a marine bacterium that naturally produces astaxanthin. The carotenoid biosynthesis gene cluster in A. aurantiacum contains the β-carotene ketolase gene crtW and the β-carotene hydroxylase gene crtZ (Misawa et al., J. Bacteriol., 177:6575-6584 (1995). The sequence of the wild type crtW gene from Agrobacterium aurantiacum is SEQ ID NO: 31 (U.S. Pat. No. 5,972, 690; GENBANK® D58420). A synthetic gene (SEQ ID NO: 32) with a different codon usage (codon optimized for expression in Methylomonas sp. 16a; ATCC PTA-2402; U.S. Ser. No. 10/997,844; hereby incorporated by reference) but encoding for the same protein was constructed by Aptagen Inc. (Hemdon, Va.) and cloned onto the pCRScript vector to form pCRScript-Dup 1. The ribosomal binding site (RBS) was engineered upstream of the start codon as the RBS sequence from pTrcHis2-TOPO vector (Invitrogen, Carlsbad, Calif.). Several restriction sites were also engineered at the 5' and 3' ends of the genes to facilitate cloning. None of the modifications in the codon-optimized gene changed the amino acid sequence of the encoded ketolase protein (SEQ ID NO: 33).

Example 6

Construction of Canthaxanthin Expression Plasmid pDCQ307

The purpose of this Example was to prepare a canthaxanthin expression plasmid, referred to herein as pDCQ307. This canthaxanthin-producing plasmid was prepared by coupling the codon-optimized crtW gene (SEQ ID NO: 32) described in Example 5, to a β-carotene synthesis gene cluster. The crtW gene was cloned downstream of crtE in the reorganized crtEYIB cluster from P. stewartii ATCC8199 to form the operon crtEWYIB.

*Pantoea stewartii* ATCC #8199 (WO 03/016503) contains the natural gene cluster crtEXYIBZ. The genes required for β-carotene synthesis (i.e., crtE and crtYIB) were joined together by PCR. Specifically, the crtE gene (SEQ ID NO: 1) and crtYIB genes (SEQ ID NO:34) were each amplified using chromosomal DNA as template and the primers given in Table 5.

TABLE 5

Primers Used for Creation of the crtEYIB Reporter Construct

| Gene(s) | Forward Primer* | Reverse Primer |
|---|---|---|
| crtE | pBHRcrt_1F:<br>5'-<u>GAATTC</u>GCCCTTGACGGT<br>CT-3'<br>(SEQ ID NO:35) | pBHRcrt_1R:<br>5'-CGGTTGCATAATCCTGCC<br>CACT<u>CAATTG</u>TTAACTGACGG<br>CAGCGAGTTTT-3'<br>(SEQ ID NO:36) |
| crtYIB | pBHRcrt_2F:<br>5'-AAAACTCGCTGCCGTCAG<br>TTAA<u>CAATTG</u>AGTGGGCAGGA<br>TTATGCAACCG-3'<br>(SEQ ID NO:37) | pBHRcrt_2R:<br>5'-GGTACCTAGATCGGGCGC<br>TGCCAGA-3'<br>(SEQ ID NO:38) |

*Note:
Underlined portions within each primer correspond to restriction sites for EcoRI, MfeI.

The PCR reactions were performed with Pfu DNA polymerase in buffer supplied by the manufacturer containing dNTPs (200 µM of each). Parameters for the thermocycling reactions were: 92° C. (5 min), followed by 30 cycles of: 95° C. (30 sec), 55° C. (30 sec), and 72° C. (5 min). The reaction concluded with 1 cycle at 72° C. for 10 min. The two PCR products were gel purified and joined together by a subsequent PCR reaction using the primers pBHRcrt_1F (SEQ ID NO:35) and pBHRcrt_2R (SEQ ID NO:38). Parameters for the thermocycling reaction were: 95° C. (5 min), followed by 20 cycles of: 95° C. (30 sec), 55° C. (1 min) and 72° C. (8 min). A final elongation step at 72° C. for 10 min completed the reaction. The final 4511 bp PCR product was cloned into the pTrcHis2-Topo vector (Invitrogen, Carlsbad, Calif.) in the forward orientation, resulting in plasmid pDCQ300. The ~4.5 kB EcoRI fragment of pDCQ300 containing the crtEYIB gene cluster was ligated into the unique EcoRI site of vector pBHR1 (MoBiTec GmbH, Goettingen, Germany), to create construct pDCQ301. In pDCQ301, a unique MfeI site was engineered in the intergenic region of crtE and crtY.

The ~0.8 kB EcoRI fragment of pCRScript-Dup1, prepared as described in Example 5, containing the synthetic codon-optimized crtW gene was ligated to the unique MfeI site in pDCQ301. In the resulting construct pDCQ307, the crtEWYIB genes were under the control of the chloramphenicol resistant gene promoter of the vector.

Example 7

Transformation of pDCQ307 into *E. coli* $P_{T5}$-dxs $P_{T5}$-idi $P_{T5}$-ispDF Strain The plasmid pDCQ307 (Kan$^R$) was transformed into *E. coli* $P_{T5}$-dxs $P_{T5}$-idi $P_{T5}$-ispDF strain that contains no plasmid. Electro-transformation was performed as described in Example 4. Transformants were selected on 25 µg/mL of kanamycin LB plates at 37° C. The resultant transformants were the *E. coli* $P_{T5}$-dxs $P_{T5}$-idi $P_{T5}$-ispDF strain carrying pDCQ307. This strain is identified as strain WS384.

Example 8

Measurement of Carotenoid Production in *E. coli* $P_{T5}$-dxs $P_{T5}$-idi $P_{T5}$-ispDF Strain The production of carotenoids in the chromosomally engineered β-carotene producing *E. coli* strain WS185 (pDCQ108, $P_{T5}$-dxs $P_{T5}$-idi $P_{T5}$-ispDF) and the canthaxanthin producing *E. coli* strain WS384 (pDCQ307, $P_{T5}$-dxs $P_{T5}$-idi $P_{T5}$-ispDF) was quantified following spectrophotometrically. The quantitative analysis of β-carotene production was achieved by measuring the spectra of β-carotene's characteristic $\lambda_{max}$ peak of greatest absorption at 450 nm and that of canthaxathin at 480 nm. Cells from 1-mL of culture were harvested by centrifugation (3 min at 16,000 g) and the supernatant removed completely. Carotenoid pigment was extracted by 1 mL of acetone. The cell suspension was agitated by vortexing for 1 min and then rocking for 1 hour at room temperature. Cell debris were removed by centrifugation for 5 min at 16,000×g and the absorption of the acetone layer containing the carotenoid was measured at the appropriate wavelength (β-carotene at 450 nm, canthaxanthin at 480 nm) using an Ultrospec 3000 spectrophotometer (Amersham Biosciences, Piscataway, N.J.). The amounts of carotenoids were derived from the specific absorbance of each carotenoid (138,900 M$^{-1}$ for β-carotene at 450 nm, MW=537) and 132,740 M$^{-1}$ at 480 for canthaxanthin (MW=565) (in *Carotenoids*, Vol 1B Spectroscopy, Britton et al. Editors, Birkhäuser publisher, 13-62, (1995)).

Cell mass was obtained by measuring the dry cell weight of cells filtered and dried overnight at 130° C. from 25 mL of cultures grown for 12 or 24 hr and expressing various levels of carotenoids. The correlation of ~0.31+/−0.2 mg dry cell weight for 1 mL of culture with an optical density of 1 OD$_{600}$ was determined.

For routine analysis, the ratio of the absorbance of the carotenoid of 1 mL of culture extracted by 1 mL of acetone (OD450 for β-carotene or OD480 for canthaxanthin) to the OD600 of the culture was used as an estimation of the relative carotenoid titers of the engineered strains.

The total carotenoid content of the cells (in grams) contained in 1 mL is calculated by the formula:

(Absorbance of carotenoid/Specific absorbance (M$^{-1}$))×Volume of acetone (L)×Molecular weight (g mol$^{-1}$).

A value of OD450 of 0.1 corresponds to 0.39 µg of β-carotene and a value of OD480 of 0.1 corresponds to 0.42 µg of canthaxanthin. Similarly, a ratio OD450/OD600 of 0.1 correspond to approximately 1,260 µg of β-carotene/g of dry cell weight and a ratio of OD480/OD600 of 0.1 correspond to approximately 1,260 µg of canthaxanthin/g of dry cell weight.

Example 9

Identification of New Oleosin Genes and Peptide Sequences

Oleosin genes were identified in a database of proprietary plant cDNA sequences on the basis of sequence similarity. The amino acid sequence of the *Theobroma cacao* oleosin GENBANK® accession number AAM46777) as well as of the *Perilla frutescens* oleosin (GENBANK® accession number AAG24455) were compared to the sequences of plant cDNA clones translated in the six frames using the TBlastN algorithm (Altschul, S. et al., *Nucleic Acids Res.*, 25:3389-3402 (1997)).

Fifteen full-length clones encoding distinct oleosins and oleosins not already identified in public databases (GEN-BANK®) were chosen and are described in Table 6.

TABLE 6

Name and source of clones encoding new oleosin genes

| Database clone name | Source | Clone name | Nucleotide SEQ ID NO. | Amino Acid SEQ ID NO. |
|---|---|---|---|---|
| lds3c.pk011.e15 | Guar | OL3 | 39 | 40 |
| ceb7f.pk004.b6a | Corn | OL4 | 41 | 42 |
| ece1c.pk006.p7 | Castorbean | OL5 | 43 | 44 |
| ece1c.pk003.i24 | Castorbean | OL6 | 45 | 46 |
| vmb1na.pk002.f2 | Grape | OL7 | 47 | 48 |
| eas1c.pk003.l3 | Amaranth | OL8 | 49 | 50 |
| ncs.pk0006.a2 | *Catalpa* | OL9 | 51 | 52 |
| vs1.pk0015.b7 | *Vernonia* | OL11 | 53 | 54 |
| egh1c.pk003.h3 | Cotton | OL16 | 55 | 56 |
| ecs1c.pk007.g10 | Marigold | OL17 | 57 | 58 |
| fds1n.pk018.c6 | *Momordica* | OL18 | 59 | 60 |
| pps.pk0001.f6 | *Pricamnia* | OL19 | 61 | 62 |
| sdp2c.pk001.o14 | Soy | OL20 | 63 | 64 |
| hls1c.pk009.c7 | Sunflower | OL23 | 65 | 66 |
| fds1n.pk018.l23 | Pear | OL24 | 67 | 68 |

All comparisons were done using either the BLASTNnr or BLASTXnr algorithm. The results of the BLAST comparisons are given in Table 7 which summarize the sequence to which each sequence has the most similarity. Table 7 displays data based on the BLASTX nr algorithm with values reported in expect values. The "expect value" estimates the statistical significance of the match, specifying the number of matches, with a given score, that are expected in a search of a database of this size absolutely by chance.

TABLE 7

BLAST Analysis to Publicly Available Sequences

| Clone Name — Short name | Organism of Isolation | Polypeptide Length (amino acids) | GENBANK® Entry to Highest Similarity Identified | SEQ ID Base | SEQ ID Peptide | % Identity[a] | % Similarity[b] | E-value[c] |
|---|---|---|---|---|---|---|---|---|
| lds3c.pk011.e15 — OL3 | Guar (*Cyamposis*) | 163 | AAM46778.1 15.8 kDa oleosin [*Theobroma cacao*] | 39 | 40 | 68 | 79 | 2e-44 |
| ceb7f.pk004.b6a — OL4 | Corn (*Zea*) | 186 | A35040 18 kDa Oleosin Zm-II [*Zea mays*] | 41 | 42 | 92 | 92 | 4e-85 |
| ece1c.pk006.p7 — OL5 | Castorbean (*Ricinus*) | 148 | AAM46778.1 15.8 kDa oleosin [*Theobroma cacao*] | 43 | 44 | 60 | 75 | 8e-46 |
| ece1c.pk003.i24 — OL6 | Castorbean (*Ricinus*) | 153 | AM46777.1 16.9 kDa oleosin [*Theobroma cacao*] | 45 | 46 | 55 | 73 | 2e-42 |
| vmb1na.pk002.f2 — OL7 | Grape (*Vitis*) | 133 | CAA88360.1 Oleosin-like protein [*Citrus sinensis*] | 47 | 48 | 62 | 75 | 1e-35 |
| eas1c.pk003.l3 — OL8 | Amaranth (*Amaranthus*) | 140 | CAA88360.1 Oleosin-like protein [*Citrus sinensis*] | 49 | 50 | 70 | 85 | 3e-45 |
| ncs.pk0006.a2 — OL9 | Catalpa (*Catalpa*) | 141 | AAB58402.1 15.5 kDa oleosin [*Sesamum indicum*] | 51 | 52 | 78 | 89 | 5e-50 |
| vs1.pk0015.b7 — OL11 | Vernonia (*Vernonia*) | 202 | CAA44224.1 Oleosin [*Helianthus annuus*] | 53 | 54 | 66 | 79 | 1e-51 |
| egh1c.pk003.h3 — OL16 | Cotton (*Gossypium*) | 154 | AAA18523.1 16.4 kDa Oleosin [*Gossypium hirsutum*] | 55 | 56 | 98 | 98 | 2e-79 |
| ecs1c.pk007.g10 — OL17 | Marigold (*Tagates*) | 216 | CAA44224.1 Oleosin [*Helianthus annuus*] | 57 | 58 | 78 | 90 | 7e-44 |
| fds1n.pk018.c6 — OL18 | Momordica (*Momordica*) | 185 | AAM46777.1 16.9 kDa oleosin [*Theobroma cacao*] | 59 | 60 | 55 | 71 | 3e-45 |
| pps.pk0001.f6 — OL19 | Pricamnia (*Pricamnia*) | 135 | AAB24078.1 Llipid body membrane protein [*Daucus carota*] | 61 | 62 | 61 | 76 | 4e-35 |
| sdp2c.pk001.o14 — OL20 | Soy (*Glycine*) | 166 | AAM46778.1 15.8 kDa oleosin [*Theobroma cacao*] | 63 | 64 | 66 | 77 | 3e-44 |
| hls1c.pk009.c — OL23 | Sunflower (*Helianthus*) | 176 | S51940 Oleosin [*Prunus amygdalus*] | 65 | 66 | 67 | 77 | 2e-43 |

TABLE 7-continued

BLAST Analysis to Publicly Available Sequences

| Clone Name — Short name | Organism of Isolation | Polypeptide Length (amino acids) | GENBANK® Entry to Highest Similarity Identified | SEQ ID Base | SEQ ID Peptide | % Identity[a] | % Similarity[b] | E-value[c] |
|---|---|---|---|---|---|---|---|---|
| fds1n.pk018.l23 — OL24 | Pear (*Pyrus*) | 156 | AAM46777.1 16.9 kDa oleosin [*Theobroma cacao*] | 67 | 68 | 61 | 76 | 7e–49 |

[a]Identity is defined as percentage of amino acids that are identical between the two proteins.
[b]Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 10

Sequence Analysis of the Oleosin Family

The amino acid sequences of several publicly available oleosins from a variety of sources were retrieved from the GENBANk® database (Table 8).

Table 8. Publicly Available Oleosin Sequences

TABLE 8

Publicly Available Oleosin Sequences

| Source | Length (amino acids) | GENBANK® Accession number |
|---|---|---|
| *Zea mays* (corn) | 187 (SEQ ID NO: 69) | P21641 |
| *Hordeum vulgare* (barley) | 184 | S57778 |
| *Daucus carota* (carrot) | 180 | JQ0986 |
| *Perilla frutescens* (perilla) | 177 | AAG24455 |
| *Olea europeae* subsp. *Europaea* (olive) | 165 | AAL92479 |
| *Theobroma cacao* (cacao) | 160 | AAM46777 |
| *Arachis hypogaea* (peanut) | 176 | AAK13450 |
| *Arabidopsis thaliana* (thale cress) | 199 | NP198858 |
| *Glycine max* (soybean) | 224 | AAA17855 |
| *Helianthus annus* (sunflower) | 184 | S60482 |
| *Prunus dulcis* (almond) | 149 | S51940 |
| *Corylus avellana* (Hazel nut) | 140 | AAO65960 |
| *Sesamum indicum* (sesame) | 145 | AAD42942 |
| *Brassica napus* (rape) | 159 | P29110 |

An alignment of these sequences was produced with the ClustalW sequence alignment software as shown on FIG. 3. Within this set of oleosin sequences, thirteen amino acid positions are conserved as shown in Table 9.

Table 9. Signature amino acid conseved in 13 representative publicly available oleosin sequences.

TABLE 9

Signature amino acid conserved in 13 representative publicly available oleosin sequences.

| Conserved Amino Acid | Position in Corn Oleosin Sequence GENBANK® P21641 |
|---|---|
| G | 60 |
| L | 62 |
| L | 70 |
| L | 77 |
| P | 82 |
| F | 87 |
| S | 88 |
| P | 89 |
| P | 93 |
| A | 94 |
| L | 106 |
| G | 109 |
| G | 112 |

In one embodiment, an oleosin is defined as any protein, natural or synthetic, that includes a 60 to 80 amino acid-long fragment that can be aligned with the sequence segment of the Corn Oleosin Zm-II (GENBANK® accession number P21641; SEQ ID NO: 69) segment extending from position 50 to 120, having more than 25% amino acid identity over that segment and sharing 8 or more of the 13 conserved amino acids listed in Table 9.

Sequence Analysis of Present Oleosins

The amino acid sequences of the new oleosins listed in Example 9 were included in the alignment of previously described oleosins. Six of the 13 amino acid positions identified in a set of representative oleosin publicly available are conserved among the 15 new oleosins introduced in Example 9 as shown in Table 10.

TABLE 10

Conservation of signature amino acids

| Clone name | "Shared" conserved positions |
|---|---|
| OL3 | 13/13 |
| OL4 | 13/13 |
| OL5 | 8/13 |
| OL6 | 9/13 |
| OL7 | 11/13 |
| OL8 | 13/13 |
| OL9 | 13/13 |

TABLE 10-continued

Conservation of signature amino acids

| Clone name | "Shared" conserved positions |
|---|---|
| OL11 | 13/13 |
| OL16 | 13/13 |
| OL17 | 12/13 |
| OL18 | 13/13 |
| OL19 | 13/13 |
| OL20 | 13/13 |
| OL23 | 13/13 |
| OL24 | 13/13 |

Among the new oleosins, a minimum of 8 out of 13 signature amino acids defining the oleosin family are conserved. This percentage defines the oleosin family as explained above.

Alternatively, the oleosin family can be defined by its homology to a consensus amino acid sequence (i.e. the "diagnostic motif") found in the hydrophobic core of all oleosins. This motif is based on the "proline knot" region (Napier et al., supra), a region of about 12 to about 16 highly conserved amino acids. Based on this conserved region, an amino acid sequence (14 amino acids in length) useful for identifying additional oleosin (the "diagnostic motif") is provided as follow:

```
TPLFVIFSPVLVPA.        (SEQ ID NO:70)
```

Comparison of the diagnostic motif to the present oleosins as well as several publicly available oleosin sequences is provided in Table 11.

TABLE 11

Percent Identity and Similarity of Various Oleosins to the Oleosin Diagnostic Motif

| Oleosin and/or Source (SEQ ID NO) or GENBANK ® Accession No. | % Identity[a] to the diagnostic motif SEQ ID NO: 70 | % Similarity[b] to the diagnostic motif SEQ ID NO: 70 |
|---|---|---|
| OL3 Guar (SEQ ID NO: 40) | 78 | 92 |
| OL4 Zea mays (SEQ ID NO: 42) | 85 | 99 |
| OL5 Castor bean (SEQ ID NO: 44) | 57 | 78 |
| OL6 Castor bean (SEQ ID NO: 46) | 57 | 92 |
| OL7 Vitis sp. (SEQ ID NO: 48) | 92 | 92 |
| OL8 Amaranth (SEQ ID NO: 50) | 92 | 92 |
| OL9 Catalpa (SEQ ID NO: 52) | 83 | 91 |
| OL11 Vernonia (SEQ ID NO: 54) | 92 | 99 |
| OL16 Cotton (SEQ ID NO: 56) | 100 | 100 |
| OL17 Marigold (SEQ ID NO: 58) | 85 | 99 |
| OL18 Momordica (SEQ ID NO: 60) | 71 | 99 |
| OL19 Pricamnia (SEQ ID NO: 62) | 78 | 99 |
| OL20 Glycine max (SEQ ID NO: 64) | 85 | 92 |
| OL23 Helianthus annus (SEQ ID NO: 66) | 85 | 92 |
| OL24 Pear (SEQ ID NO: 68) | 78 | 99 |
| Zea mays P21641 | 85 | 99 |
| Hordeum vulgare S57778 | 78 | 99 |
| Daucus carota JQ0986 | 85 | 99 |
| Perilla frutescens AAG24455 | 100 | 100 |
| Olea europaea subsp. europaea AAL92479 | 92 | 99 |
| Theobroma cacao AAM46777 | 92 | 99 |
| Arachis hypogaea AAK13450 | 71 | 85 |
| Arabidopsis thaliana NP198858 | 76 | 99 |
| Glycine max AAA17855 | 85 | 99 |
| Helianthus annus S60482 | 92 | 99 |
| Prunus dulcis S51940 | 92 | 92 |
| Corylus avellana AAO65960 | 100 | 100 |
| Sesamum indicum AAD42942 | 92 | 92 |
| Brassica napus P29110 | 85 | 92 |

[a]% Identity is defined as percentage of amino acids that are identical between the two proteins.
[b]% Similarity is defined as percentage of amino acids that are identical or conserved between the two proteins. Comparisons between the diagnostic "□raline knot" motif (SEQ ID NO: 70) and the various oleosins was conducted using the National Center for Biotechnology Information (NCBI) BLASTP using the parameters: BLOSUM62 scoring matrix, Gap open = 9, Gap extension = 1, Expect = 20000, and Word size = 2.

In one embodiment, oleosin genes suitable in the present invention are those encoding a polypeptide comprised of an amino acid sequence sharing at least 50% identity or 75% similarity when compared to the diagnostic amino acid sequence (SEQ ID NO: 70). In another embodiment, suitable oleosin genes are those encoding a polypeptide comprised of an amino acid sequence sharing at least 55% identity or 80% similarity when compared to SEQ ID NO: 70. In a further embodiment, suitable oleosin genes are those encoding a polypeptide comprised of an amino acid sequence sharing at least 70% identity or 80% similarity when compared to SEQ ID NO: 70. In yet a further embodiment, suitable oleosin genes are those encoding a polypeptide comprised of an amino acid sequence sharing at least 85% identity or 90% similarity when compared to SEQ ID NO: 70.

Example 11

Effect of Oleosin Expression on the Production of β-carotene

The oleosin genes cloned in the high copy number vector pBlueScript SK during the construction of the cDNA library were transferred by electroporation in strain WS185 that produces β-carotene (WS185=MG1655 $P_{T5}$-dxs $P_{T5}$-idi $P_{T5}$-ispDF+pDCQ108 (tetR)) along with the pBlueScript SK+ as a vector control. Following transformation, the cells were plated on LB-tet and re-streaked on the same medium at room temperature to avoid strain instability sometime observed at 37° C. for these high copy plasmids.

Cultures of *E. coli* strains containing the cloned oleosin genes, the pBlueScript SK vector control were growth in LB-Tet-Amp medium at 37° C. The parent strain WS185 was grown in LB-Tet medium. Samples were taken at 12 hr and 24 hr to record the optical density at 600 nm as well as the absorption of the β-carotene extracted by 1 mL of acetone from 1 mL of cells as described in Example 8. The analytical results are presented in Tables 12 and 13.

TABLE 12

Increase in β-carotene Content in Strains Expressing Oleosin Genes in 12-hour Cultures

| Strain | OD600 | OD450 | OD450/OD600* |
|---|---|---|---|
| WS185 | 4.51 | 0.530 | 0.118 |
| WS185 + pBlueScript SK | 1.30 | 0.073 | 0.056 |
| WS185 + pOL2 | 2.65 | 0.538 | 0.203 |
| WS185 + pOL3 | 3.11 | 0.785 | 0.252 |
| WS185 + pOL4 | 4.02 | 0.467 | 0.116 |
| WS185 + pOL5 | 2.66 | 0.565 | 0.212 |
| WS185 + pOL7 | 3.16 | 0.738 | 0.234 |
| WS185 + pOL10 | 1.55 | 0.432 | 0.279 |
| WS185 + pOL11 | 1.68 | 0.278 | 0.165 |
| WS185 + pOL16 | 3.15 | 0.754 | 0.239 |
| WS185 + pOL17 | 1.13 | 0.079 | 0.070 |
| WS185 + pOL18 | 3.56 | 0.922 | 0.259 |
| WS185 + pOL19 | 0.61 | 0.078 | 0.128 |
| WS185 + pOL20 | 3.75 | 0.797 | 0.213 |

*A ratio OD450/OD600 of 0.1 correspond to approximately 1,260 µg of β-carotene/g of dry cell weight.

TABLE 13

Increase in β-carotene Content in Strains Expressing Oleosin Genes in 24-hour cultures

| Strain | OD600 | OD450 | OD450/OD600** |
|---|---|---|---|
| WS185 | 4.65 | 0.663 | 0.143 |
| WS185 + pBlueScript SK+ | 3.79 | 0.450 | 0.119 |
| WS185 + pOL2 | 2.37 | 0.545 | 0.230 |
| WS185 + pOL3 | 2.69 | 0.825 | 0.307 |
| WS185 + pOL4 | 4.37 | 0.505 | 0.116 |
| WS185 + pOL5 | 2.47 | 0.573 | 0.232 |
| WS185 + pOL7 | 3.02 | 0.744 | 0.246 |
| WS185 + pOL10 | 1.61 | 0.490 | 0.304 |
| WS185 + pOL11 | 3.22 | 0.560 | 0.174 |
| WS185 + pOL16 | 3.10 | 0.768 | 0.248 |
| WS185 + pOL17 | 4.10 | 0.493 | 0.120 |
| WS185 + pOL18 | 3.87 | 1.138 | 0.294 |
| WS185 + pOL19 | 3.23 | 0.519 | 0.161 |
| WS185 + pOL20 | 3.67 | 1.068 | 0.291 |

**A ratio OD450/OD600 of 0.1 correspond to approximately 1,260 µg of β-carotene/g of dry cell weight.

In both the 12-hour and 24-hour cultures, the presence oleosin genes can lead to more than a two-fold increase in the β-carotene content of the cells. This effect is not observed for the strain carrying the empty cloning vector. This effect is observed for all oleosins tested. This demonstrates that the effect of oleosins is general for the oleosin family.

Example 12

Effect of Oleosin Expression on the Production of Canthaxanthin

The oleosin genes cloned in the high copy number vector pBlueScript were transferred by electroporation in strain WS384 that produces the canthaxanthin (MG1655 $P_{T5}$-dxs $P_{T5}$-idi $P_{T5}$-isPDF+pDCQ307 (kanR)) along with the pBlueScript SK+ as a vector control. Following transformation, the cells were plated on LB-tet and re-streaked on the same medium at room temperature to avoid strain instability sometimes observed at 37° C.

Cultures of *E. coli* strains containing the cloned oleosin genes and the pBlueScript SK vector control were growth in LB-Kan-Amp medium at 37° C. The parent strain WS384 was grown in LB-Kan medium. Samples were taken at 12 hr and 24 hr to record the optical density at 600 nm as well as the absorption of the canthaxanthin extracted by 1 mL of acetone from 1 mL of cells as described in Example 8. The analytical results are presented in Table 14.

TABLE 14

Increase in Canthaxanthin Content in Strains Expressing Oleosin Genes in 24-hour Cultures

| Strain | OD600 | OD480 | OD480/OD600# |
|---|---|---|---|
| WS384 | 4.22 | 0.243 | 0.058 |
| WS384 + pBlueScript SK | 3.40 | 0.166 | 0.049 |
| WS384 + pOL2 | 2.18 | 0.279 | 0.128 |
| WS384 + pOL3 | 2.62 | 0.303 | 0.116 |
| WS384 + pOL4 | 3.62 | 0.362 | 0.100 |
| WS384 + pOL5 | 2.40 | 0.311 | 0.130 |
| WS384 + pOL7 | 3.11 | 0.400 | 0.129 |
| WS384 + pOL10 | 3.06 | 0.382 | 0.125 |
| WS384 + pOL11 | 2.75 | 0.312 | 0.113 |
| WS384 + pOL16 | 3.60 | 0.430 | 0.119 |
| WS384 + pOL17 | 3.37 | 0.280 | 0.083 |
| WS384 + pOL18 | 3.46 | 0.427 | 0.123 |
| WS384 + pOL19 | 3.63 | 0.227 | 0.063 |
| WS384 + pOL20 | 3.52 | 0.386 | 0.110 |

A ratio OD480/OD600 of 0.1 correspond to approximately 1,260 µg of canthaxanthin/g of dry cell weight.

In 24-hour cultures, the presence of oleosin genes can lead to more than a two-fold increase in the canthaxanthin content of the cells. This effect is not observed for the strain carrying the empty cloning vector. This experiment demonstrates that the effect of oleosin expression is not specific for a single carotenoid. This demonstrates that the effect of oleosins is general for the oleosin family.

Example 13

Expression Cloning of the *Glycine max* (Soy) Oleosin

To confirm that the increase in carotenoid titers is due to the expression of the oleosin genes, the gene of the *Glycine max* (soy) oleosin (OL20; SEQ ID NO: 63) was recloned in an expression vector pTrcHis2-topo (Invitrogen) using the primers listed in Table 15. The 153-bp gene was amplified from its first codon to the stop codon included.

TABLE 15

Primers for Amplification of the Glycine max (Soy) Oleosin Gene

| Primer Name | Primer Sequence | SEQ ID NO: |
|---|---|---|
| ST-OL20 | 5'-ATGGCAACCATTTCTACTGATCAACC-3' | 71 |
| SB-OL20(trpXbaI) | 5'-TATATTCTAGA<u>AAAAATGCCGCCAGCGGAACT GGCGGCTGTGGGATTA</u>GATTAATAAGTTCCTTGT GTGGCCTC-3' | 72 |

[1]The underlined sequences illustrate a sequence of trp terminator (36 nt).

The PCR fragment was cloned in vitro into the vector pTrc-His2-Topo as described by the manufacturer (Invitrogen) and the cloning reaction transferred into competent *E. coli* cells. The orientation of the insert was determined by sequencing the plasmid from the vector with primers provided by the manufacturer. The resulting plasmid, pTrc-OL20 carries the soy oleosin OL20 gene under the control of the IPTG-inducible trc promoter, facilitating inducible expression.

Example 14

Effect of Induction of *Glycine max* (Soy) Oleosin Expression on the Production of β-carotene A clone carrying the soy oleosin OL20 gene under the control of the IPTG-inducible trc promoter as well as the empty pTrc-His2 vector were each transferred by electroporation in strain WS185 that produces β-carotene.

(WS185=MG1655 $P_{T5}$-dxs $P_{T5}$-idi $P_{T5}$-ispDF+pDCQ108 (tetR)) along with the pBlueScript SK+ as a vector control. Following transformation, the cells were plated on LB-tet-Amp and re-streaked on the same medium at room temperature to avoid strain instability.

Cultures of *E. coli* strains containing the cloned OL20 oleosin gene in pTrc-OL20 or the pTrc-His2 vector control were growth in LB-Tet-Amp medium at 37° C. The parent strain WS185 was grown in LB-Tet medium. Samples were taken at periodic intervals to record growth by the optical density at 600 nm as well as the absorption of the β-carotene extracted by 1 mL of acetone from 1 mL of cells and measured at 450 nm as described in Example 8. The analytical results are presented in Table 16.

TABLE 16

Increase in β-carotene Content in Strains Expressing Oleosin Genes in 9-hour Cultures

| Strain | OD600 | OD450 | OD450/OD600 |
|---|---|---|---|
| WS185 | 4.6 | 0.514 | 0.112 |
| WS185 + pTrcHis2 | 4.55 | 0.499 | 0.110 |
| WS185 + pTrc-OL20 | 4.12 | 0.368 | 0.089 |
| WS185 (Induced) | 4.73 | 0.455 | 0.096 |
| WS185 + pTrcHis2 (Induced) | 4.54 | 0.422 | 0.093 |
| WS185 + pTrc-OL20 (Induced) | 3.73 | 0.778 | 0.209 |

No increase of β-carotene content was observed in the absence of the inducer IPTG. Addition of the inducer IPTG in the recipient strain WS185 or in WS185+pTrcHis2 did not result in the increase of carotenoid titers. Expression of oleosin upon induction of expression by addition of IPTG resulted in a 2× increase of β-carotene content.

This experiment shows that the increase in carotenoid titer is dependent upon expression of the oleosin gene.

What is claimed is:

1. A recombinant microbial production host for the production of hydrophobic compounds comprising:
   a) an intracellular system comprising heterologous genetic construct for the production of a hydrophobic compound; and
   b) at least one genetic construct encoding an oleosin polypeptide having an amino acid sequence comprising an oleosin diagnostic motif, said motif having about 70% identity to the amino acid sequence as set forth in SEQ ID NO: 70; wherein the hydrophobic compound is selected from the group consisting of isoprenoids, carotenoids, quinones, dolichols, tocopherols, fatty acids, terpenes, steroids, chlorophylles, polyhydroxyalkanoates, and natural rubber.

2. A production host according to claim 1 selected from the group consisting of bacteria, yeast, and algae.

3. A production host according to claim 2 wherein the bacteria is selected from the group consisting of *Salmonella*, *Bacillus*, *Acinetobacter*, *Rhodococcus*, *Streptomyces*, *Escherichia*, *Pseudomonas*, *Methylomonas*, *Methylobacter*, *Alcaligenes*, *Synechocystis*, *Anabaena*, *Thiobacillus*, *Methanobacterium*, *Klebsiella*, *Burkholderia*, *Sphingomonas*, *Paracoccus*, *Pandoraea*, *Delftia*, and *Comamonas*.

4. A production host according to claim 2 wherein the yeast is selected from the group consisting of *Aspergillus*, *Trichoderma*, *Saccharomyces*, *Pichia*, *Candida*, *Yarrowia*, and *Hansenula*.

5. A production host according to claim 2 wherein the algae is selected from the group consisting of *Spirulina*, *Haemotacoccus*, and *Dunalliela*.

6. A production host according to claim 1 wherein said an amino acid sequence comprising an oleosin diagnostic motif has at least 75% similarity to SEQ ID NO: 70.

7. A production host according to claim 1 wherein said oleosin genetic construct is operably linked to a suitable promoter.

8. A production host according to claim 7 wherein said suitable promoter in constitutive.

9. A production host according to claim 7 wherein said suitable promoter is inducible.

10. A production host according to claim 1 wherein said oleosin construct is chromosomally or extrachromosomally expressed.

11. A method for the production of a hydrophobic compound comprising:
   (a) providing a recombinant microbial production host comprising:
      i) an intracellular system comprising heterologous genetic construct for the production of a hydrophobic compound; and
      ii) at least one genetic construct encoding an oleosin polypeptide having an amino acid sequence comprising an oleosin diagnostic motif, said motif having about 70% identity to the amino acid sequence as set forth in SEQ ID NO: 70; and
   (b) growing the production host of (a) under conditions whereby a hydrophobic compound is produced; wherein the hydrophobic compound is selected from the group consisting of isoprenoids, carotenoids, quinones, dolichols, tocopherols, fatty acids, terpenes, steroids, chlorophylles, polyhydroxyalkanoates, and natural rubber.

12. A method according to claim 11 wherein the hydrophobic compound is optionally recovered from the production host.

13. A method according to claim 11 wherein the titer of hydrophobic compound produced by said production host is at least about 2 fold greater relative to a production host lacking said oleosin construct when grown under the similar conditions.

14. A method according to claim 11 wherein the carotenoid is selected from the group consisting of lycopene, β-carotene, zeaxanthin, lutein, canthaxanthin, and astaxanthin.

* * * * *